United States Patent
Shibata et al.

(10) Patent No.: US 6,500,503 B2
(45) Date of Patent: Dec. 31, 2002

(54) CYCLOHEXANE DERIVATIVES, LIQUID CRYSTAL COMPOSITIONS COMPRISING THE SAME AND LIQUID CRYSTAL DISPLAY DEVICES

(75) Inventors: Koichi Shibata, Chiba (JP); Shuichi Matsui, Chiba (JP); Hiroyuki Tekeuchi, Chiba (JP); Katsuyuki Kawano, Chiba (JP); Yasuhiro Kubo, Chiba (JP); Etsuo Nakagawa, Chiba (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 33 days.

(21) Appl. No.: 09/842,254

(22) Filed: Apr. 26, 2001

(65) Prior Publication Data

US 2002/0066888 A1 Jun. 6, 2002

(30) Foreign Application Priority Data

Apr. 26, 2000 (JP) .......................................... 2000-126533

(51) Int. Cl.$^7$ .................. C09K 19/30; C09K 19/34; C09K 19/02; C07C 43/225; C07C 25/18; C07C 319/06

(52) U.S. Cl. .............. 428/1.1; 252/299.61; 252/299.63; 252/299.66; 252/299.1; 570/127; 570/129; 549/369

(58) Field of Search ...................... 252/299.01, 299.61, 252/299.63, 299.64, 299.66, 299.67; 428/1.1; 570/127, 129; 549/369; 544/242, 298

(56) References Cited

U.S. PATENT DOCUMENTS

| 4,797,228 A | 1/1989 | Goto et al. ............. 252/299.63 |
| 5,032,313 A | 7/1991 | Goto et al. ............. 252/299.63 |

FOREIGN PATENT DOCUMENTS

| DE | 198 14 550 | 10/1999 |
| EP | 0 781 826 | 7/1997 |
| JP | 5-70382 | * 3/1993 |
| JP | 7-84254 | 3/1995 |
| JP | 9-176645 | 7/1997 |
| JP | 11-302653 | 11/1999 |

OTHER PUBLICATIONS

Yamaguchi, Y., et al. "Late–News Paper: Wide–Viewing–Angle Display Mode for the Active–Matrix LCD Using Bend–Alignment Liquid–Crystal Cell", Society for Information Display International Symposium (SID 1993), pp. 277–280.
Uchida, T., et al. "A Bright Reflective LCD Using Optically Compensated Bend Cell with Gray–Scale Capability and Fast Response", Society for Information Display International Symposium (SID 1996), pp. 618–621.
Database Chemabs Online! Chemical Abstracts service, Columbus, Ohio, US; Shintani, Seiji et al. "Preparation of trans–fluoroethylene derivatives with low viscosity and liquid–crystal compositions containing them", retrieved from STN Database accession No. 118:264004 XP002173978 Abstract & JP 05 070382 A (Asahi Glass Co., Ltd., Japan; Seimi Chem KK) Mar. 23, 1993.
Database Chemabs Online! Chemical Abstracts service, Columbus, Ohio, US; Shintani, Seiji et al. "1,1–Difluoroethane derivatives and liquid–crystal compositions containing them" retrieved from STN Database accession No. 119:238077 XP002173979 Abstract & JP 05 051332 A (Asahi Glass Co., Ltd., Japan; Seimi Chem KK) Mar. 2, 1993.
Database Chemabs Online! Chemical Abstracts service, Columbus, Ohio, US; Takehara, Sadao et al. "Preparation of 1,2–diaryl–1,1–difluoroethane derivatives and liquid crystal compositions containing them for display devices" retrieved from STN Database accession No. 119:191995 XP002173980 Abstract & JP 05 085971 A (Dainippon Ink & Chemicals, Japan; Sagami Chem Res) Apr. 6, 1993.

* cited by examiner

Primary Examiner—Shean C. Wu
(74) Attorney, Agent, or Firm—Wenderoth, Lind & Ponack, L.L.P.

(57) ABSTRACT

Liquid crystalline compounds are disclosed which have large dielectric anisotropy and relatively low viscosity, and which are represented by formula (1)

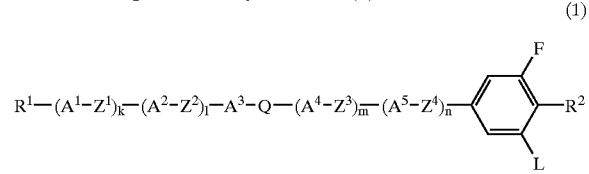

wherein $R^1$ represents hydrogen or $C_1$–$C_{15}$ alkyl in which one or more non-adjacent methylene may be replaced by oxygen, sulfur or —CH=CH— and one or more hydrogen may be replaced by halogen; $R^2$ represents hydrogen, cyano, halogen or $C_1$–$C_{15}$ alkyl in which one or more non-adjacent methylene may be replaced by oxygen, sulfur or —CH=CH— and one or more hydrogen may be replaced by halogen; L represents halogen or hydrogen; $A^1$, $A^2$, $A^4$ and $A^5$ each independently represent trans-1,4-cyclohexylene or 1,4-phenylene, one or more —CH$_2$— in the trans-1,4-cyclohexylene may be replaced by oxygen or sulfur, one or more =CH— in the 1,4-phenylene may be replaced by nitrogen, and one or more hydrogen in the 1,4-phenylene ring may be replaced by halogen; $A^3$ represents trans-1,4-cyclohexylene in which one or more —CH$_2$— may be replaced by oxygen or sulfur; $Z^1$,$Z^2$,$Z^3$ and $Z^4$ each independently represent —COO—, —OCO—, —CH$_2$CH$_2$—, —(CH$_2$)$_4$—, —CH$_2$O —, —OCH$_2$—, —CF$_2$O—, —OCF$_2$— or a single bond; Q represents —CF$_2$CH$_2$— or —CH$_2$CF$_2$—; and k, l, m and n each independently represent 0 or 1 with the condition of k+l+m+n≦2. Further, liquid crystal compositions comprising at least one liquid crystalline compound of formula (1) and liquid crystal display devices composed of the compositions are disclosed.

20 Claims, No Drawings

CYCLOHEXANE DERIVATIVES, LIQUID CRYSTAL COMPOSITIONS COMPRISING THE SAME AND LIQUID CRYSTAL DISPLAY DEVICES

BACKGROUND OF THE INVENTION

1. Field of the Invention

This invention relates to cyclohexane derivatives which are liquid crystalline compounds suitable as a component in a liquid crystal composition, liquid crystal compositions comprising the same and liquid crystal display devices composed of these liquid crystal compositions.

2. Description of Related Art

A liquid crystal display device utilizing an optical anisotoropy and a dielectric anisotropy of a liquid crystal substance is classified into a twisted nematic type (TN type), a super twisted nematic type (STN type), a dynamic scattering type (DS type), a guest-host type (G-H type) and DAP type, in view of a display system. It is also classified into a static drive system, a time rate drive system, an active matrix drive system and 2 cycle drive system, in view of a drive system. Various liquid crystal substances having different properties depending on their application are used for these liquid crystal display devices. As a common property, any liquid crystal substance needs to have a stability to external environmental factors such as moisture, air, heat and light, to exhibit liquid crystal phase within as broad the temperature range as possible focusing on room temperature, to have low viscosity and to make the driving voltage low when the display device is driven. Further, it needs to have the characteristics desired according to each display device, for example, the optimum dielectric anisotropy ($\Delta\epsilon$) and the optimum optical anisotropy ($\Delta n$).

However, there is no substance which meets such all requirements with a single compound now. The present condition is mixing several to about twenty sorts of liquid crystalline compounds to prepare a liquid crystal composition and using the composition as liquid crystal material. The term "liquid crystalline compound" as used herein refers generically to a compound having a liquid crystal phase and a compound not impairing a liquid crystal phase when mixed with other liquid crystal compounds.

Therefore, it is desirable that liquid crystalline compounds used as a component in the composition have good compatibility each other and also they have good compatibility even at a cryostatic temperature, since the demand to the use under various environment is increasing recently.

In recent years, liquid crystal display device is required with higher quality, especially in a display performance, for example, contrast, display capacity, response time, etc. To meet the requirement, the demand for the display device of an active matrix system represented by a TFT (thin film transistor) system is increasing in display mode fields, mainly television and a view finder.

The display device of STN system has been often used in the display fields such as a pocket phone and a personal computer, because of its low cost, easy manufacturing process while having large display capacity.

The development tendency in recent years in these fields is advanced focusing on a downsizing and portability of a liquid crystal display device as observed in the television and note type personal computer which are portable by downsizing and light saving. The liquid crystal material used in connection with this requires a liquid crystalline compound of low driving voltage, i.e., those capable of providing reduced threshold voltage, and a liquid crystal composition of low driving voltage comprising the same.

The threshold voltage ($V_{th}$) is shown by the following formula as known well (H. J. Deuling, et al., Mol. Cryst. Liq. Cryst., 27 (1975) 81).

$V_{th}=\eta(K/\epsilon_0\Delta\epsilon)^{1/2}$ in which K is an elastic constant of liquid crystal material and $\epsilon_0$ is a dielectric constant in a vacuum. As seen from the above formula, two ways can be considered whether $\Delta\epsilon$ is increased or K is decreased, in order to reduce $V_{th}$. However, with the present technology, it is still difficult to control the elastic constant K of liquid crystal material actually. Under the present circumstances, one complies with a demand by using a liquid crystal material of large $\Delta\epsilon$. For such circumstances, liquid crystalline compounds of large $\Delta\epsilon$ have been developed actively.

At present, most liquid crystal compositions used for the display device of TFT system are composed of fluorine-containing liquid crystal materials. The reason is that the display device of TFT system requires the liquid crystal composition capable of providing high voltage holding rate (V.H.R) under low temperature dependence, but there is no other liquid crystalline compound except for fluorine-containing compounds to meet such requirements.

To increase $\Delta\epsilon$ in the liquid crystalline compound, it is effective to maintain a substituent having large dipole moment such as cyano and trifluoromethyl in the terminal group as well known, or to replace 1,4-phenylene in the compound by halogen such as fluorine, so that the direction of a dipole moment may become identical with that of the terminal substituent. However, it has been considered to be difficult to increase only $\Delta\epsilon$, while controlling both an increase in viscosity and a reduction in the temperature range of a liquid crystal phase, since the number of replaced fluorine atom is proportional to the viscosity and the number of replaced fluorine atom is increased with reducing the temperature range of a liquid crystal phase.

In recent years, development of the liquid crystal display, especially using a reflected type TFT system is also active. For this reflected type liquid crystal display, a compound of low $\Delta n$ is required.

As compounds already reported, U.S. Pat. No. 4,797,228 discloses the compound of the following formula (A) and Japanese Patent Kokai 2-233626 discloses the compound of the following formula (B).

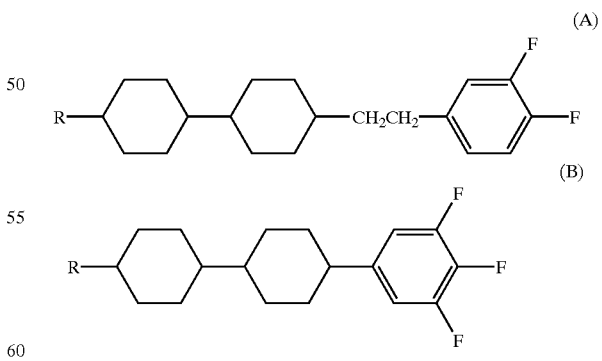

in which R represents a straight-chain alkyl.

Among these, the compound of formula (A) is reported to be comparatively stable and highly reliable. However, $\Delta\epsilon$ of the compound (A) is comparatively as small as about 3–5 and also $\Delta\epsilon$ of the liquid crystal composition consisting of only the same is small, which cannot reduce the driving voltage. To make up for this defect, the compound of formula (B) was developed. This compound had large Δε and low viscosity, and could reduce the driving voltage without increasing the viscosity of the liquid crystal composition.

Accordingly, it has been desired to develop a liquid crystal material of large Δε without reducing the liquid crystal phase temperature range, and further of small Δn and high stability.

SUMMARY OF THE INVENTION

An object of the present invention is to provide a new liquid crystalline compound having large Δε and relatively low viscosity which can overcome the defects of the prior art as mentioned above, a liquid crystal composition comprising said liquid crystalline compound and a liquid crystal display device composed of said liquid crystal composition.

We have investigated various compounds in an effort to solve the aforesaid problems and found new liquid crystalline compounds having more improved characteristics than known liquid crystalline compounds, thus leading to the completion of the present invention.

In the first aspect, the present invention relates to a liquid crystalline compound represented by formula (1)

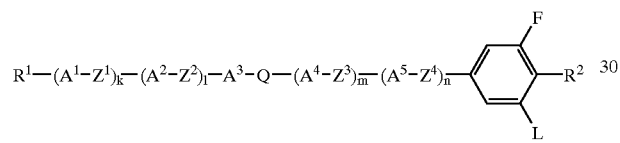

(1)

wherein $R^1$ represents hydrogen or $C_1$–$C_{15}$ alkyl in which one or more non-adjacent methylene may be replaced by oxygen, sulfur or —CH=CH— and one or more hydrogen may be replaced by halogen; $R^2$ represents hydrogen, cyano, halogen or $C_1$–$C_{15}$ alkyl in which one or more non-adjacent methylene may be replaced by oxygen, sulfur or —CH=CH— and one or more hydrogen may be replaced by halogen; L represents halogen or hydrogen; $A^1$, $A^2$, $A^4$ and $A^5$ each independently represent trans-1,4-cyclohexylene or 1,4-phenylene, one or more —CH$_2$— in the trans-1,4-cyclohexylene may be replaced by oxygen or sulfur, one or more =CH— in the 1,4-phenylene may be replaced by nitrogen, and one or more hydrogen in the 1,4-phenylene ring may be replaced by halogen; $A^3$ represents trans-1,4-cyclohexylene in which one or more —CH$_2$— may be replaced by oxygen or sulfur; $Z^1$, $Z^2$, $Z^3$ and $Z^4$ each independently represent —COO—, —OCO—, —CH$_2$CH$_2$—, —(CH$_2$)$_4$—, CH$_2$O—, —OCH$_2$—, —CF$_2$O—, —OCF$_2$— or a single bond; Q represents —CF$_2$CH$_2$— or —CH$_2$CF$_2$—; and k, l, m and n each independently represent 0 or 1 with the condition of k+l+m+n≦2.

The embodiments of the present compounds include the following cases in formula (1):

k=l=m=n=0,
k+l=1 and m=n=0,
k=l=0 and m+n=1,
k+l=1 and m+n=1,
k=l=0 and m=n=1,
$A^3$ is trans-1,4-cyclohexylene,
$R^2$ is fluorine, $A^3$ is trans-1,4-cyclohexylene and $R^2$ is fluorine, k+l=1, m=n=0, $A^1$ or $A^2$ is trans-1,4-cyclohexylene, $A^3$ is trans-1,4-cyclohexylene, and $Z^1$ or $Z^2$ is a single bond, or k+l=1, m=n=0, $A^1$ or $A^2$ is trans-1,4-cyclohexylene, $A^3$ is trans-1,4-cyclohexylene, $Z^1$ or $Z^2$ is a single bond, and $R^2$ and L is fluorine.

In the second aspect, the present invention relates to a liquid crystal composition which comprises at least one liquid crystalline compound represented by formula (1). In one embodiment of the present second invention, the liquid crystal composition may further comprise as a second component at least one compound selected from the group consisting of the compound of formula (2), the compound of formula (3) or the compound of formula (4)

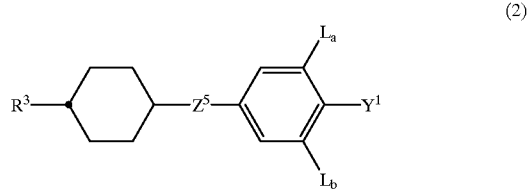

(2)

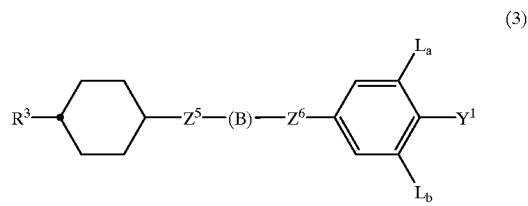

(3)

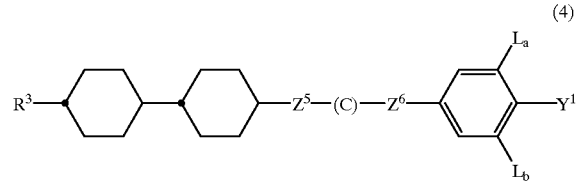

(4)

wherein $R^3$, $Y^1$, $L_a$, $L_b$, $Z^5$ and $Z^6$ may be identical or different between each formula; $R^3$ represents $C_1$–$C_{10}$ alkyl in which one or more non-adjacent methylene may be replaced by oxygen or —CH=CH— and any hydrogen may be replaced by fluorine; $Y^1$ represents fluorine, chlorine, OCF$_3$OCHF$_2$, CF$_3$, CHF$_2$, CH$_2$F, OCF$_2$CHF$_2$ or OCF$_2$CHF CF$_3$; $L_a$ and $L_b$ each independently represent hydrogen or fluorine; $Z^5$ and $Z^6$ each independently represent —CH$_2$CH$_2$—, —(CH$_2$)$_4$—, —COO—, —CF$_2$O—, —OCF$_2$—, —CH=CH— or a single bond; six-membered ring B represents trans-1,4-cyclohexylene, 1,3-dioxane-2,5-diyl or 1,4-phenylene in which hydrogen may be replaced by fluorine; six-membered ring C represents trans-1,4-cyclohexylene or 1,4-phenylene in which hydrogen may be replaced by fluorine; and in the above compound of each formula, each atom constituting the compound may include its isotope.

In another embodiment of the second invention, the liquid crystal composition may further comprise as a second component at least one compound selected from the group consisting of the compound of formula (5) or the compound of formula (6)

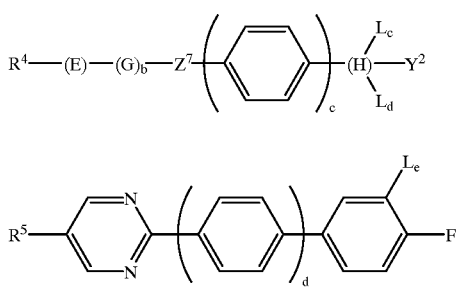

wherein $R^4$ and $R^5$ each independently represent $C_1$–$C_{10}$ alkyl in which one or more non-adjacent methylene may be replaced by oxygen or —CH=CH— and any hydrogen may be replaced by fluorine; $Y^2$ represents —CN or —C≡C—CN; six-membered ring E represents trans-1,4-cyclohexylene, 1,4-phenylene, 1,3-dioxane-2,5-diyl or pyrimidine-2,5-diyl; six-membered ring G represents trans-1,4-cyclohexylene, 1,4-phenylene in which hydrogen may be replaced by fluorine or pyrimidine-2,5-diyl; six-membered ring H represents trans-1,4-cyclohexylene or 1,4-phenylene; $Z^7$ represents —CH$_2$CH$_2$—, —COO— or a single bond; $L_c$, $L_d$ and $L_e$ each independently represent hydrogen or fluorine; b, c and d each independently represent 0 or 1; and in the above compound of each formula, each atom constituting the compound may include its isotope.

In further embodiment of the second invention, the liquid crystal composition may further comprise as a second component at least one compound selected from the group consisting of the compound of formula (2), the compound of formula (3) and the compound of formula (4) and as a third component at least one compound selected from the group consisting of the compound of formula (7), the compound of formula (8) and the compound of formula (9)

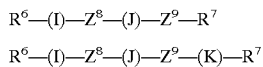  (7)

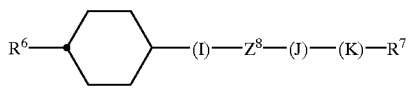  (8)

(9)

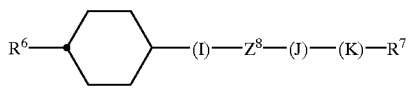

wherein $R^6$, $R^7$, I, J and K may be identical or different between each formula; $R^6$ and $R^7$ each independently represent $C_1$–$C_{10}$ alkyl in which one or more non-adjacent methylene may be replaced by oxygen or —CH=CH— and any hydrogen may be replaced by fluorine; I, J and K each independently trans-1,4-cyclohexylene, pyrimidine-2,5-diyl or 1,4-phenylene in which hydrogen may be replaced by fluorine; $Z^8$ and $Z^9$ each independently represent —C≡C—, —COO—, —CH$_2$CH$_2$—, —CH=CH— or a single bond, and in the above compound of each formula, each atom constituting the compound may include its isotope.

In further embodiment of the second invention, the liquid crystal composition may further comprise as a second component at least one compound selected from the group consisting of the compound of formula (5) or the compound of formula (6) and as a third component at least one compound selected from the group consisting of the compound of formula (7), the compound of formula (8) or the compound of formula (9).

In further embodiment of the second invention, the liquid crystal composition may further comprise as a second component at least one compound selected from the group consisting of the compound of formula (2), the compound of formula (3) or the compound of formula (4) and as a third component at least one compounds selected from the group consisting of the compound of formula (5) or the compound of formula (6), and as a fourth component at least one compound selected from the group consisting of the compound of formula (7), the compound of formula (8) or the compound of formula (9).

In still further embodiment of the second invention, the liquid crystal compositions as recited above may further contain any optically active compound.

In the third aspect, the present invention relates to a liquid crystal display device composed of any of the present liquid crystal compositions as recited above.

DETAILED DESCRIPTION OF THE INVENTION

The liquid crystalline compounds of the present invention represented by formula (1) have a partial structure comprising 1,1-difluoroethylene and exhibit excellent characteristics, especially low Δn and large Δε as described later by a synergistic effect of the halogen atom or the like substituted on 1,4-phenylene ring.

The compounds of formula (1) are specified by those represented by the following formulae (1a) to (1f).

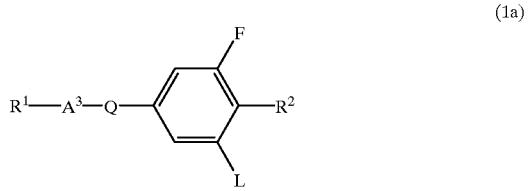  (1a)

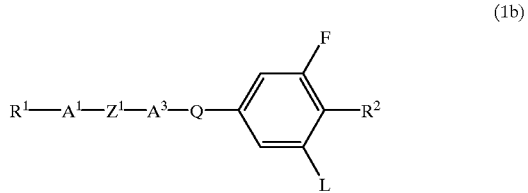  (1b)

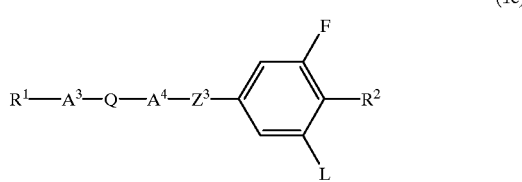  (1c)

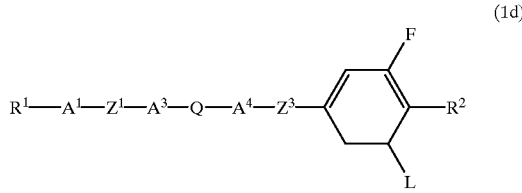  (1d)

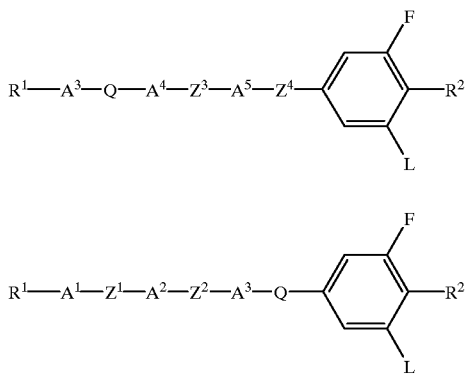

In these formulae, $A^1, A^2, A^3, A^4, A^5, L, R^1, R^2, Q, Z^1, Z^2, Z^3$ and $Z^4$ represent the same meanings as described above.

Of these specific compounds, the dicyclic compound of formula (1a) (k=l=m=n=0) has large $\Delta\epsilon$, relatively small $\Delta n$, low viscosity and good compatibility at low temperature. This compound can provide a composition for high-speed response when used as a component of the liquid crystal composition, since it can reduce the viscosity while maintaining $\Delta\epsilon$ of the composition.

The tricyclic compounds, i.e., the compound of formula (1b) (k=1 and l=m=n=0) and the compound of formula (1c) (k=l=n=0 and m=1) and the tetracyclic compounds, i.e., the compound of formula (1d) (k=m=1 and l=n=0) or the compound of formula (1e) (k=l=0 and m=n=1) have large $\Delta\epsilon$, relatively low viscosity and relatively broad temperature range of liquid phase. These compounds are useful for expanding the liquid phase temperature range to a high temperature side while maintaining the dielectric anisotropy of the resulting composition, when used as a component of the liquid crystal composition.

Of the compounds as specifically recited above, preferable examples of the compounds included in those of formula (1b) are more specifically recited by the compounds of the following formulas (1b-1) to (1b-16). Preferable examples of the compounds included in those of formula (1c) are more specifically recited by the compounds of the following formulas (1c-1) to (1c-22). Preferable examples of the compounds included in those of formula (1d) are more specifically recited by the compounds of the following formulas (1d-1) to (1d-20). Preferable examples of the compounds included in those of formula (1e) are more specifically recited by the compounds of the following formulas (1e-1) to (1e-20). Preferable examples of the compounds included in those of formula (1f) are more specifically recited by the compounds of the following formulas (1f-1) to (1f-18).

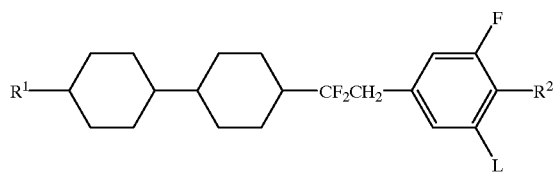

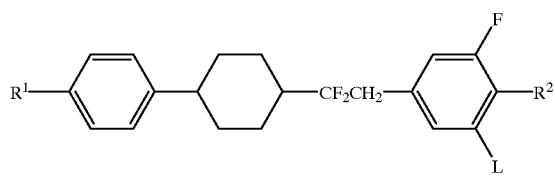

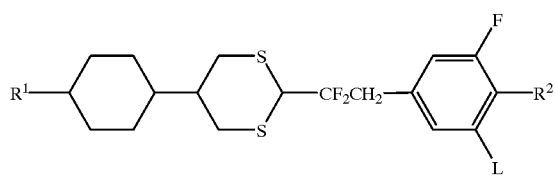

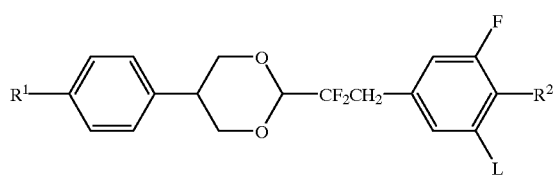

(1b-5)
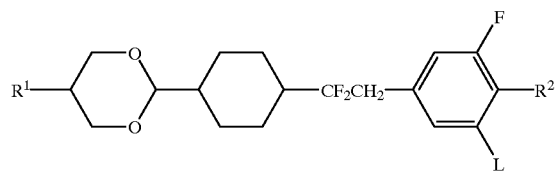
(1b-6)
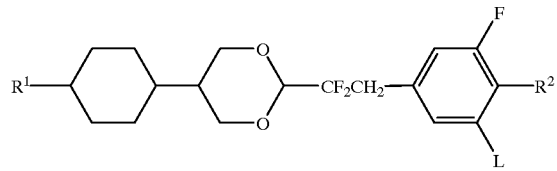
(1b-7)
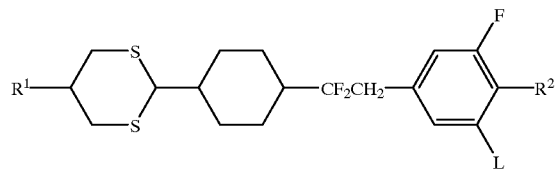
(1b-8)
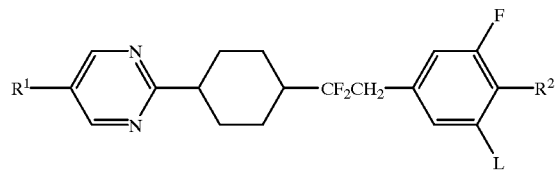
(1b-9)
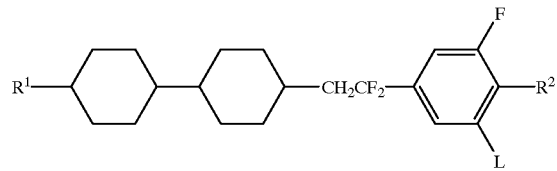
(1b-10)
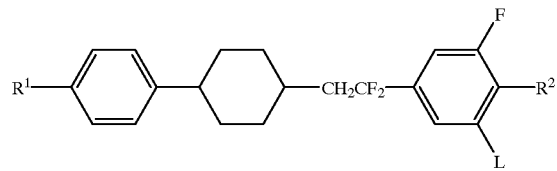
(1b-11)
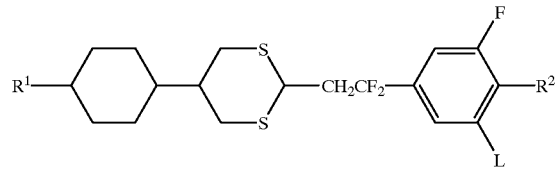

-continued
(1b-12)
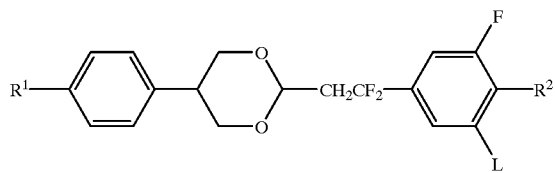
(1b-13)
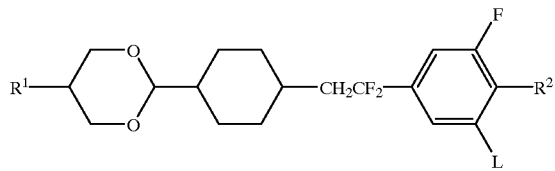
(1b-14)
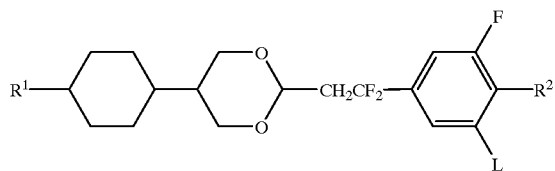
(1b-15)
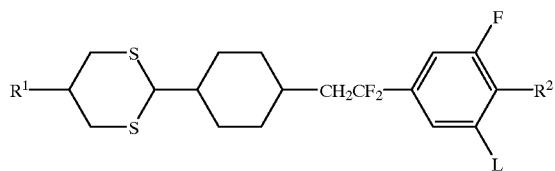
(1b-16)
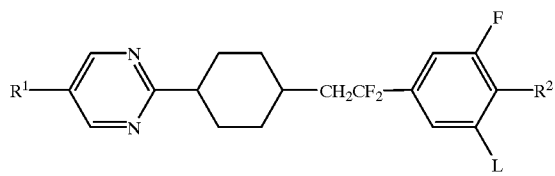
(1c-1)
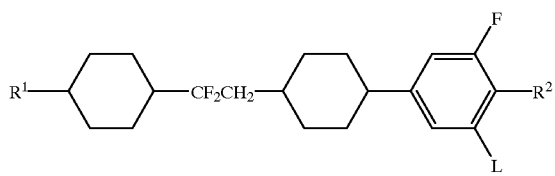
(1c-2)
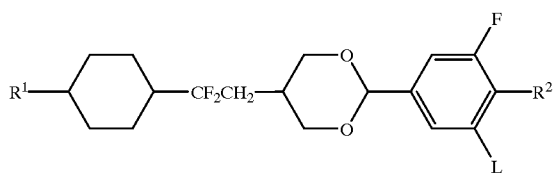

-continued
(1c-3)
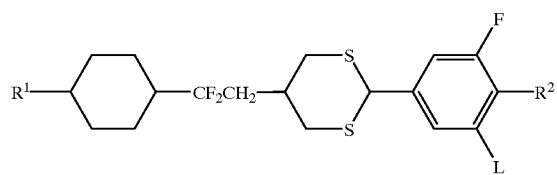
(1c-4)
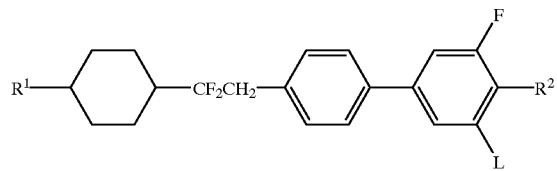
(1c-5)
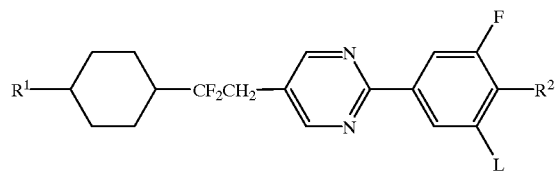
(1c-6)
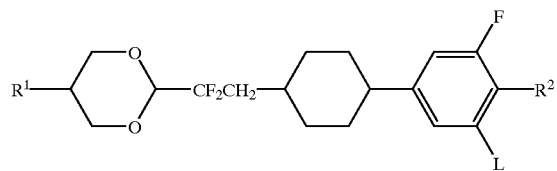
(1c-7)
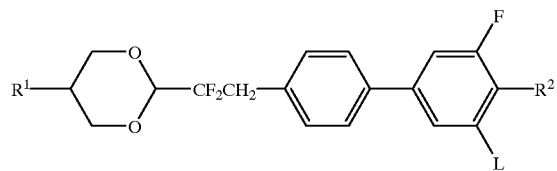
(1c-8)
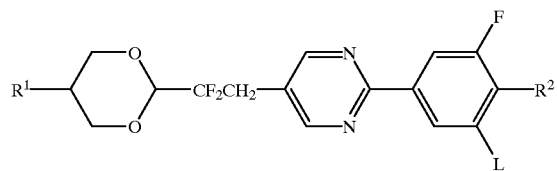
(1c-9)
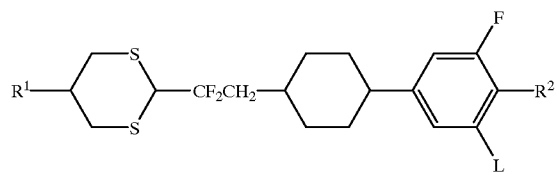

(1c-10)
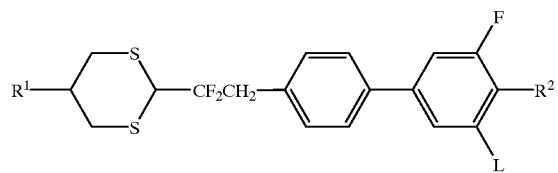
(1c-11)
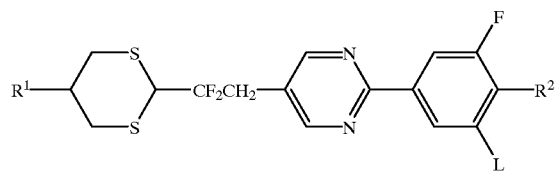
(1c-12)
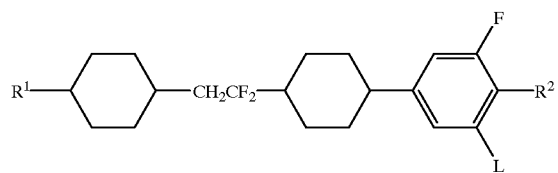
(1c-13)
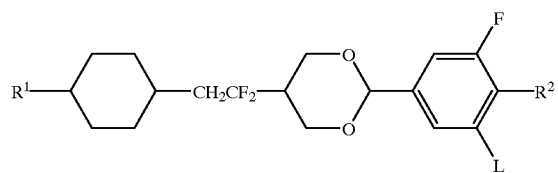
(1c-14)
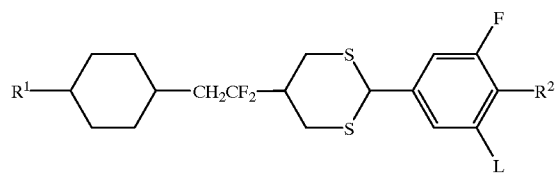
(1c-15)
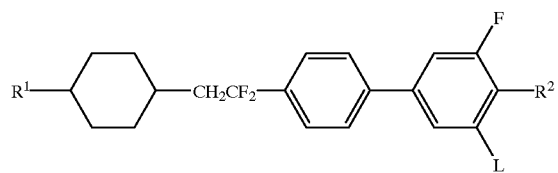
(1c-16)
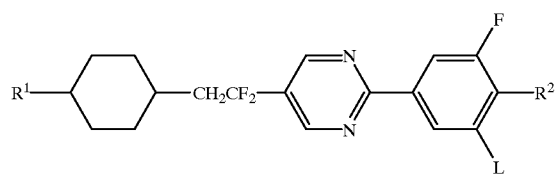

(1c-17)
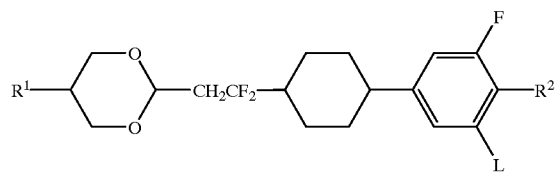
(1c-18)
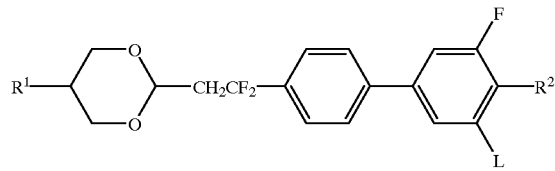
(1c-19)
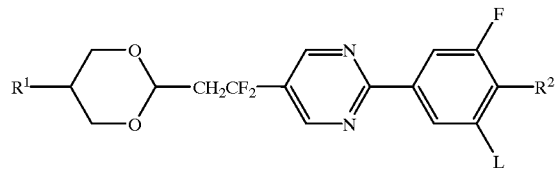
(1c-20)
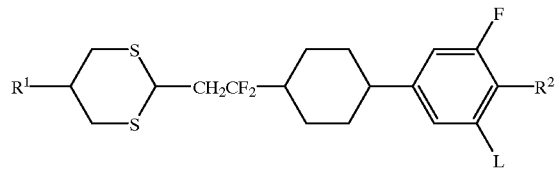
(1c-21)
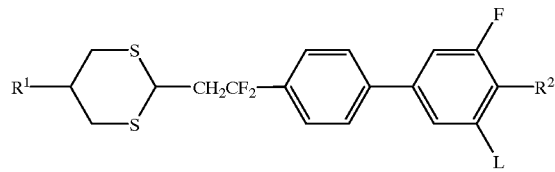
(1c-22)
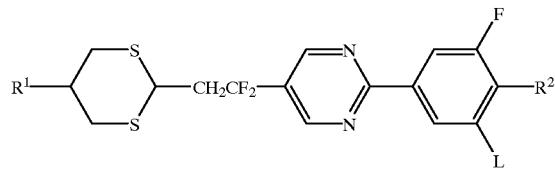
(1d-1)
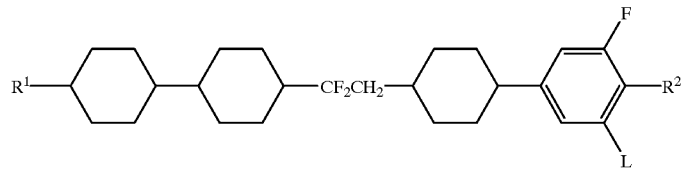

-continued
(1d-2)
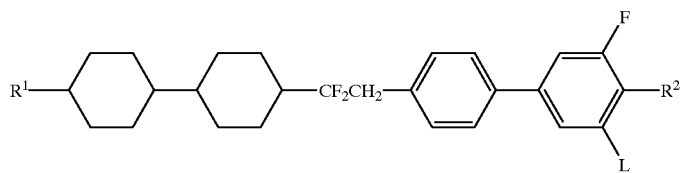
(1d-3)
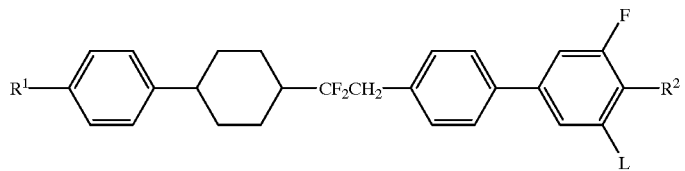
(1d-4)
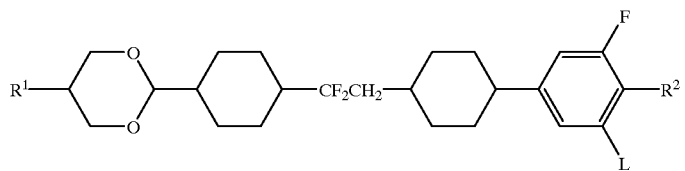
(1d-5)
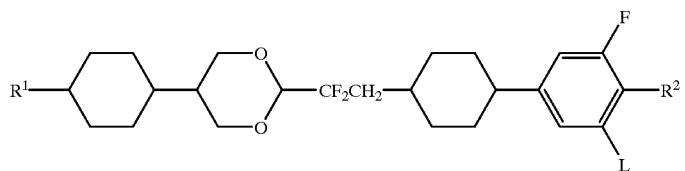
(1d-6)
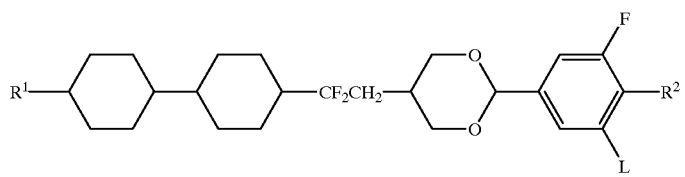
(1d-7)
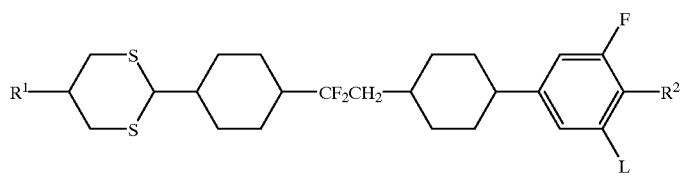
(1d-8)
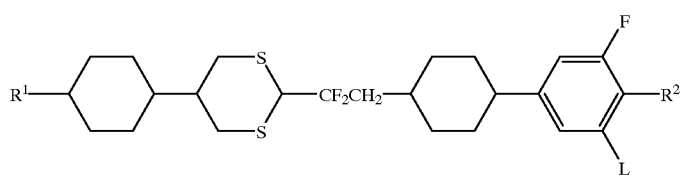

-continued
(1d-9)
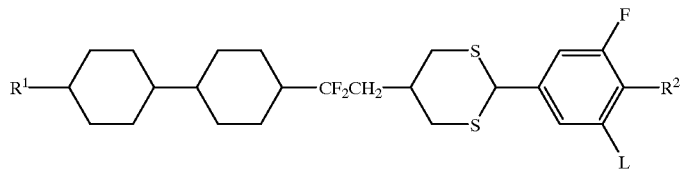
(1d-10)
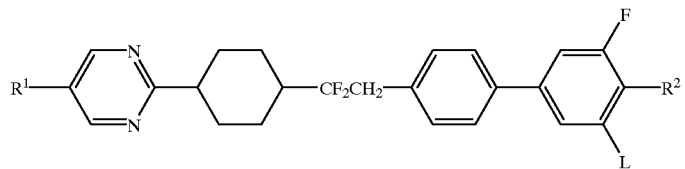
(1d-11)
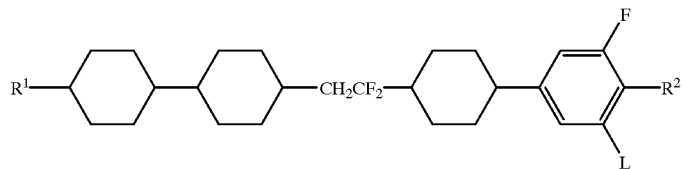
(1d-12)
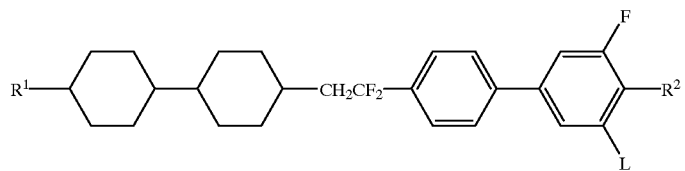
(1d-13)
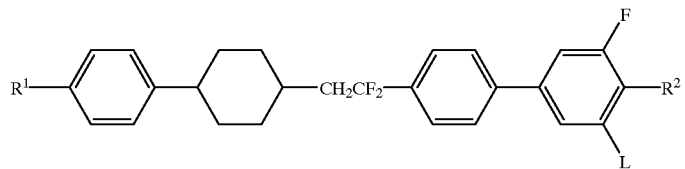
(1d-14)
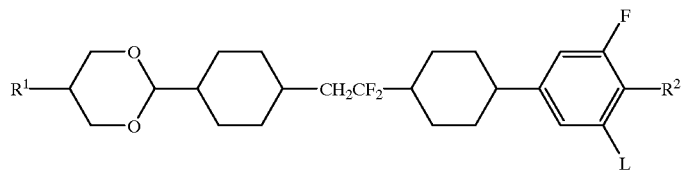
(1d-15)
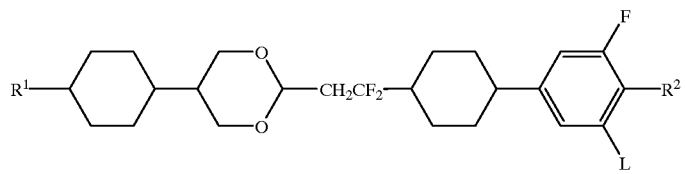

-continued
(1d-16)
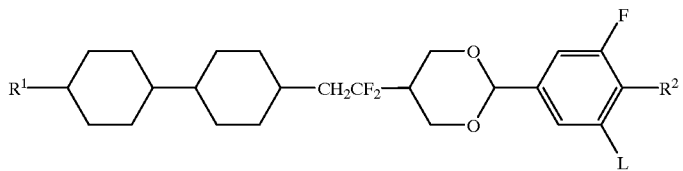
(1d-17)
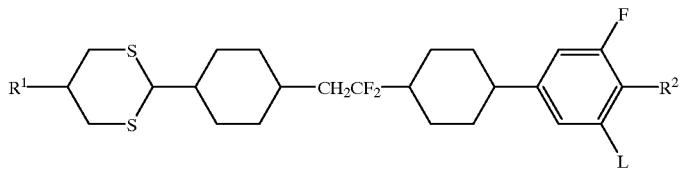
(1d-18)
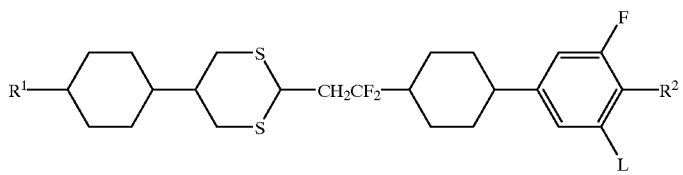
(1d-19)
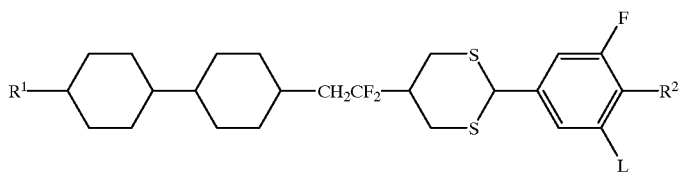
(1d-20)
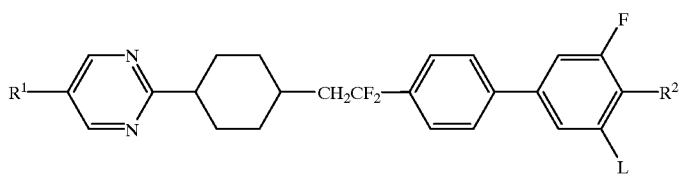
(1e-1)
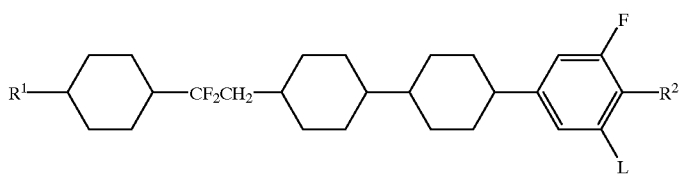
(1e-2)
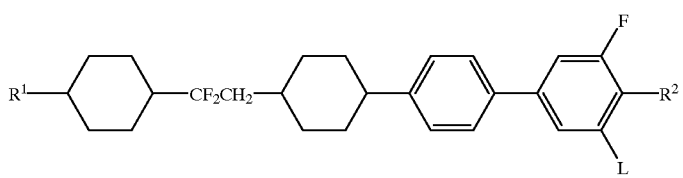

(1e-3)
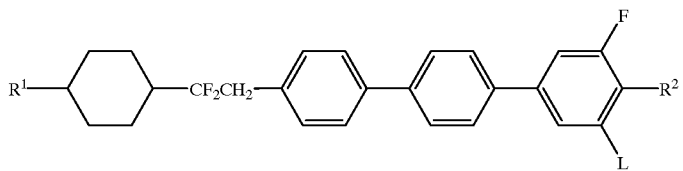
(1e-4)
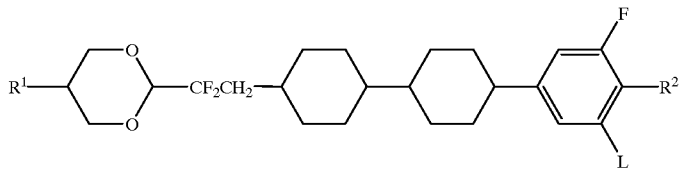
(1e-5)
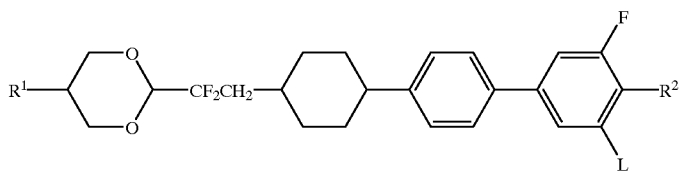
(1e-6)
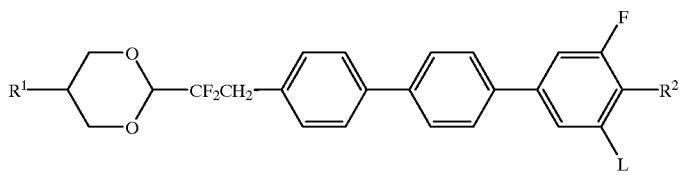
(1e-7)
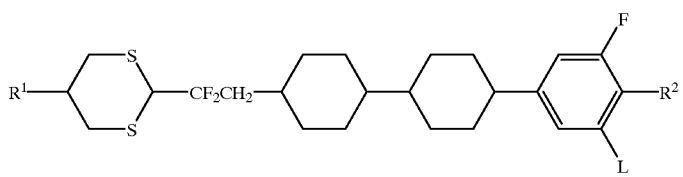
(1e-8)
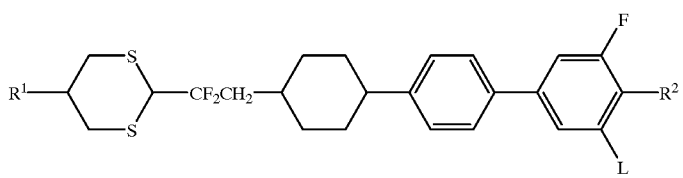
(1e-9)
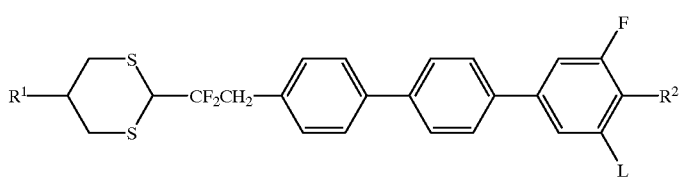

(1e-10)
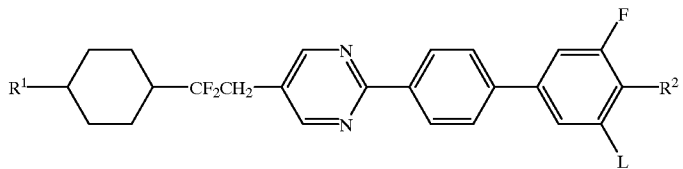
(1e-11)
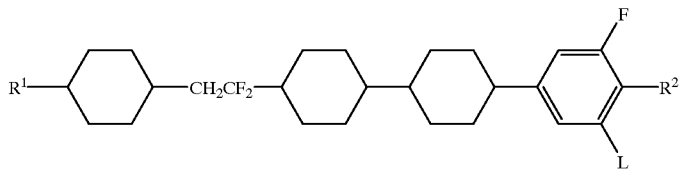
(1e-12)
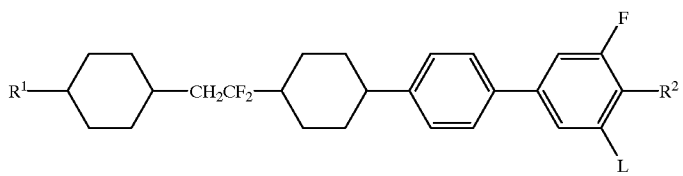
(1e-13)
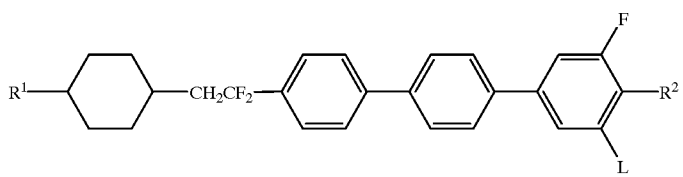
(1e-14)
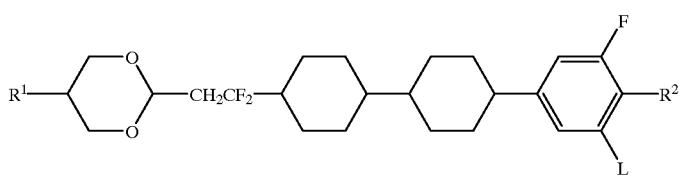
(1e-15)
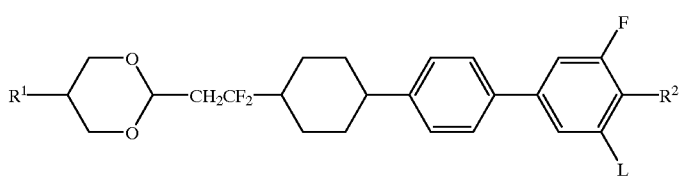
(1e-16)
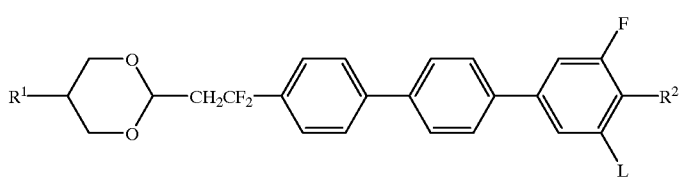

(1e-17)
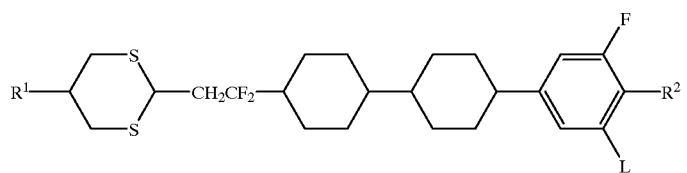
(1e-18)
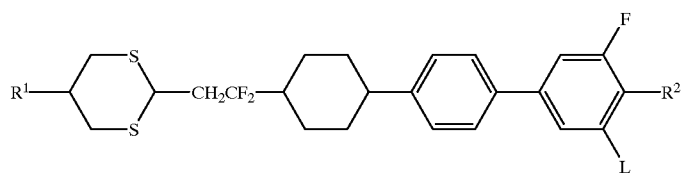
(1e-19)
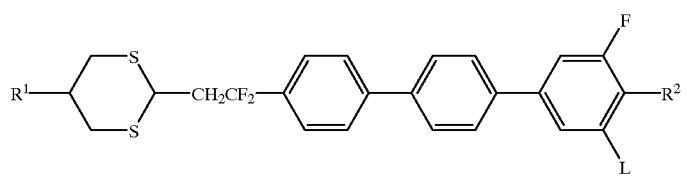
(1e-20)
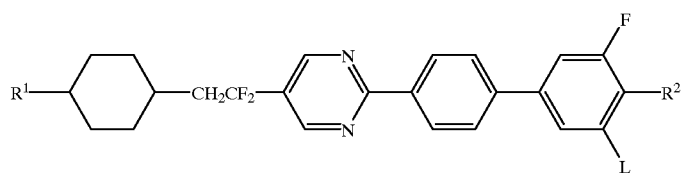
(1f-1)
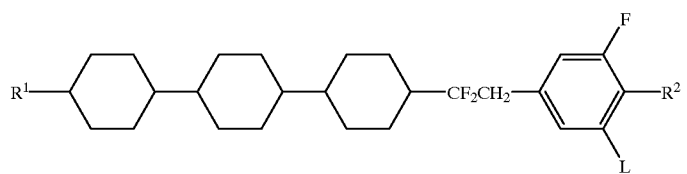
(1f-2)
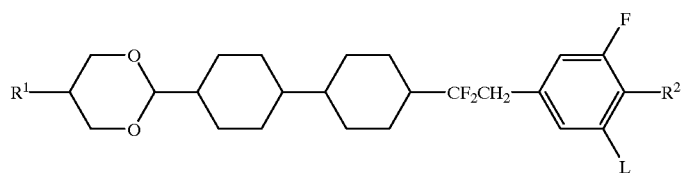
(1f-3)
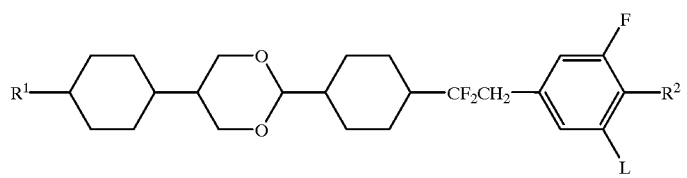

(1f-4)
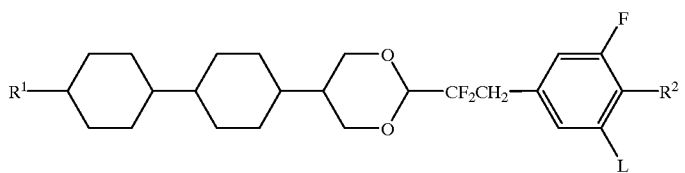
(1f-5)
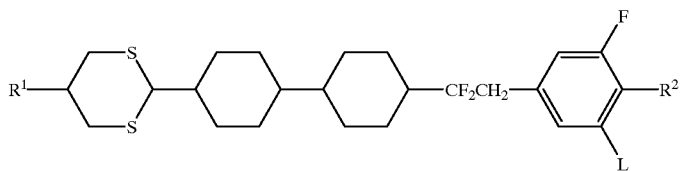
(1f-6)
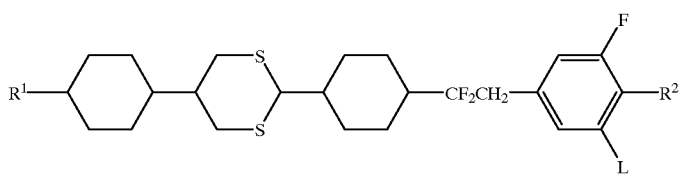
(1f-7)
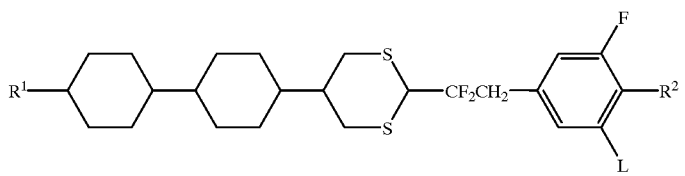
(1f-8)
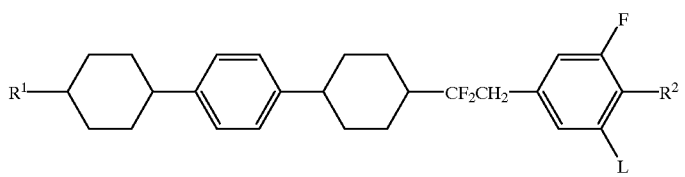
(1f-9)
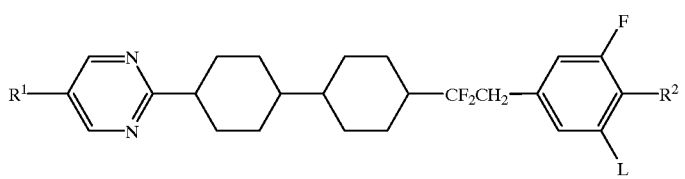
(1f-10)
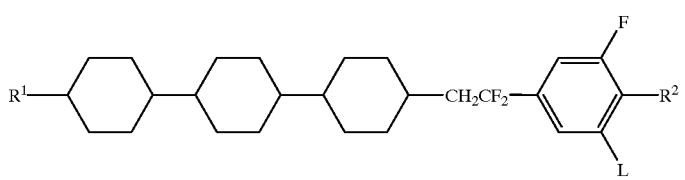

-continued
(1f-11)
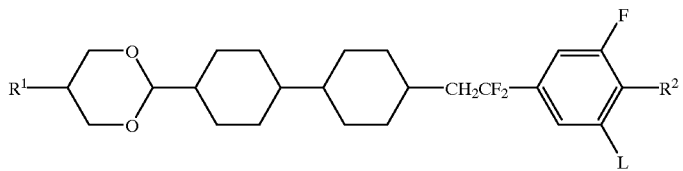
(1f-12)
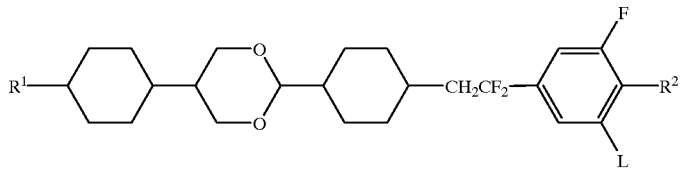
(1f-13)
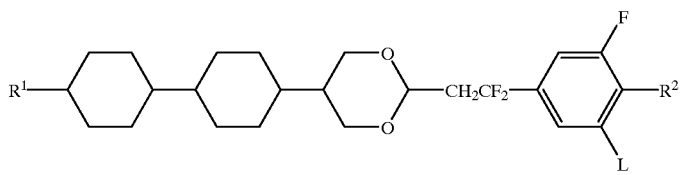
(1f-14)
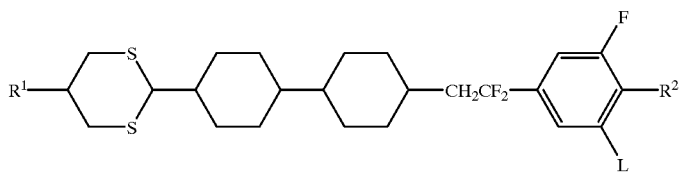
(1f-15)
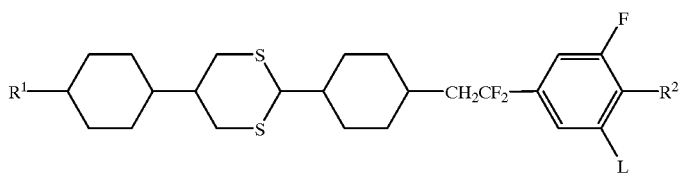
(1f-16)
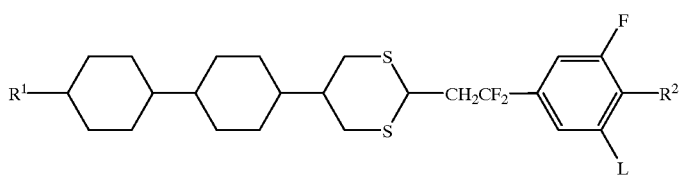
(1f-17)
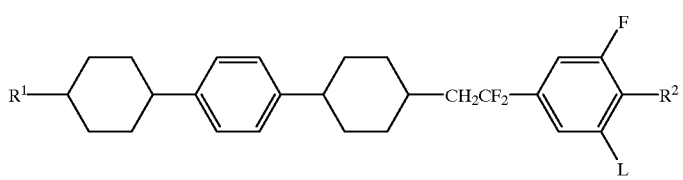

(1f-18)

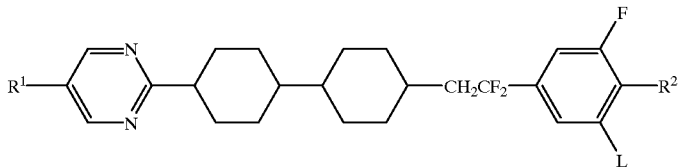

In the above formulas, $R^1$, $R^2$ and L represent the same meaning as mentioned above, and one or more halogen atoms may be replaced on 1,4-phenylene ring.

Of these compounds as more specifically recited above, the compound of formula (1b-1) especially replaced by fluorine provides larger $\Delta\epsilon$ with the increase in the replacement number of fluorine, and further improves the compatibility at low temperature.

The compound of formula (1b-9) wherein L is fluorine and $R^2$ is trifluoromethoxy exhibits large $\Delta\epsilon$ and also improves the compatibility at low temperature.

The liquid crystal composition of the present invention contains at least one of the liquid crystalline compounds represented by formula (1) as a first component. The content of said compound is required to be at least 1% based on the weight of the liquid crystal composition to produce excellent characteristics. Preferred mixing percentage of the first component is 1–50% by weight, more preferably 3–20% by weight.

The liquid crystal compositions of the present invention may be (I) the composition comprising only the first component as mentioned above, but preferably (II) the composition wherein at least one compound selected from the group consisting of the compounds of formulas (2), (3) and (4) is mixed as the second component in addition to the first component; (III) the composition wherein the composition (I) is mixed with at least one compound selected from the group consisting of the compounds of formulas (5) and (6) as the second component; (IV) the composition wherein the composition (II) is mixed with at least one compound selected from the group consisting of the compounds of formulas (7), (8) and (9) as the third component; (V) the composition wherein the composition (III) is mixed with at least one compound selected from the group consisting of the compounds of formulas (7), (8) and (9) as the third component; and (VI) the composition wherein the composition (II) is mixed with at least one compound selected from the group consisting of the compounds of formulas (5) and (6) as the third component and further at least one compound selected from the group consisting of the compounds of formulas (7), (8) and (9) as the fourth component. Further, other components can be mixed suitably. For example, an optically active compound may be added as a helical pitch modifier, and known compounds may be mixed for the purpose of regulating threshold voltage, liquid crystal temperature range, $\Delta n$, $\Delta\epsilon$, viscosity and the like.

Of the second components as mentioned above, suitable examples of the compounds included in the formula (2) can include those represented by the following formulas (2-1) to (2-9). Suitable examples of the compounds included in the formula (3) can include those represented by the following formulas (3-1) to (3-63). Suitable examples of the compounds included in the formula (4) can include those represented by the following formulas (4-1) to (4-15).

(2-1)

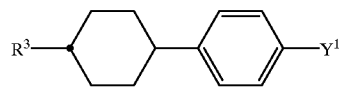

(2-2)

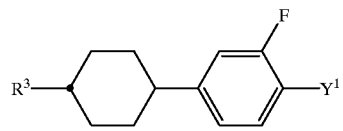

(2-3)

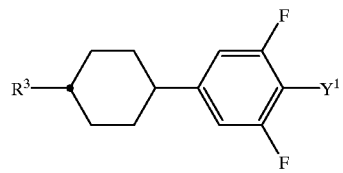

(2-4)
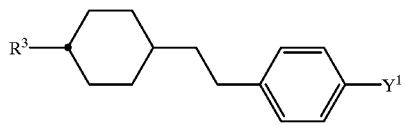
(2-5)
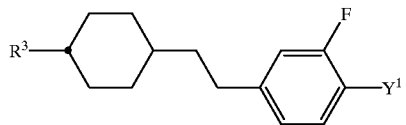
(2-6)
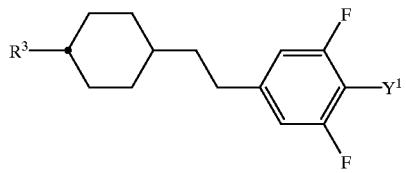
(2-7)
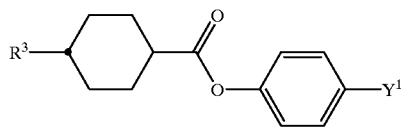
(2-8)
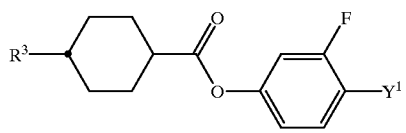
(2-9)
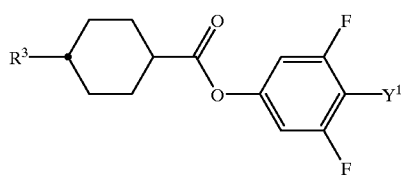
(3-1)
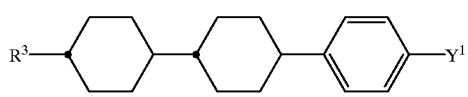
(3-2)
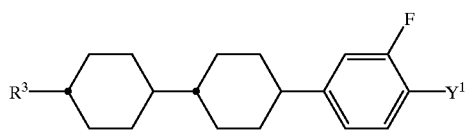
(3-3)
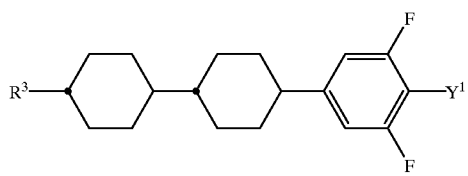

(3-4)
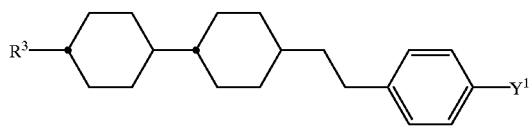
(3-5)
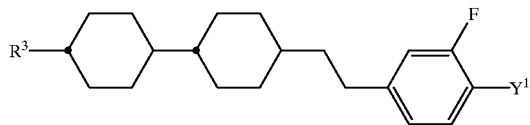
(3-6)
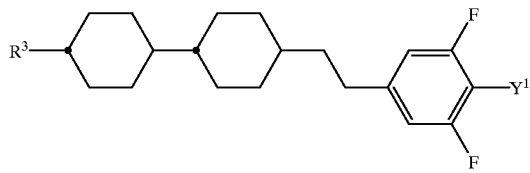
(3-7)
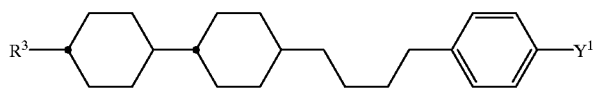
(3-8)
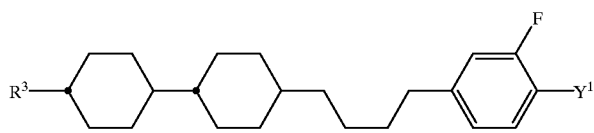
(3-9)
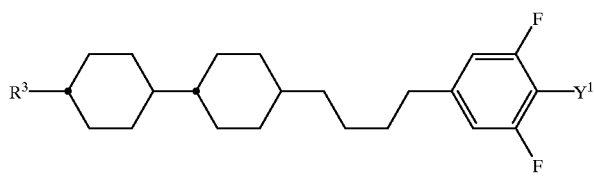
(3-10)
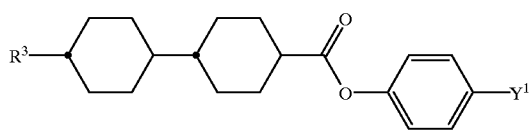
(3-11)
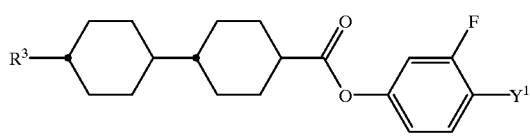
(3-12)
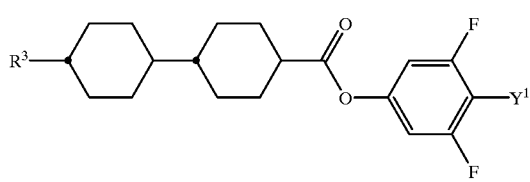

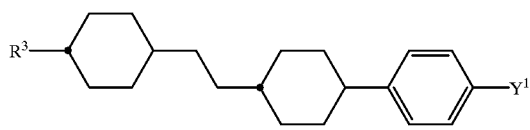
(3-13)
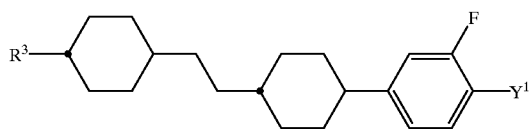
(3-14)
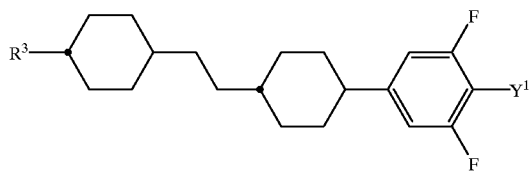
(3-15)
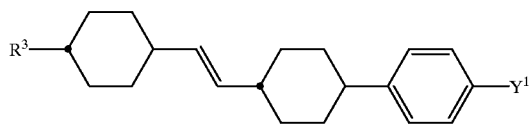
(3-16)
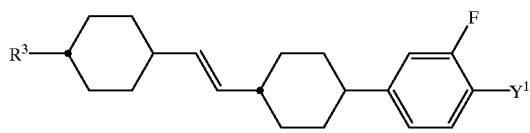
(3-17)
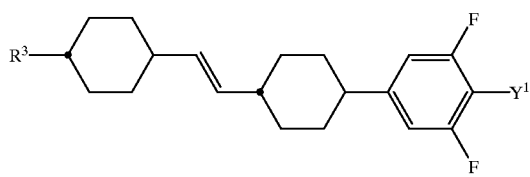
(3-18)
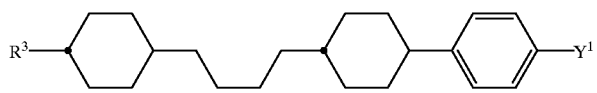
(3-19)
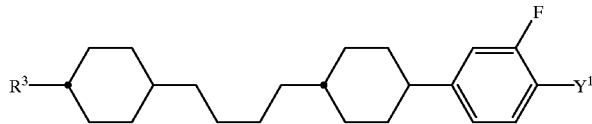
(3-20)
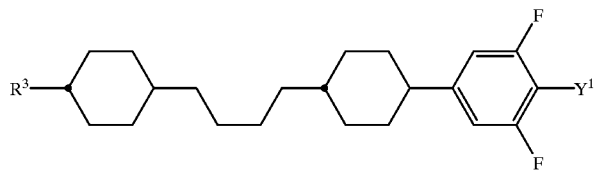
(3-21)

(3-22)
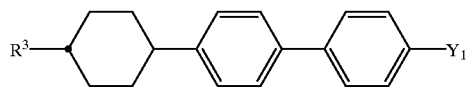
(3-23)
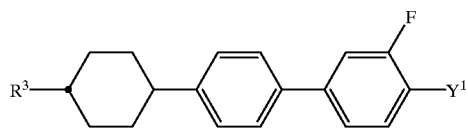
(3-24)
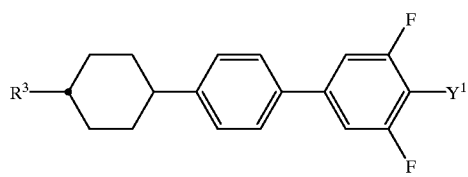
(3-25)
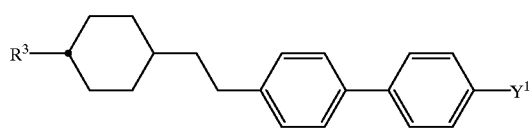
(3-26)
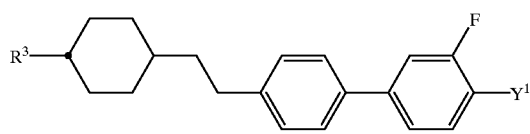
(3-27)
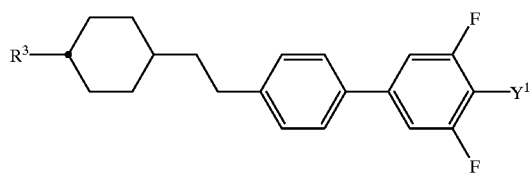
(3-28)
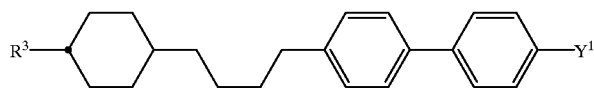
(3-29)
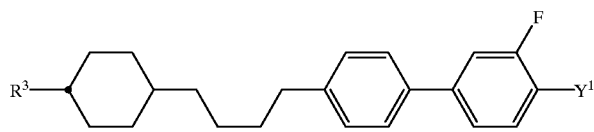
(3-30)
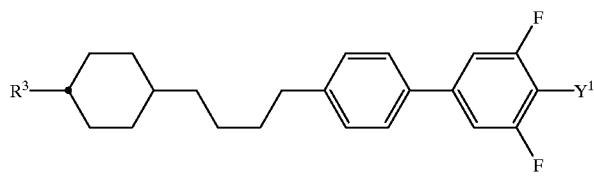

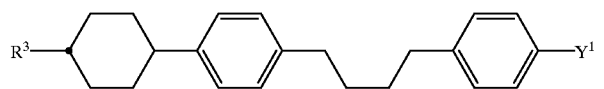
(3-31)
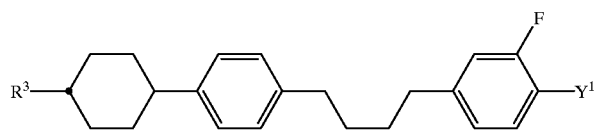
(3-32)
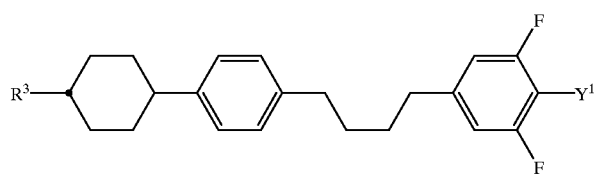
(3-33)
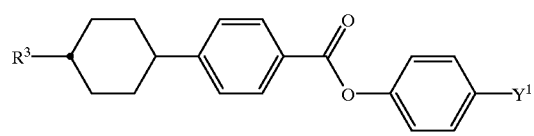
(3-34)
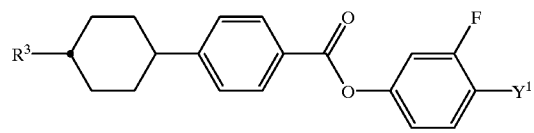
(3-35)
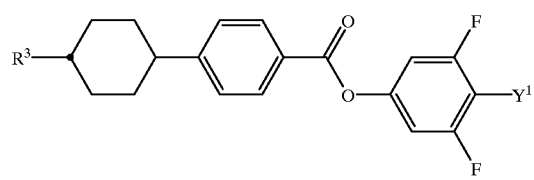
(3-36)
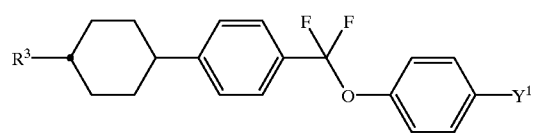
(3-37)
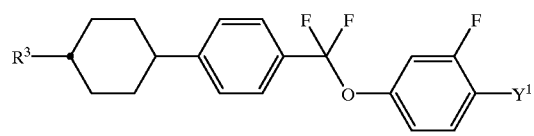
(3-38)
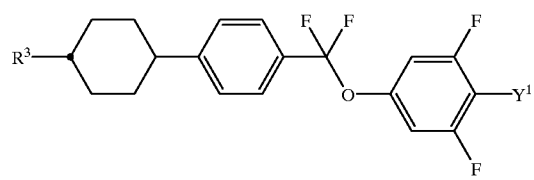
(3-39)

(3-40)
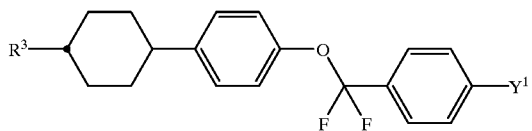
(3-41)
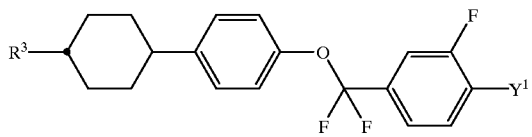
(3-42)
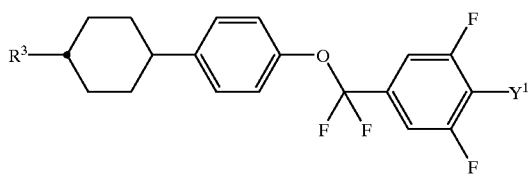
(3-43)
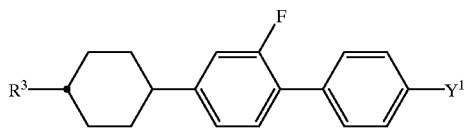
(3-44)
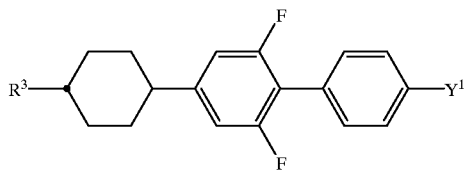
(3-45)
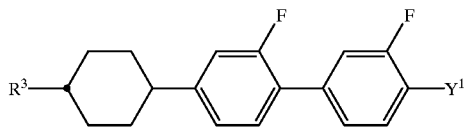
(3-46)
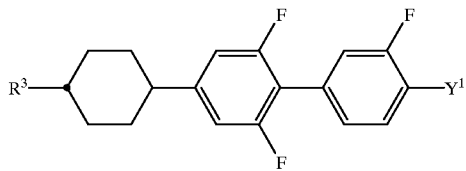
(3-47)
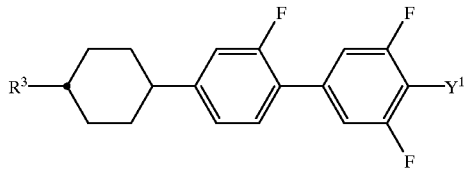

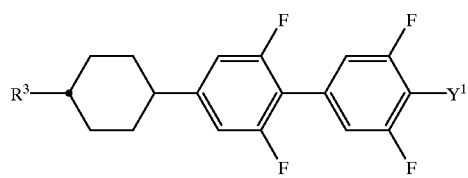
(3-48)
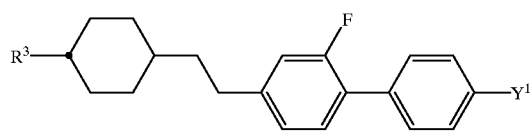
(3-49)
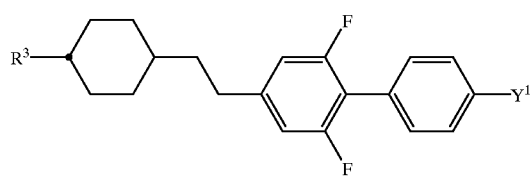
(3-50)
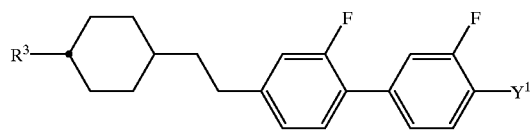
(3-51)
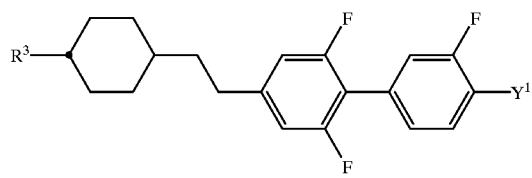
(3-52)
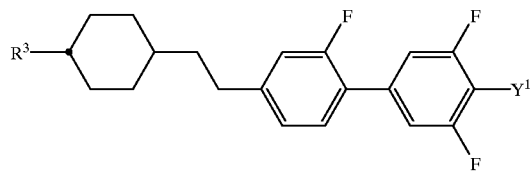
(3-53)
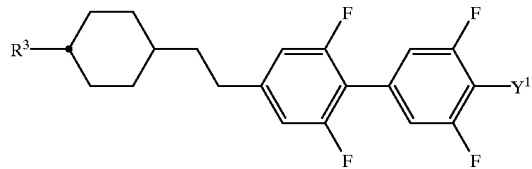
(3-54)
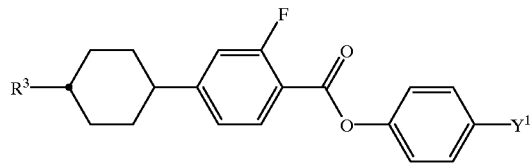
(3-55)

(3-56)
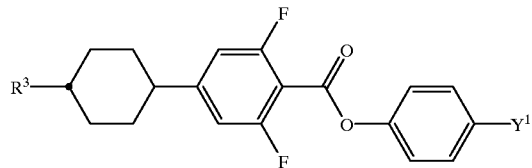
(3-57)
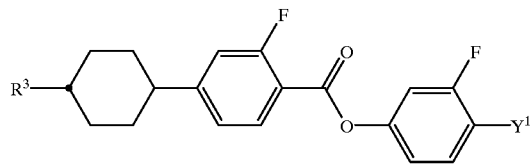
(3-58)
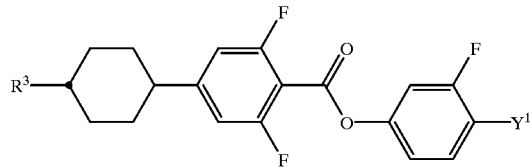
(3-59)
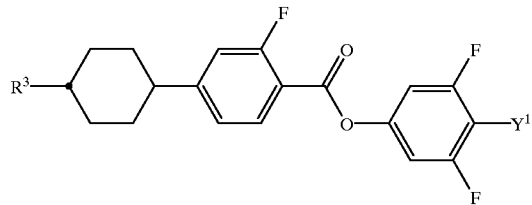
(3-60)
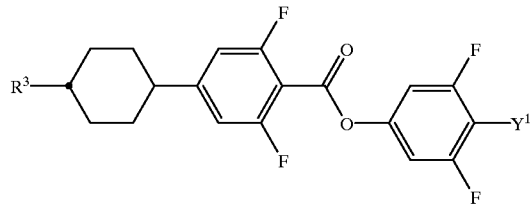
(3-61)
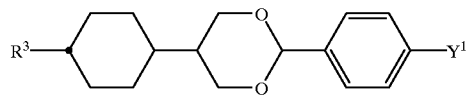
(3-62)
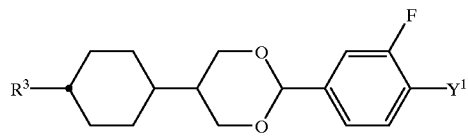

(3-63)
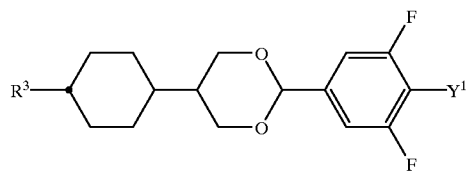
(4-1)
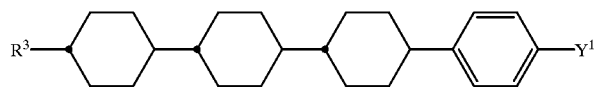
(4-2)
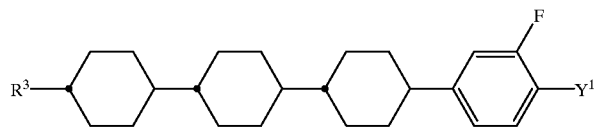
(4-3)
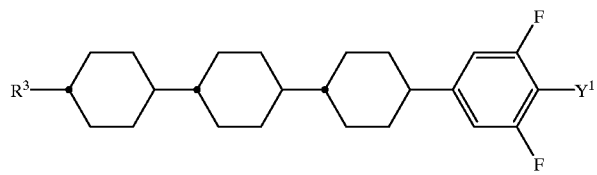
(4-4)
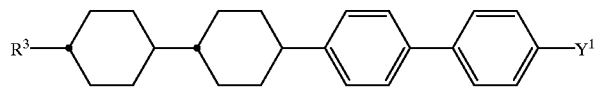
(4-5)
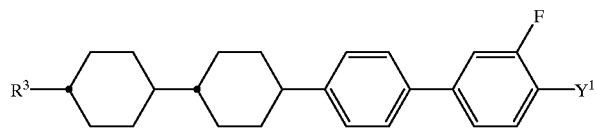
(4-6)
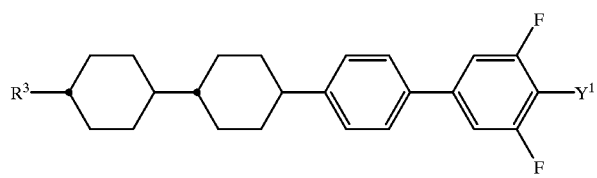
(4-7)
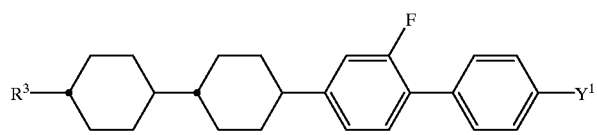
(4-8)
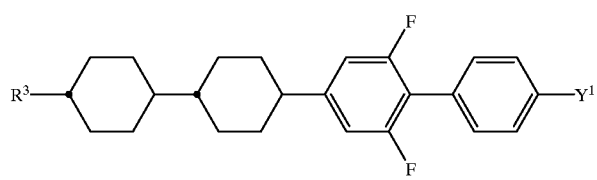

(4-9)
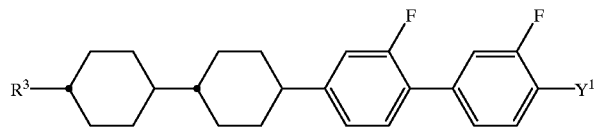
(4-10)
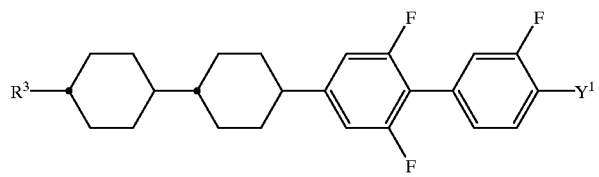
(4-11)
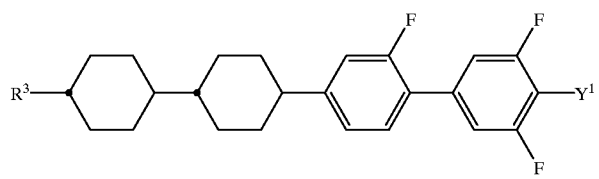
(4-12)
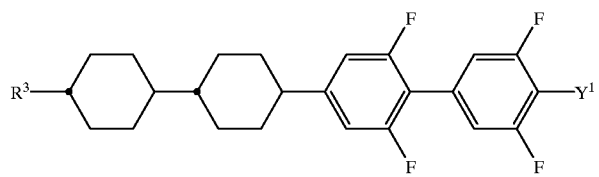
(4-13)
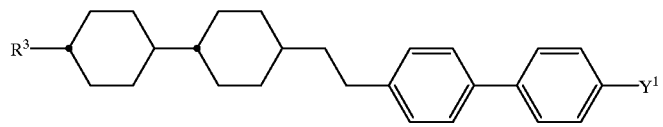
(4-14)
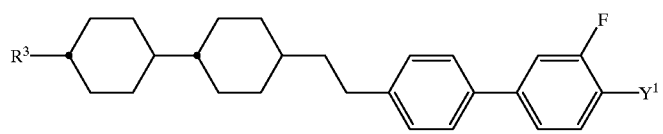
(4-15)
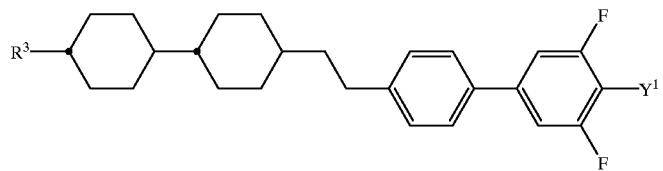

In the above formulas, $R^3$ and $Y^1$ have the meanings as mentioned above.

Of these compounds, the compounds of formulas (2) to (4) have positive $\Delta\epsilon$, excellent thermal and chemical stability, which are useful in the preparation of the liquid crystal composition for TFT which requires high reliability such as high voltage holding rate (large specific resistance).

The mixing percentage of said compounds in the present composition is at least 1% by weight, preferably 10–97% by weight, more preferably 40–95% by weight based on the total weight of the liquid crystal composition, when the liquid crystal composition for TFT is prepared. In that case, the compounds of formulas (7) to (9) may be incorporated.

The compounds of formulas (2) to (4) can be also used in the preparation of liquid crystal composition for STN and TN display mode which drive at low voltage. Preferably, the amount of the compound used in this case is 50% by weight or less based on the total weight of the liquid crystal composition.

Of the compounds as recited above, suitable examples of the compounds included in the formula (5) can include those of the following formulas (5-1) to (5-40), and suitable examples of the compounds included in the formula (6) can include those of the following formulas (6-1) to (6-3).

(5-1)
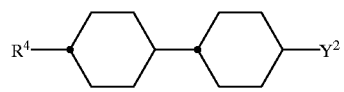

(5-2)
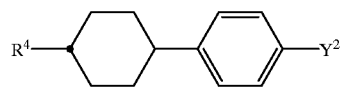

(5-3)
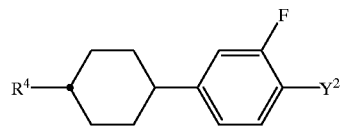

(5-4)
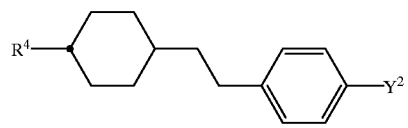

(5-5)
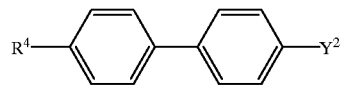

(5-6)
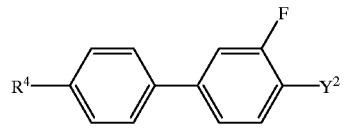

(5-7)
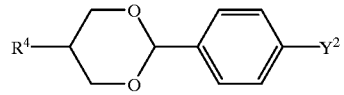

(5-8)
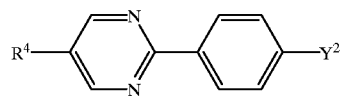

(5-9)
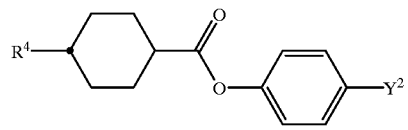
(5-10)
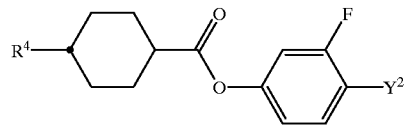
(5-11)
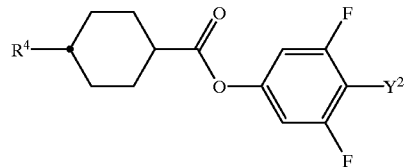
(5-12)
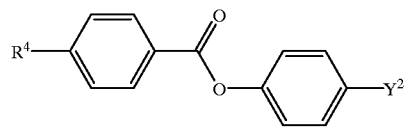
(5-13)
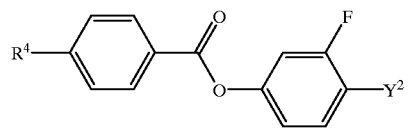
(5-14)
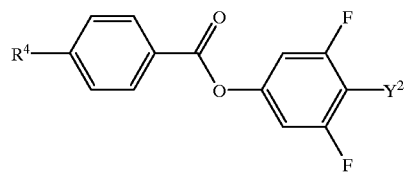
(5-15)
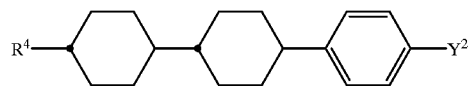
(5-16)
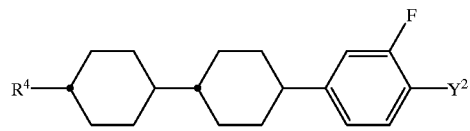
(5-17)
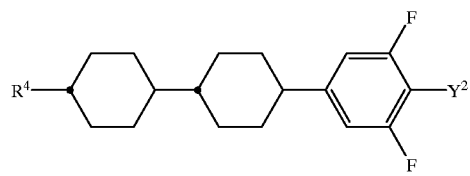

(5-18)
(5-19)
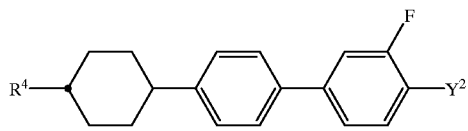
(5-20)
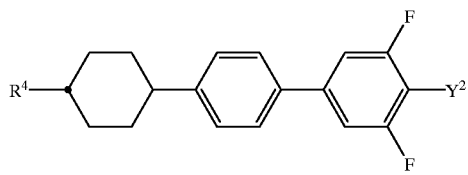
(5-21)
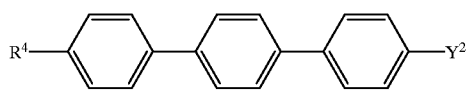
(5-22)
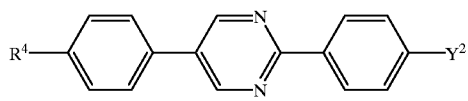
(5-23)
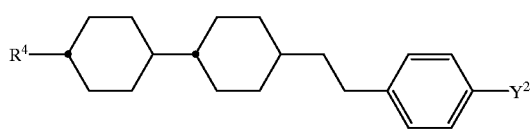
(5-24)
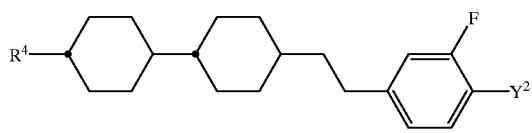
(5-25)
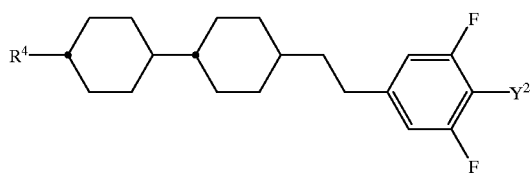
(5-26)
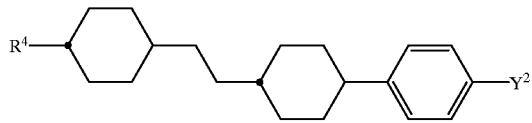

(5-27)
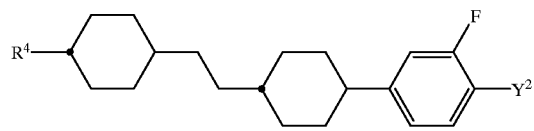
(5-28)
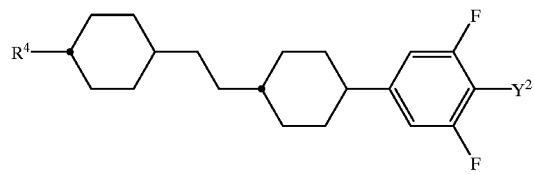
(5-30)
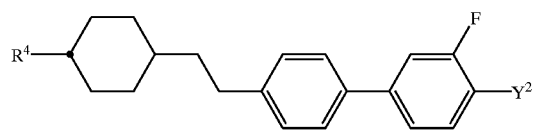
(5-31)
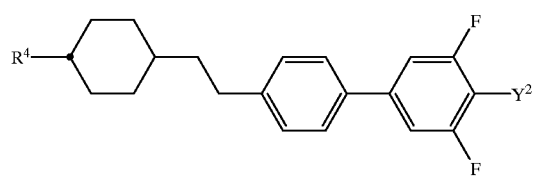
(5-32)
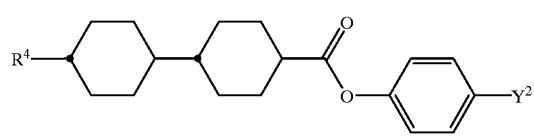
(5-33)
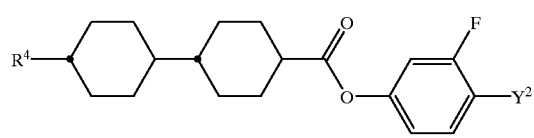
(5-34)
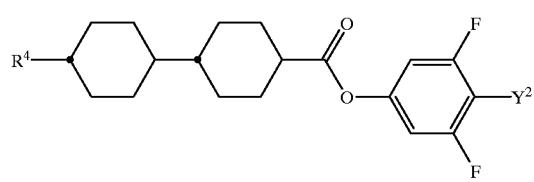
(5-35)
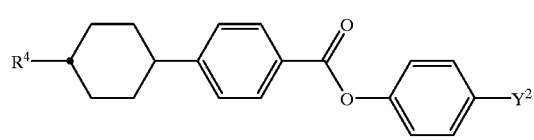

(5-36)
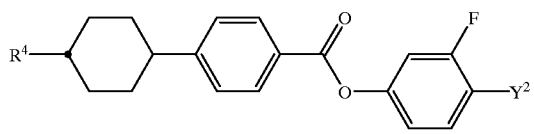

(5-37)
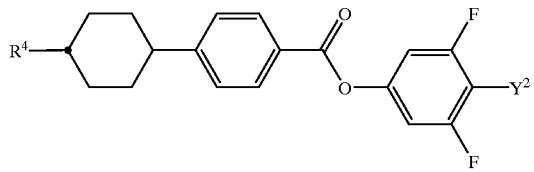

(5-38)
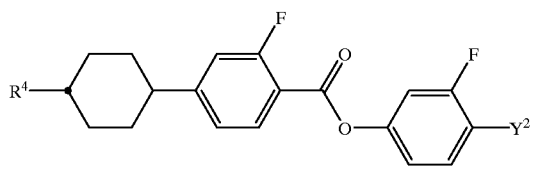

(5-39)
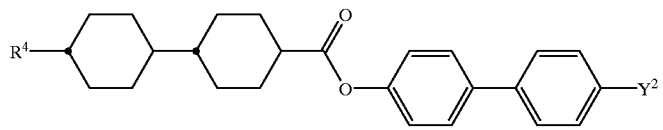

(5-40)
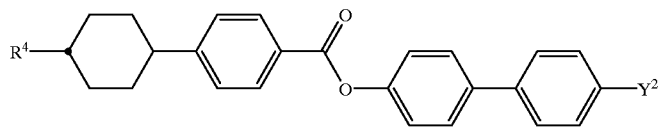

(6-1)
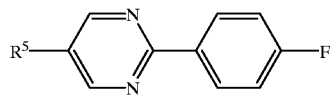

(6-2)
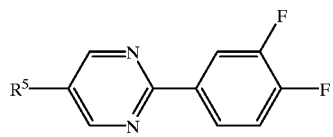

(6-3)
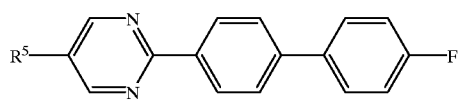

In the above formulae, $R^4$, $R^5$ and $Y^2$ have the meanings as mentioned above.

The compounds of formula (5) or (6) have positive $\Delta\epsilon$ and its large value., and they are used for the purpose of reducing the threshold voltage of the device composed of the resulting composition. Further, these compounds are used for the purpose of improving the steepness in electro-optical characteristic curve, regulating $\Delta n$ and increasing a clear point to broaden a nematic phase range, and they are especially suitable in the preparation of liquid crystal composition for liquid display device driving at low voltage.

These compounds can make the threshold voltage of the liquid crystal composition lower according to an increase in the amount of the compound used, but bringing about an increase in viscosity. As long as the viscosity of the liquid crystal composition satisfies the required physical value, larger amount of the compound used is advantageous from a viewpoint of the driving at low voltage.

Under such circumstances, the amount of the above compound used is at least 1% by weight based on the total weight of the liquid crystal composition, preferably 10–97% by weight, more preferably 40–95% by weight of the resulting composition. Of the compounds as recited above, suitable examples of the compounds included in the formula (7) can include those of the following formulas (7-1) to (7-11), suitable examples of the compounds included in the formula (8) can include those of the following formulas (8-1) to (8-18), and suitable examples of the compounds included in the formula (9) can include those of the following formulas (9-1) to (9-6).

(7-1)
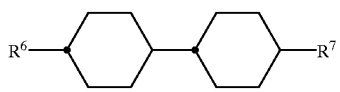

(7-2)
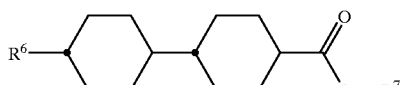

(7-3)
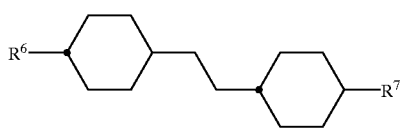

(7-4)
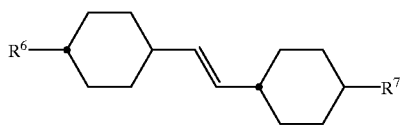

(7-5)
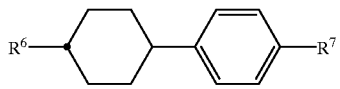

(7-6)
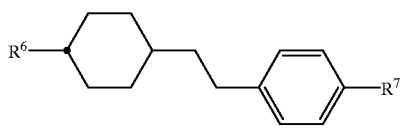

(7-7)
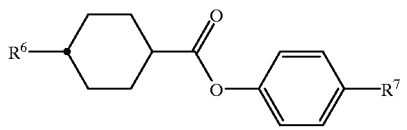

(7-8)
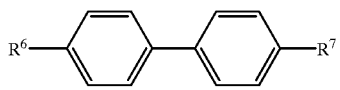

(7-9)
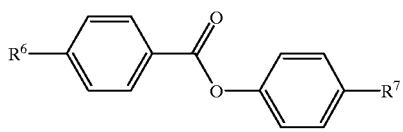

(7-10)
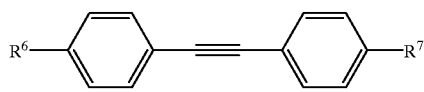
(7-11)
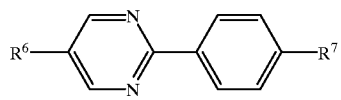
(8-1)
(8-2)
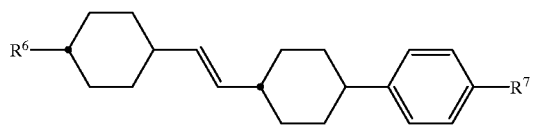
(8-3)
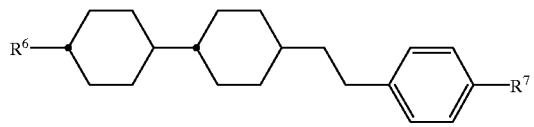
(8-4)
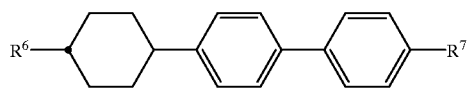
(8-5)
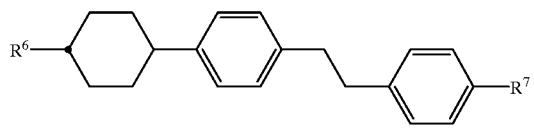
(8-6)
(8-7)
(8-8)
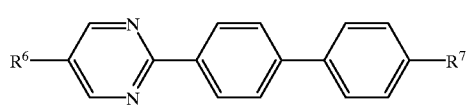
(8-9)
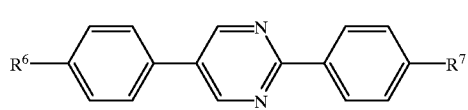

(8-10)
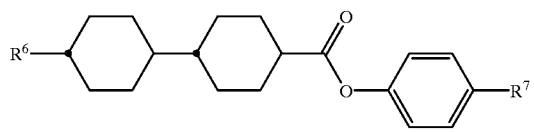
(8-11)
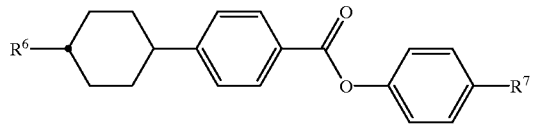
(8-12)
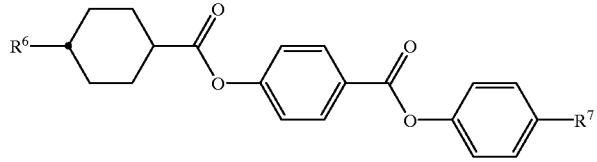
(8-13)
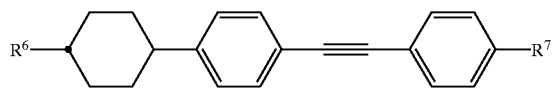
(8-14)
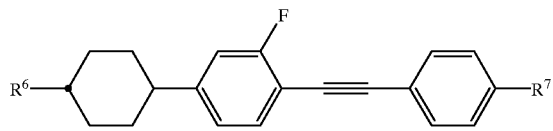
(8-15)
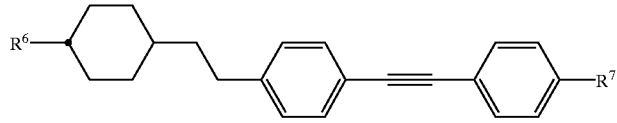
(8-16)
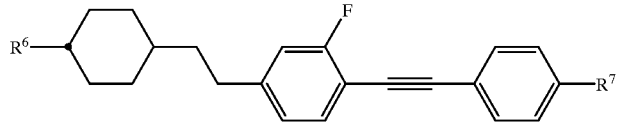
(8-17)
(8-18)
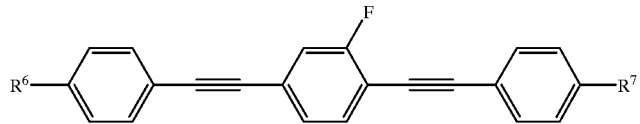
(9-1)
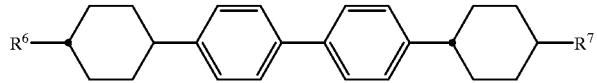

-continued (9-2)
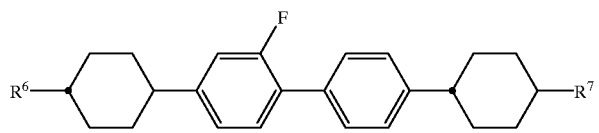

(9-3)
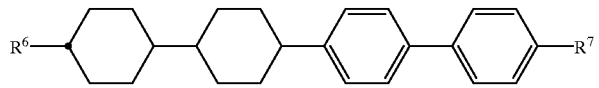

(9-4)
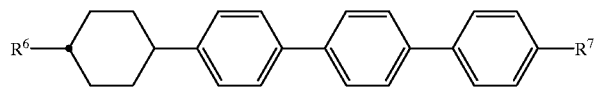

(9-5)
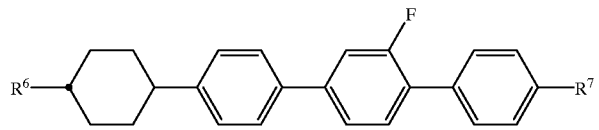

(9-6)
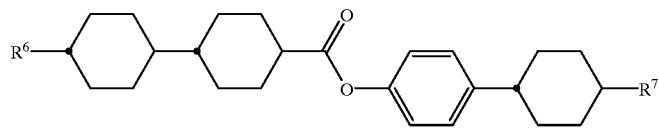

In the above formulas, $R^6$ and $R^7$ have the same meanings as mentioned above.

The compounds of formulas (7) to (9) are small and close to zero in the absolute value of $\Delta\epsilon$. Of these compounds, the compound of formula (7) is used mainly for the adjustment of viscosity or $\Delta n$ of the resulting liquid crystal composition. The compounds of formulas (8) and (9) are used for increasing a clear point of the resulting composition to broaden a nematic phase range of the composition or adjusting $\Delta n$.

These compounds can make the threshold voltage of the liquid crystal composition higher according to an increase in the amount of the compound used, but reducing the viscosity. As long as the threshold voltage of the liquid crystal composition satisfies the required physical value, larger amount of the compound used is desirable.

Under such circumstances, suitable amount of the above compound used is not more than 40% by weight, preferably not more than 35% by weight based on the total weight of the liquid crystal composition, when high reliability is required as in the liquid crystal composition for TFT. When low threshold voltage is required as in the liquid crystal composition for STN and TN display modes, suitable amount of the above compound used is not more than 70% by weight, preferably not more than 60% by weight based on the total weight of the liquid crystal composition.

Of other components in the composition of the present invention, an optically active compound is added for the purpose of causing a helical structure of liquid crystal composition to adjust necessary twist angle, thereby preventing a reverse twist, except for a special case, for example the case where the component is used in the liquid crystal composition for OCB (Optically Compensated Birefringence) mode.

The optically active compound is extensively selected from known compounds as far as the above purpose is achieved. Preferable examples of optically active compounds can include those of the following formulas (Op-1) to (Op-8).

(Op-1)
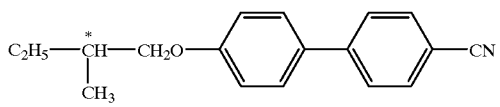

(Op-2)
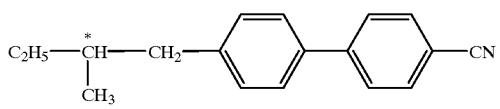

(Op-3)
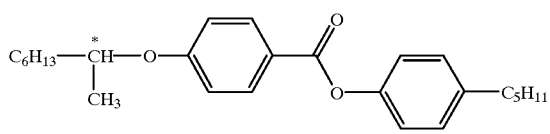

(Op-4)

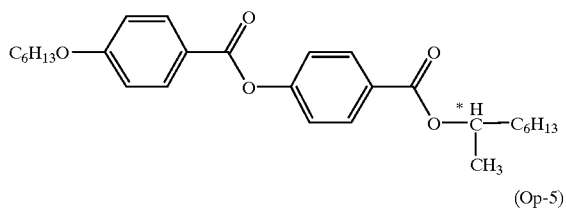

(Op-5)

(Op-6)

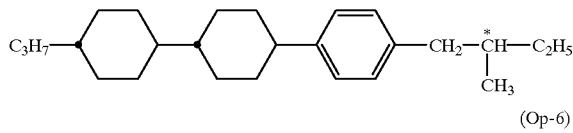

(Op-7)

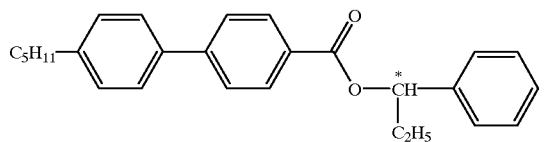

(Op-8)

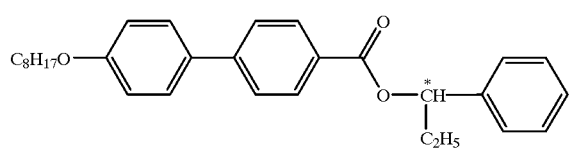

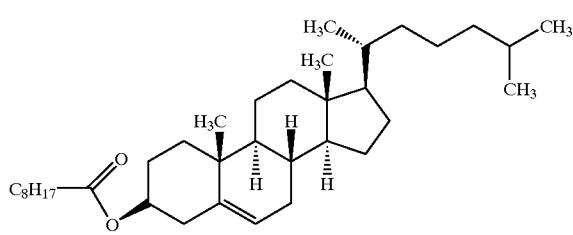

By addition of these optically active compounds, the pitch length of twist in the resulting liquid crystal composition is adjusted. Preferably, the pitch length of twist is adjusted in the range of 6 to 20 μm for the liquid crystal composition for STN and in the range of 1.5 to 4 μm for the composition for bistable TN mode. In that case, two or more optically active compounds may be added for the purpose of adjusting a temperature dependence of pitch length.

The liquid crystal composition of the present invention can be used in the display device of either field-effect or current-effect type. For Example, it can be used in the display devices of a twisted nematic mode, a twisted nematic mode in combination with an active matrix system, a supertwisted nematic mode and a field-controlled birefringent mode. Further, the present composition can be used as a liquid crystal composition for guest-host (GH) mode by incorporating therein diachronic dyes such as merocyanines, styryls, azo, azomethines, azoxy, quinophthalones, anthraquinones, tetrazines or the like. In addition, it can be used in the display devices which include a device wherein an encapsulated liquid crystal composition is dispersed in a polymer and a device wherein a liquid crystal composition is present in a spongy polymer.

The compounds of the present invention represented by formula (1) can be prepared by selecting usual methods in a synthetic organic chemistry and combining them. For example, methods described in "Organic Synthesis" (John Wiley & Sons, Inc.), "Organic Reactions" (John Wiley & Sons, Inc.), "Jitsuken Kagaku Kouza" (Maruzen Co. Ltd.) or the like may be selected suitably and combined.

For example, Wittig reagent (10) described in "Organic Reactions, vol. 14, page 270" and a ylid compound prepared from a base such as potassium-t-butoxide and alkyl lithium are reacted with cyclohexanone derivative (11) to prepare olefin derivative (12). Subsequently, olefin derivative (12) is reacted with 9-borabicyclo[3.3.1]nonane (abbreviated hereafter as 9-BBN), and followed by oxidation to prepare alcohol derivative (13) which is then converted to ketone derivative (14), for example by Swern oxidation described in "Jitsuken Kagaku Kouza", 4 edn. Vol. 23, page 299. The ketone (14) can be fluorinated with diethylaminosulfurtrifluoride (abbreviated hereafter as "DAST") to prepare a target compound of formula (1) (See, the following Scheme 1);

Alternatively, Grignard reagent prepared from alkyl halide derivative (15) is reacted with aldehyde derivative (16) to prepare alcohol derivative (17) which can be then oxidized and fluorinated in the same manner as mentioned above to prepare a target compound of formula (1) (See, the following Scheme 2).

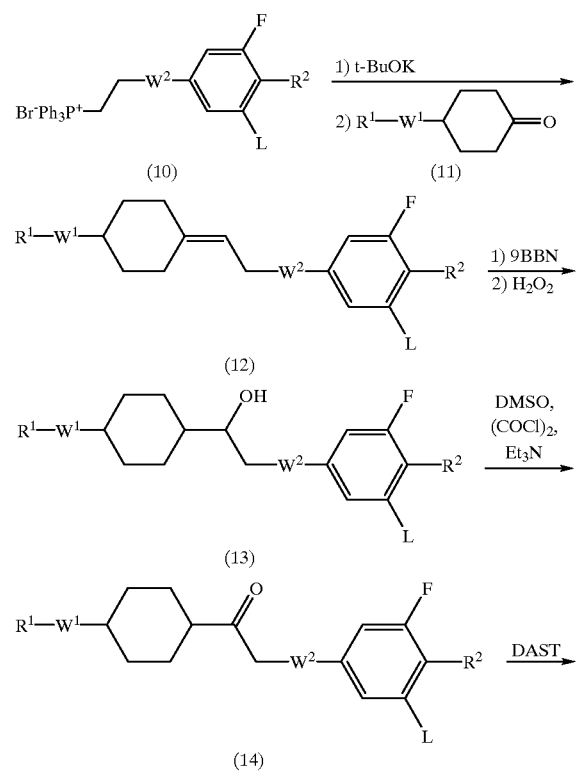

Scheme 2

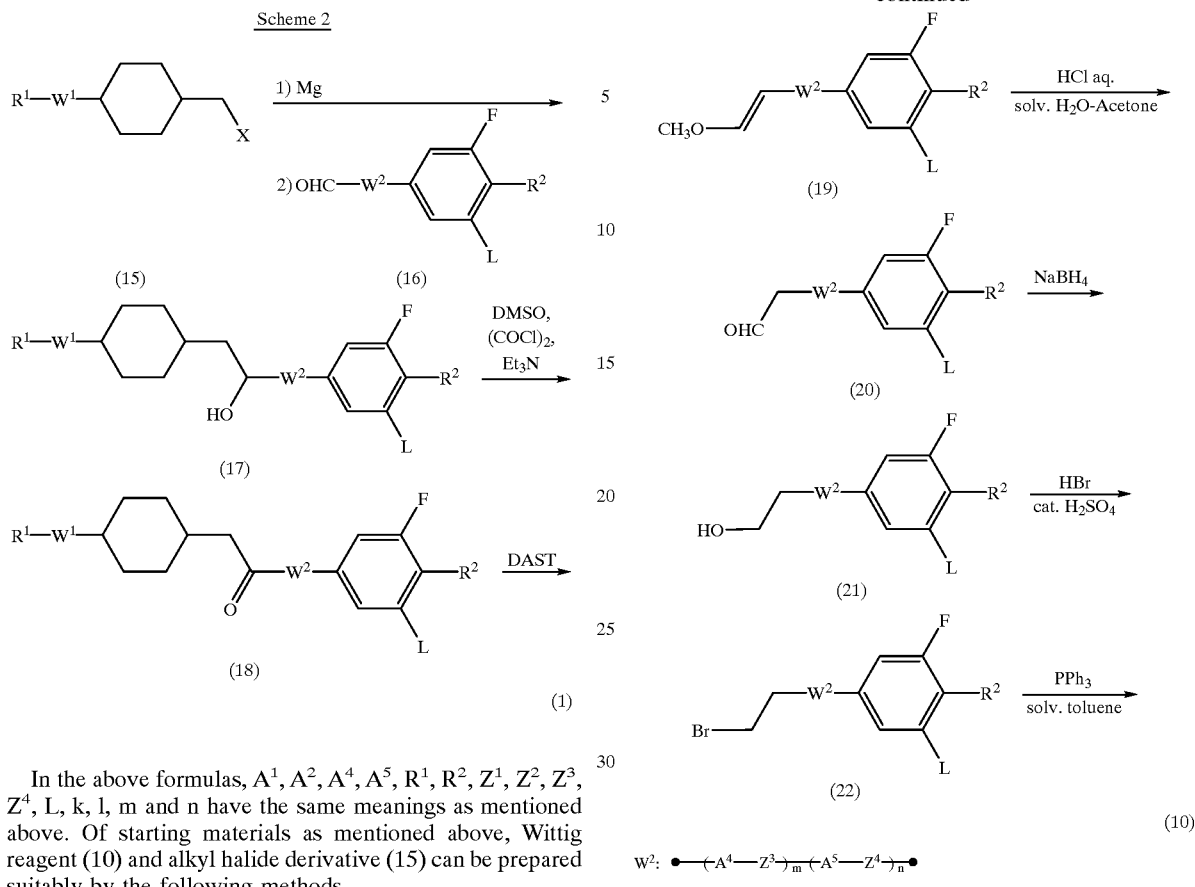

In the above formulas, $A^1, A^2, A^4, A^5, R^1, R^2, Z^1, Z^2, Z^3, Z^4$, L, k, l, m and n have the same meanings as mentioned above. Of starting materials as mentioned above, Wittig reagent (10) and alkyl halide derivative (15) can be prepared suitably by the following methods.

Preparation of Wittig Reagent (10)

Aldehyde derivative (16) is reacted with a ylid compound prepared from methoxymethyltriphenylphosphonium chloride and potassium-t-butoxide to prepare olefin derivative (19). This derivative is hydrolyzed to aldehyde derivative (20) which is then reduced to alcohol derivative (21). This derivative can be halogenated to alkyl halide derivative (22), thus leading to Wittig reagent (10)(See, the following Scheme 3).

Alkyl Halide Derivative (15-1)

Olefin derivative (23) is prepared from cyclohexanone derivative (11) in accordance with conventional method. Olefin derivative (23) is hydrolyzed with an acid such as hydrochloric acid to aldehyde derivative (24) which is then reduced with sodium borohydride to alcohol derivative (25). This derivative can be halogenated with hydrobromic acid to alkyl halide derivative (15-1)(See, the following Scheme 4).

Scheme 3

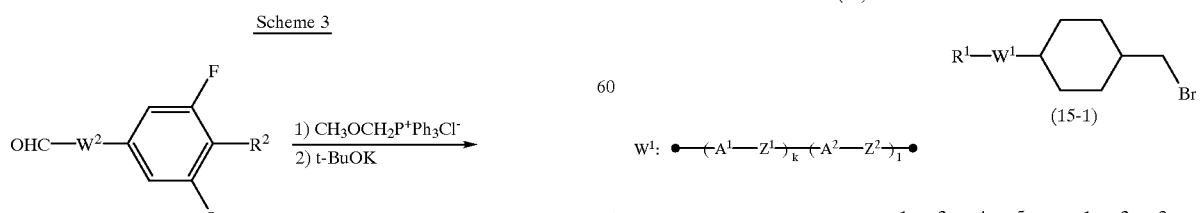

Scheme 4

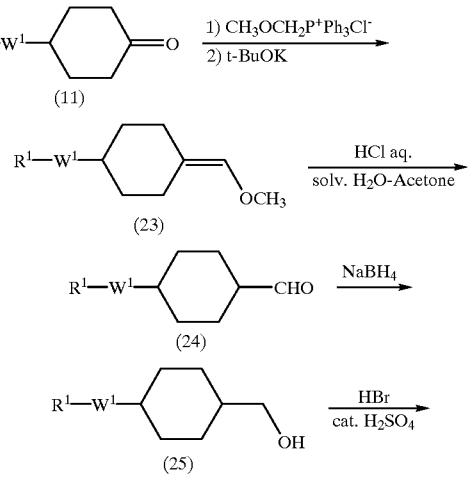

In the above formulas, $A^1, A^2, A^4, A^5, L, Z^1, Z^2, Z^3, Z^4$ $R^1$ $R^2$, k, l, m and n have the same meanings as mentioned above.

EXAMPLES

The present invention is further illustrated by the following non-limiting examples. In the examples, Cr represents crystal, N represents a nematic phase, S stands for smectic phase, Iso stands for isotropic phase, and the unit of the phase transition temperature is indicated by ° C. In the data of 1H-NMR, s stands for singlet, d stands for doublet, t stands for triplet, m stands for multiplet, and J stands for coupling constant (Hz). All percentages are based on weight, unless otherwise stated.

Example 1

Preparation of 1,1-difluoro-1-[trans-4-(trans-4-pentylcyclohexyl)cyclohexyl]-2-(3,4-difluorophenyl)ethane (Compound No. 46 of formula (1) wherein k=l, l=m=n=0, Q is —$CF_2CH_2$—, $R^2$=F, L=H, $A^1$ and $A^2$ are trans-1,4-cyclohexylene, $Z^1$ is a single bond, $R^1=C_5H_{11}$)

Preparation of 1-Methoxy-2-(3,4-difluorophenyl)ethane

Into a 2 liter three-necked flask equipped with a stirrer, a thermometer, a dropping funnel and a nitrogen gas tube, 133.7 g (390 mmol) of methoxymethyltriphenyl phosphonium chloride were charged in a nitrogen atmosphere and dried, and 450 ml of THF were added. The mixture was cooled to −30° C., 43.76 g (390 mmol) of potassium-t-butoxide were added and the mixture was stirred for 1 hr. To the mixture, a solution of 42.63 g (300 mmol) of 3,4-difluorobenzaldehyde in 150 ml of THF was added dropwise over a period of one and a half hours. The mixture was stirred as such over night and raised to room temperature. Water and heptane were added, the precipitate was filtered through Celite, and an organic layer and an aqueous layer were separated. The aqueous layer was extracted with heptane, an extract combined with the organic layer was washed with water, and the organic layer was dried over anhydrous magnesium sulfate. A solvent was distilled away from the solution, and the solution was condensed. The concentrate was purified by column chromatography (elution solvent: mixed solvent of toluene and heptane), the eluate was further purified by vacuum distillation to obtain 46.70 g of the title compound (91%, bp 98–100° C./15 Torr., cis:trans=1:1) as oily product.

Preparation of (3,4-Difluorophenyl)acetaldehyde

Into a 1 liter three-necked flask equipped with a stirrer and a condenser, 46.70 g (274 mmol) of 1-methoxy-2-(3,4-difluorophenyl)ethane, 685 ml of acetone and 114 ml of 3M-hydrochloric acid were charged and the mixture was heated under reflux for 2 hrs. Acetone was distilled off, and water and ether were added. An organic layer and an aqueous layer were separated, the aqueous layer was extracted with ether, the extract combined with the organic layer was washed with a saturated aqueous solution of sodium hydrogen carbonate, and dried over anhydrous magnesium sulfate. The desiccating agent was filtered off, the solvent distilled off, the solution condensed and purified by vacuum distillation to obtain 33.29 g (78%, bp 98–100° C./16 Torr.).

Preparation of 2-(3,4-Difluorophenyl)ethanol

Into a 1 liter three-necked flask equipped with a stirrer, 33.29 g (213 mmol) of (3,4-difluorophenyl) acetaldehyde and 426 ml of ethanol were charged, to which 8.85 g (234 mmol) of sodium borohydride were added, and the mixture was stirred overnight. Ethanol was distilled off, and 1N hydrochloric acid and ether were added. An organic layer and an aqueous layer were separated, the aqueous layer was extracted with ether, the extract combined with the organic layer was dried over anhydrous magnesium sulfate. The desiccating agent was filtered off, the solvent was distilled off and condensed, the concentrate was purified by vacuum distillation to obtain 17.59 g (52%, bp 110–121° C./16–22 Torr.) of the title compound as oily product.

Preparation of 3,4-Difluorophenethylbromide 17.59 g (111 mmol) of 2-(3,4-difluorophenyl)ethanol, 16 ml (137 mmol) of hydrogen bromide, 6.8 ml (234 mmol) of conc. sulfuric acid were added in the order, and the mixture was heated under reflux for 3 hrs. The reaction mixture was poured onto an ice-bath, an organic layer and an aqueous layer were separated, the aqueous layer was extracted with ether, the extract combined with the organic layer was washed with a saturated aqueous solution of sodium hydrogen carbonate, and dried over anhydrous magnesium sulfate. The solvent was distilled off, the solution condensed and purified by vacuum distillation to obtain 21.96 g (bp 68–70° C./2–4 Torr.) of oily product. The oily product was purified by column chromatography (elution solvent: hexane:ethyl acetate=3:1), the eluate was further purified by vacuum distillation to obtain 19.79 g of the title compound (81%, bp 73–75° C./4 Torr.) as oily product.

Preparation of (3,4-Difluorophenyl) ethyltriphenylphosphonium Bromide

A mixture of 19.67 g (89 mmol) of 3,4-difluoro-phenethyl bromide, 28.07 g (107 mmol) of triphenyl phosphine and 134 ml of toluene was heated under reflux for 36 hrs. After cooling, the crystal was washed by decantation with toluene and dried in vacuo, while ice-cooling.

Preparation of 1-(3,4-Difluorophenyl)-2-[4-(trans-4-pentylcyclohexyl)cyclohexylidene]ethane 43.01 g (89 mmol) of (3,4-difluorophenyl) ethyltriphenylphosphonium bromide were charged into a 300 ml three-necked flask in a nitrogen atomosphere and dried, and 74 ml of THF were added. The mixture was cooled to −30° C, a solution of 9.99 g (89 mmol) of potassium-t-butoxide in 70 ml of THF was added dropwise over a period of 15 minutes and the mixture was stirred for 1 hr. To this mixture was added dropwise a solution of 18.53 g (74 mmol) of 4-(trans-4-pentylcyclohexyl)cyclohexanone in 74 ml of THF over a period of 25 minutes. The mixture was stirred as such overnight and raised to room temperature. Water and toluene were added, the precipitate was filtered through Celite, and an organic layer and an aqueous layer were separated. The aqueous layer was extracted with toluene, an extract combined with the organic layer was washed with water, and dried over anhydrous magnesium sulfate. Triphenylphosphine oxide in the extract was filtered off, the solvent was distilled off and the solution was condensed. The concentrate was purified by column chromatography (elution solvent: heptane:ethyl acetate=20:1) to obtain 19.67 g of the eluate. Recrystallization at −30° C. from 50 ml of heptane-trace amount of solmix gave 14.31 g of the title compound (52%, Cr 38.4–38.5 Iso).

1H-NMR (δ ppm) 0.8–2.7 (m, 30H), 3.3 (d, 2H, J=7.25 Hz), 5.2 (t, 1H, J=7.25 Hz) 6.8–7.2 (m, 3H).

Preparation of 1-Hydroxy-1-[trans-4-(trans-4-pentylcyclohexyl)cyclohexyl]-2-(3,4-difluorophenyl)ethane To a solution of 11.24 g (30 mmol) of 1-(3,4-difluorophenyl)-2-[4-(trans-4-pentylcyclohexyl)cyclohexylidene]ethane in 30 ml of THF were added 300 ml (150 mmol) of 0.5 M-9-BBN (THF solution) over a period of 35 minutes, at room temperature under stirring in an argon atmosphere and the mixture was stirred as such overnight. 90 ml of ethanol and 30 ml of an aqueous 6M-NaOH solution were added, and 60 ml of an aqueous 30% $H_2O_2$ solution were added over a period of 40 minutes (during this period, refluxed spontaneously). The mixture was stirred at 50° C. for 1 hr. After cooling, 180 ml of an aqueous 1M-HCl solution, water and toluene were added and the precipitate was filtered through Celite. An organic layer and an aqueous layer were separated, the aqueous layer was extracted with toluene, an extract combined with the organic layer was washed with an aqueous 5% $Na_2S_2O_3$ solution, and dried over anhydrous magnesium sulfate. The solvent was distilled off and the solution was condensed. The concentrate was purified by column chromatography (elution solvent: heptane:ethyl acetate=5:1). The eluate was recrystalized from 50 ml of heptane-5 ml of solmix to obtain 6.86 g of the title compound (58%, Cr 108.4–109.2 N 143.1–144.1 Iso).

$^1$H-NMR (δ ppm) 0.6–2.1 (m, 32H), 2.4–2.9 (m, 2H), 3.4–3.6 (m, 1H), 6.8–7.2 (m, 3 H).

Preparation of 1-oxo-1-[trans-4-(trans-4-Pentylcyclohexyl) cyclohexyl]-2-(3,4-difluorophenyl)ethane 2.34 ml (33 mmol) of dimethyl sulfoxide were added at −60° under stirring in an argon atomosphere to a solution of 1.44 ml (16.5 mmol) of oxalyl chloride in 38 ml of methylene chloride and then a solution of 5.89 g (15 mmol) of 1-hydroxy-1-[trans-4-(trans-4-pentylcyclohexyl)cyclohexyl]-2-(3,4-difluorophenyl)ethane in 160 ml of methylene chloride was added over a period of 1 hr. After 15 minutes, 10.45 ml (75 mmol) of triethylamine were added and stirred for 2 hours and 50 minutes, and gradually raised to room temperature. 75 ml of water were added to stop the reaction. An organic layer and an aqueous layer were separated, the aqueous layer was extracted with methylene chloride, an extract combined with the organic layer was dried over anhydrous magnesium sulfate. The solvent was distilled off and the concentrate was purified by column chromatography (elution solvent: toluene:heptane=2:1). Further, the eluate was recrystallized from heptane-solmix and toluene-solmix to obtain 4.83 g of the title compound (82%, Cr 111.9–112.8 Iso).

$^1$H-NMR (δ ppm) 0.4–2.5 (m, 31H), 3.7 (s, 2H), 6.8–7.2 (m, 3H) Preparation of 1,1-difluoro-1-[trans-4-(trans-4-pentylcyclohexyl)cyclohexyl]-2-(3,4-difluorophenyl)ethane 6.05 g (15.5 mmol) of 1-oxo-1-[trans-4-(trans-4-pentylcyclohexyl)cyclohexyl]-2-(3,4-difluorophenyl)ethane and a solution of 25 g (155 mmol) of DAST in 47 ml of dimethoxyethane were stirred at room temperature for 8 hrs. A reaction mixture was diluted about three times with ether, then a saturated aqueous sodium hydrogencarbonate solution was gradually added to stop the reaction. An organic layer and an aqueous layer were separated, the aqueous layer was extracted with ether, an extract combined with the organic layer was dried over anhydrous magnesium sulfate. The solvent was distilled off, the solution was condensed and the concentrate was purified by column chromatography (elution solvent: heptane). Further, the eluate was recrystallized from heptane to obtain 0.55 g of the title compound (9%, Cr 84.1–85.0, N 95.3–95.4 Iso).

$^1$H-NMR (δ ppm) 0.8–1.8 (m, 31H), 3.0 (t, 2H, J=17.1 Hz), 6.9–7.0 (m, 1H), 7.1–7.2 (m, 2H).

Example 2

Preparation of 1,1-Difluoro-1-(3,5-difluoro-4-trifluoromethoxyphenyl)-2-[trans-4-(trans-4-propylcyclohexyl)cyclohexyl]ethane (Compound No. 73 of formula (1) wherein k=1, l=m=n=0, $A^1$ and $A^3$ are trans-1,4-cyclohexylene, Q is —$CH_2CF_2$—, $R^2$=$OCF_3$, L=F, $Z^1$ is a single bond, $R^1$=$C_3H_7$)

In accordance with Scheme 2 as shown above, the ketone derivative (18) was prepared from the alkyl halide derivative (15). This ketone derivative was used to prepare 1.3 g of the title compound according to the process illustrated in Example 1.

Example 3

Preparation of 1,1-Difluoro-1-[trans-4-(5-pentyl-1,3-dioxane-2-yl)cyclohexyl]-2-(3,4-difluorophenyl)ethane (Compound No. 63 of formula (1) wherein k=1, l=m=n=0, $A^1$ and $A^3$ are trans-1,4-cyclohexylene, Q is —$CF_2CH_2$—, $R^2$=F, L=H, $Z^1$ is a single bond, $R^1$=$C_5H_{11}$)

1.0 g of the title compound was prepared in accordance with the process illustrated in Example 1, using 4-(5-pentyl-1,3-dioxane-2-yl)cyclohexanone in place of 4-(trans-4-pentylcyclohexyl)cyclohexanone in Example 1.

Example 4

Preparation of 1,1-Difluoro-1-[trans-4-(5-pentyl-1,3-dioxane-2-yl)cyclohexyl]-2-(3,4,5-trifluorophenyl)ethane (Compound No. 66 of formula (1) wherein k=1, l=m=n=0, $A^1$ and $A^3$ are trans-1,4-cyclohexylene, Q is —$CF_2CH_2$—, $R^2$=F, L=F, $Z^1$ is a single bond, R=$C_5H_{11}$)

1.0 g of the title compound was prepared in accordance with the process illustrated in Example 1, using 4-(5-pentyl-1,3-dioxane-2-yl)cyclohexanone in place of 4-(trans-4-pentylcyclohexyl)cyclohexanone in Example 1.

The following compounds (Compounds No. 1-566) can be prepared by suitably selecting and combining the processes illustrated in Examples 1–4 and known methods for the organic synthesis. The compounds obtained in Examples 1–4 are also shown below.

| No. | |
|---|---|
| 1 | 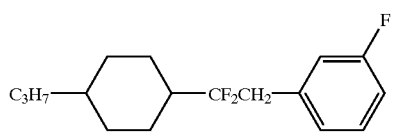 |
| 2 | 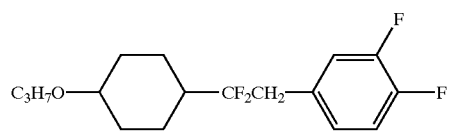 |
| 3 | 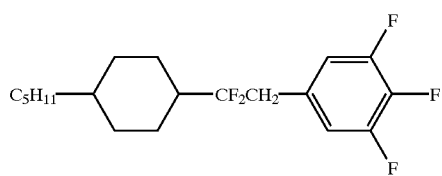 |
| 4 | 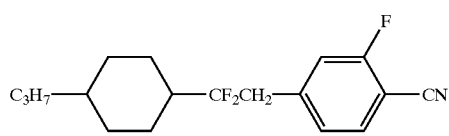 |
| 5 | 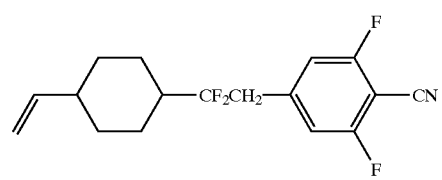 |
| 6 | 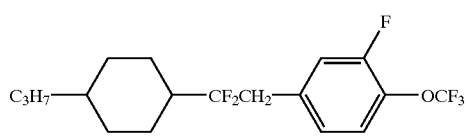 |
| 7 | 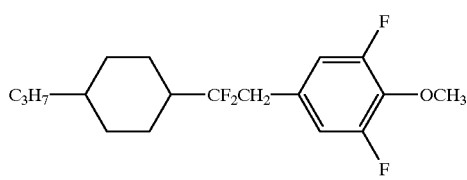 |
| 8 | 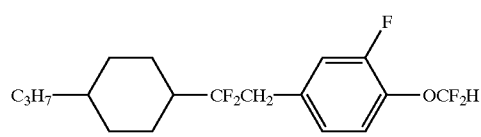 |
| 9 | 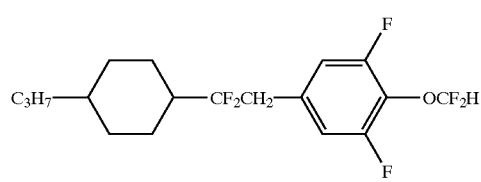 |

-continued
| No. | |
|---|---|
| 10 | 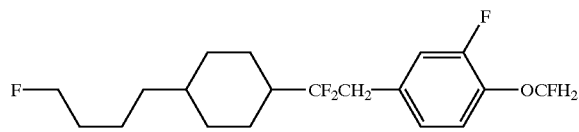 |
| 11 | 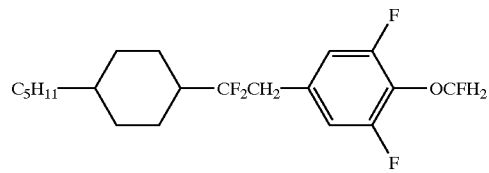 |
| 12 | 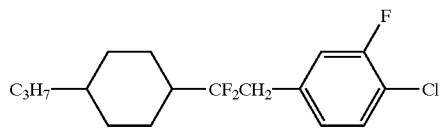 |
| 13 | 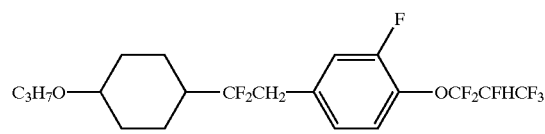 |
| 14 | 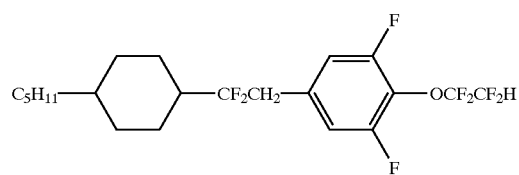 |
| 15 | 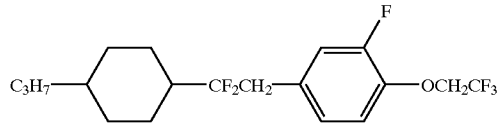 |
| 16 | 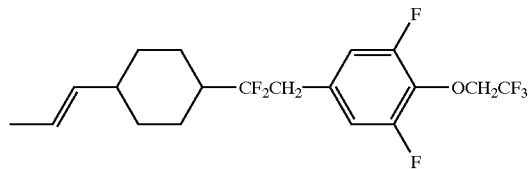 |
| 17 | 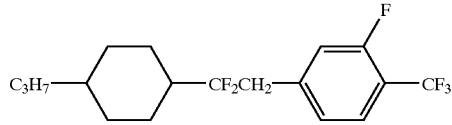 |
| 18 | 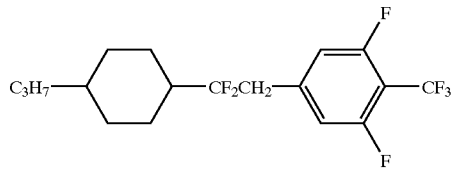 |
| 19 | 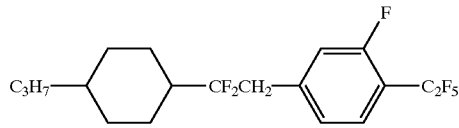 |

-continued
| No. | |
|---|---|
| 20 | 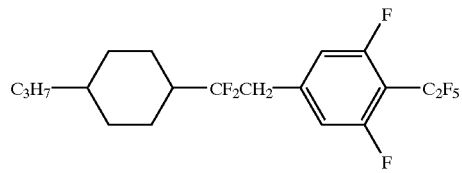 |
| 21 | 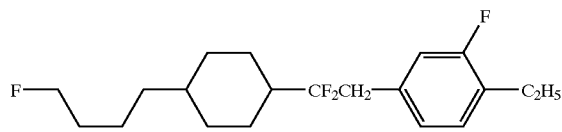 |
| 22 | 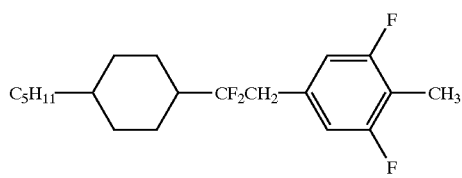 |
| 23 | 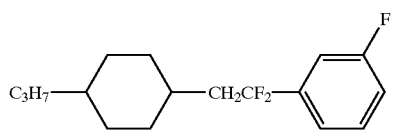 |
| 24 | 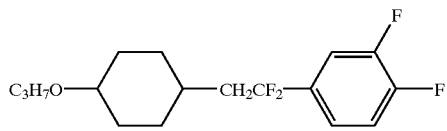 |
| 25 | 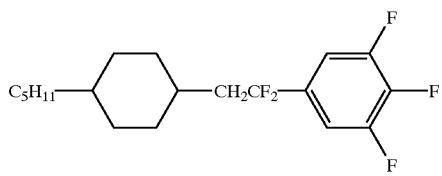 |
| 26 | 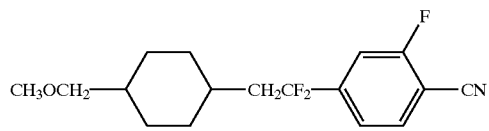 |
| 27 | 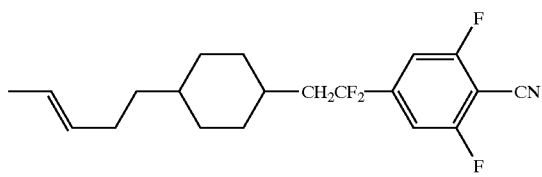 |
| 28 | 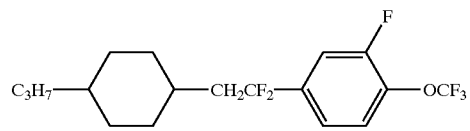 |

-continued
| No. | |
|---|---|
| 29 | 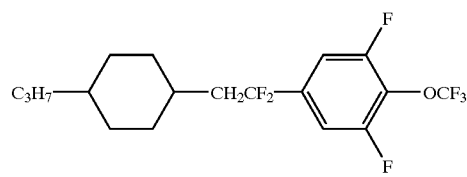 |
| 30 | 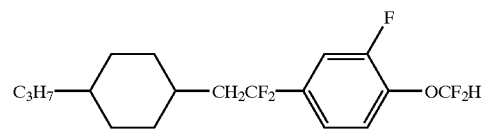 |
| 31 | 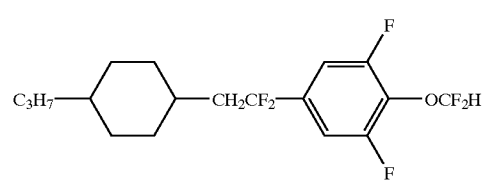 |
| 32 | 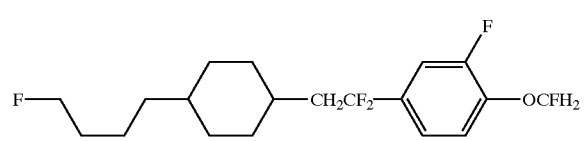 |
| 33 | 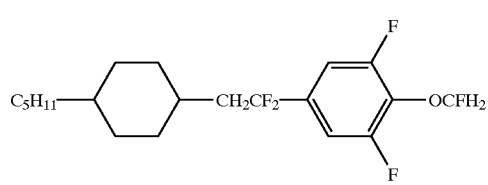 |
| 34 | 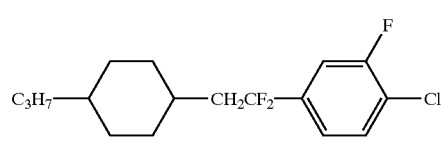 |
| 35 | 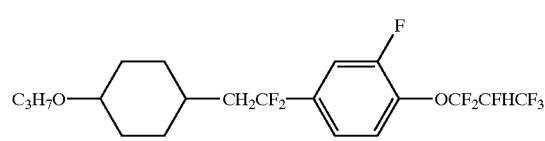 |
| 36 | 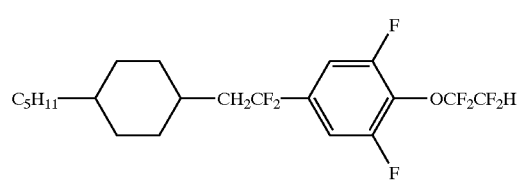 |
| 37 | 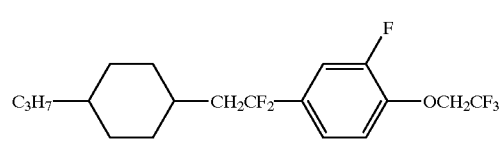 |

-continued
| No. | | |
|---|---|---|
| 38 | 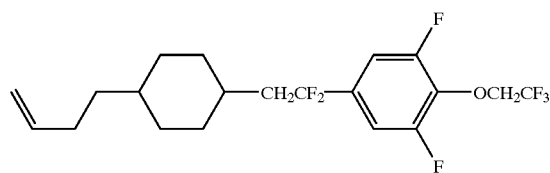 | |
| 39 | 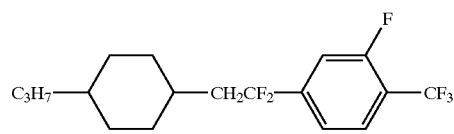 | |
| 40 | 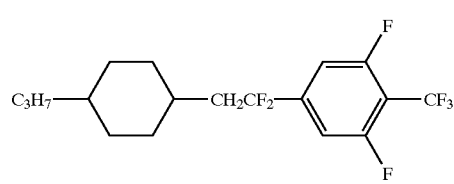 | |
| 41 | 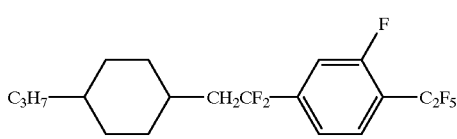 | |
| 42 | 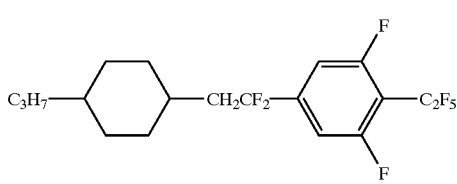 | |
| 43 | 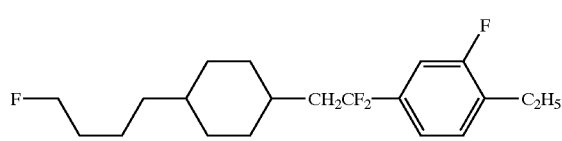 | |
| 44 | 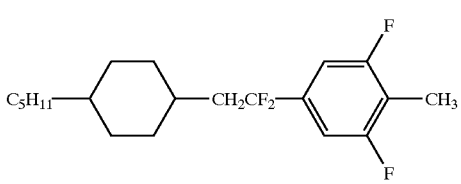 | |
| 45 | 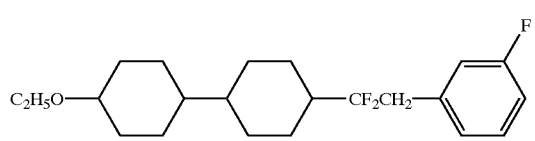 | |
| 46 | 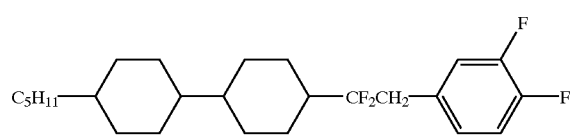 | Cr 84.1–85.0 N<br>95.3–95.4 Iso |

-continued
| No. | |
|---|---|
| 47 | 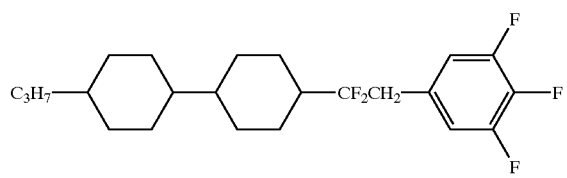 |
| 48 | 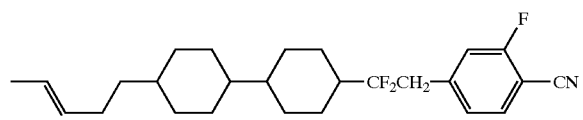 |
| 49 | 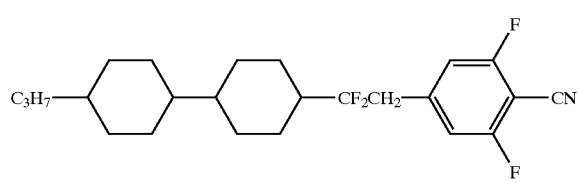 |
| 50 | 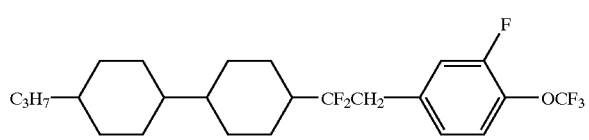 |
| 51 | 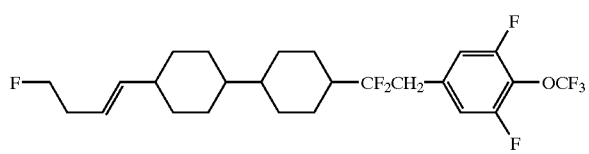 |
| 52 | 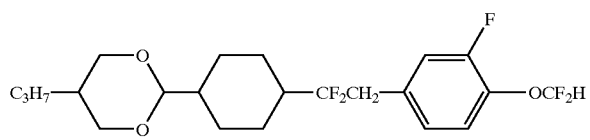 |
| 53 | 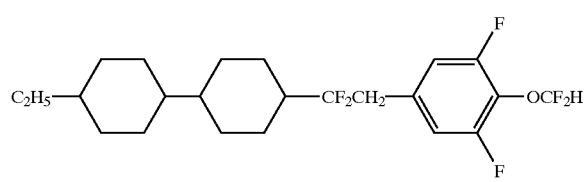 |
| 54 | 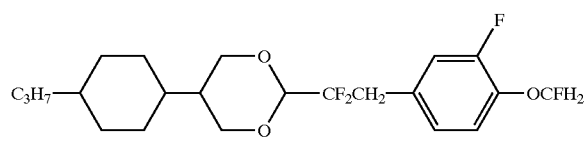 |
| 55 | 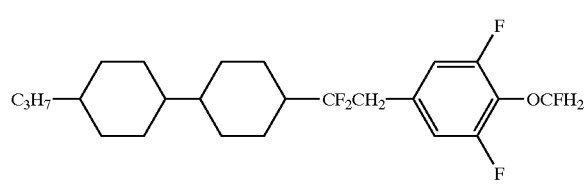 |

-continued
| No. | |
|---|---|
| 56 | 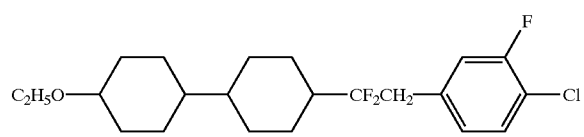 |
| 57 | 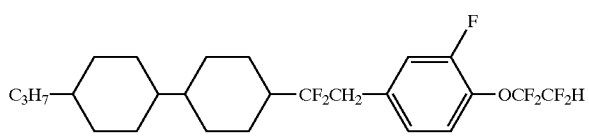 |
| 58 | 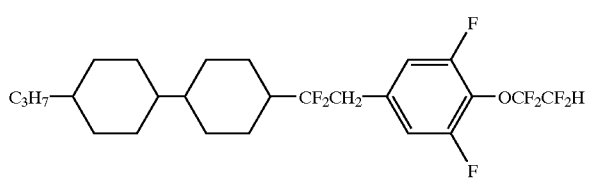 |
| 59 | 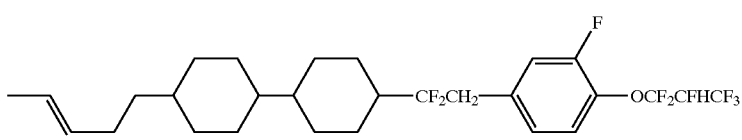 |
| 60 | 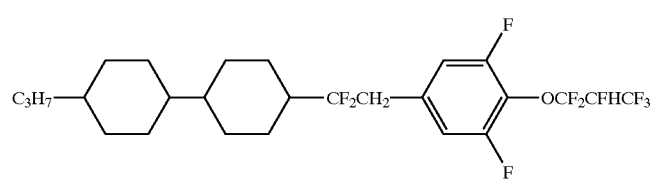 |
| 61 | 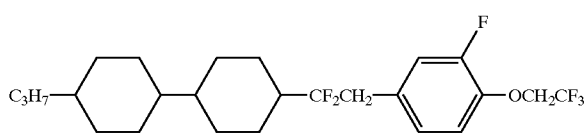 |
| 62 | 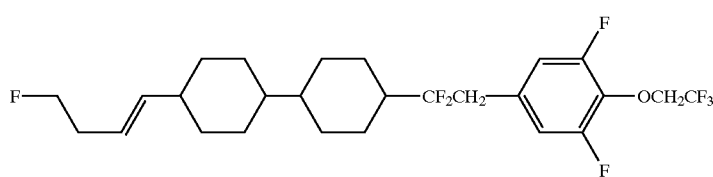 |
| 63 | 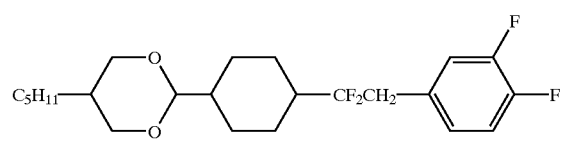 |
| 64 | 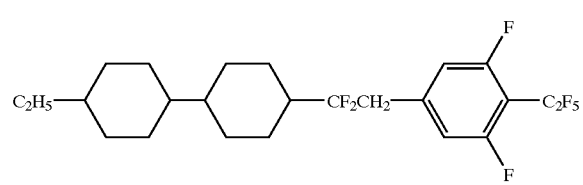 |

-continued
| No. | |
|---|---|
| 65 | 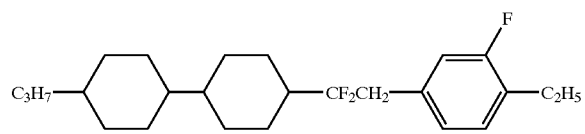 |
| 66 | 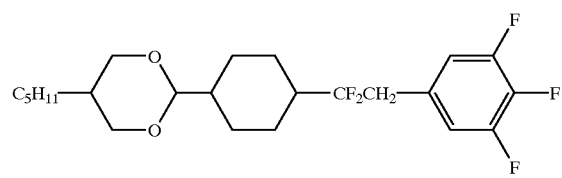 |
| 67 | 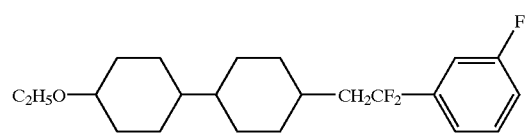 |
| 68 | 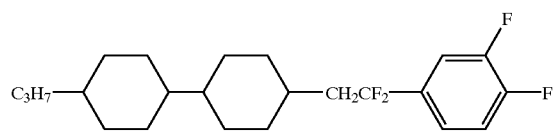 |
| 69 | 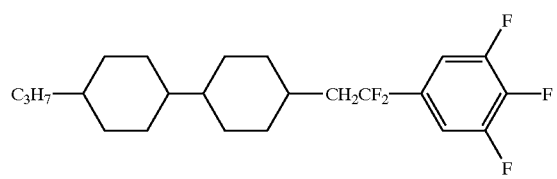 |
| 70 | 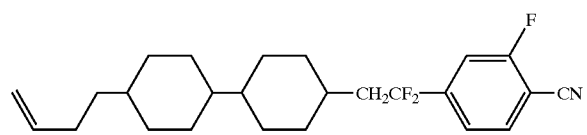 |
| 71 | 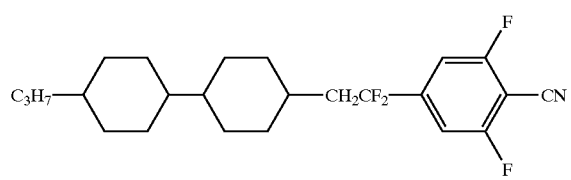 |
| 72 | 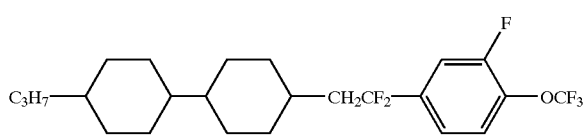 |
| 73 | 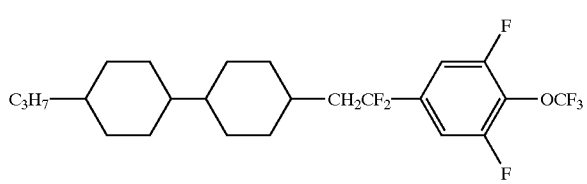 |

-continued
| No. | |
|---|---|
| 74 | 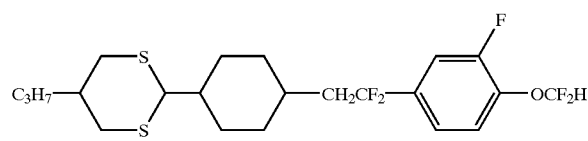 |
| 75 | 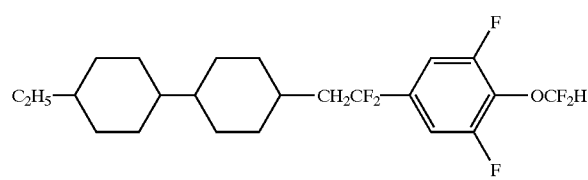 |
| 76 | 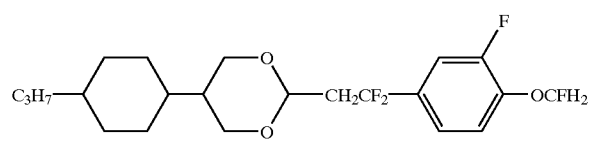 |
| 77 | 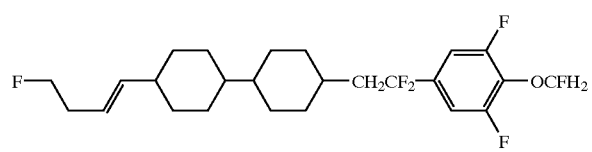 |
| 78 | 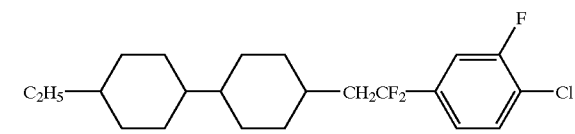 |
| 79 | 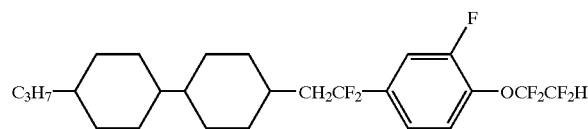 |
| 80 | 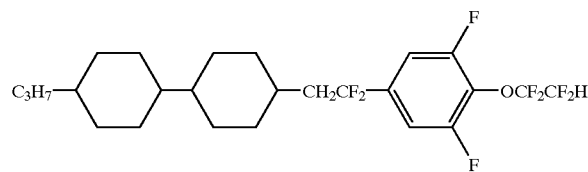 |
| 81 | 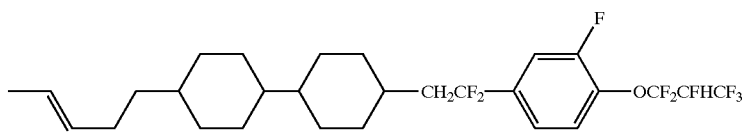 |
| 82 | 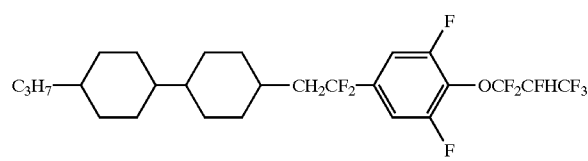 |
| 83 | 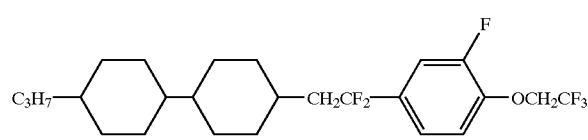 |

-continued
| No. | |
|---|---|
| 84 | 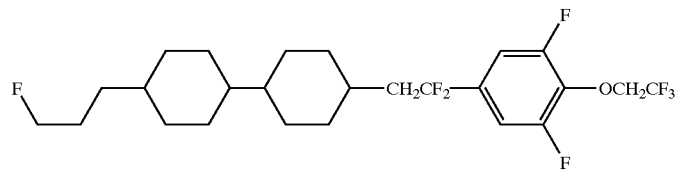 |
| 85 | 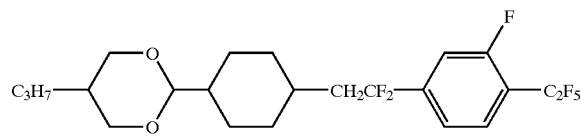 |
| 86 | 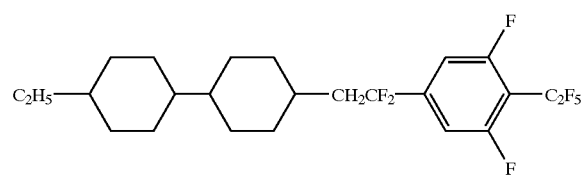 |
| 87 | 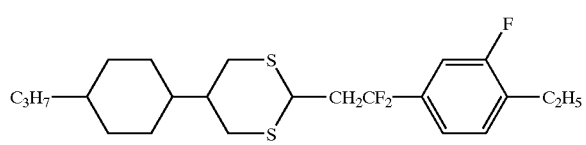 |
| 88 | 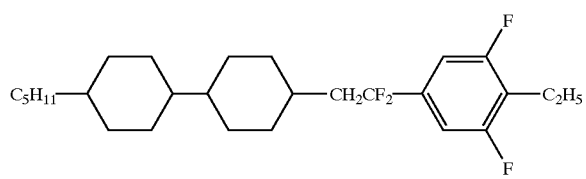 |
| 89 | 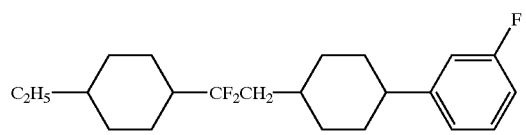 |
| 90 | 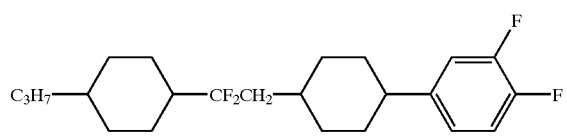 |
| 91 | 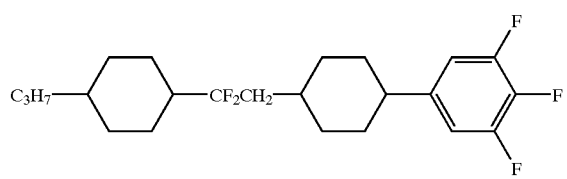 |
| 92 | 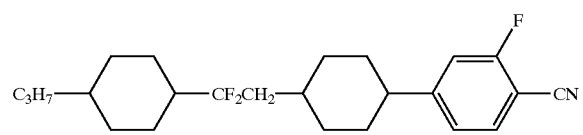 |

-continued
| No. | |
|---|---|
| 93 | 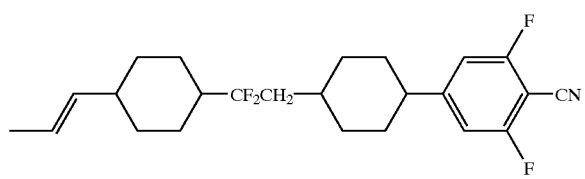 |
| 94 | 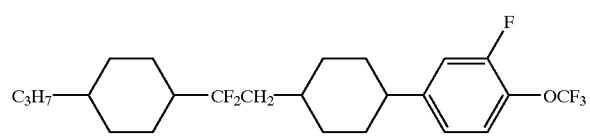 |
| 95 | 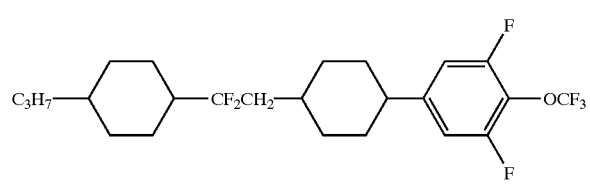 |
| 96 | 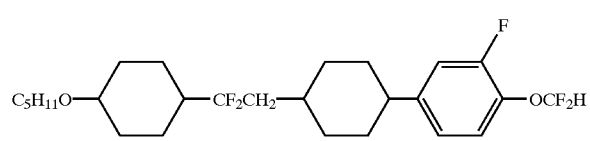 |
| 97 | 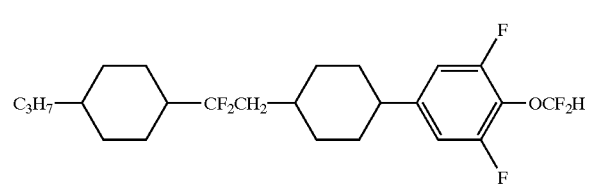 |
| 98 | 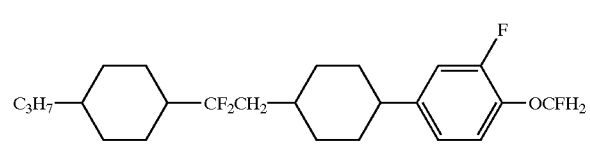 |
| 99 | 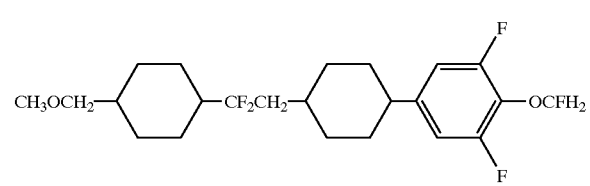 |
| 100 | 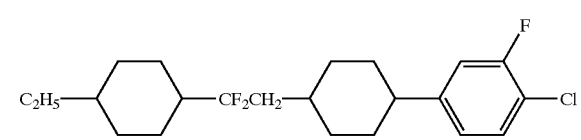 |
| 101 | 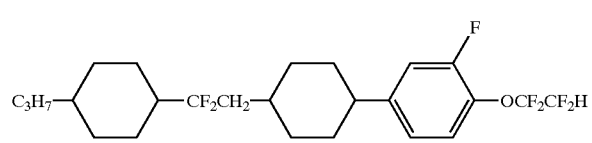 |

-continued
| No. | |
|---|---|
| 102 | 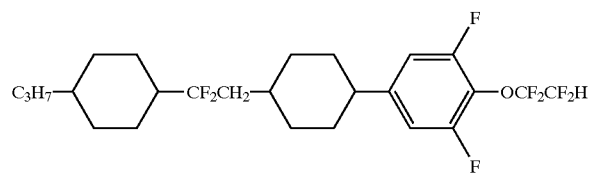 |
| 103 | 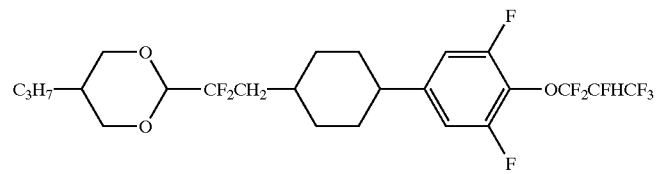 |
| 104 | 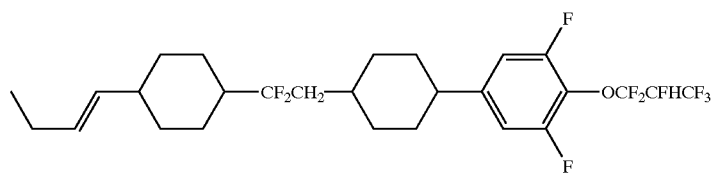 |
| 105 | 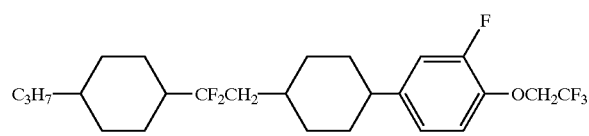 |
| 106 | 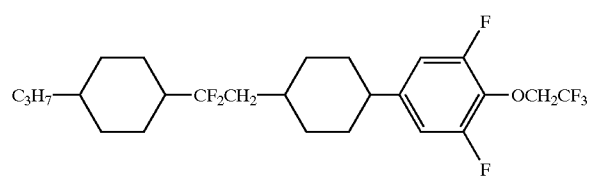 |
| 107 | 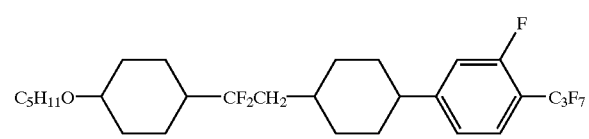 |
| 108 | 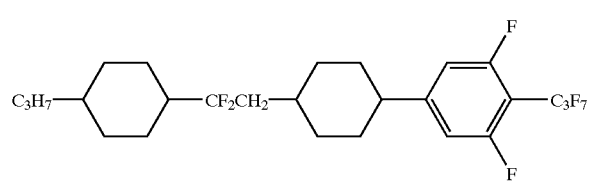 |
| 109 | 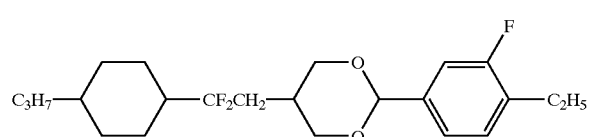 |
| 110 | 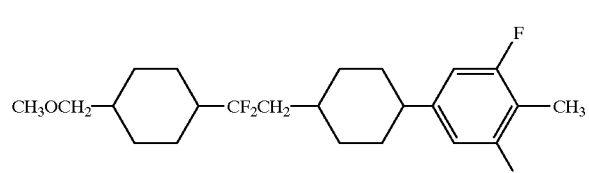 |

-continued
| No. | |
|---|---|
| 111 | 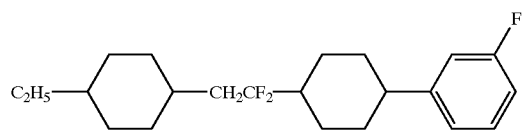 |
| 112 | 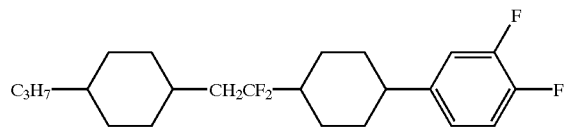 |
| 113 | 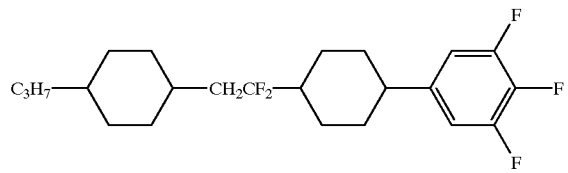 |
| 114 | 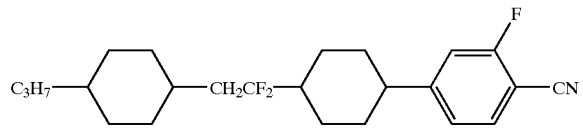 |
| 115 | 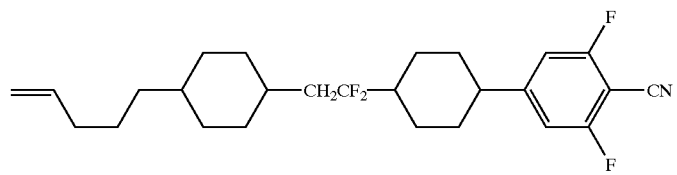 |
| 116 | 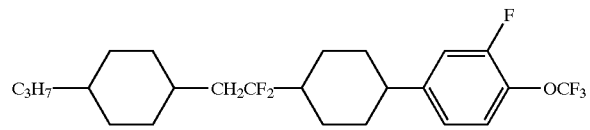 |
| 117 | 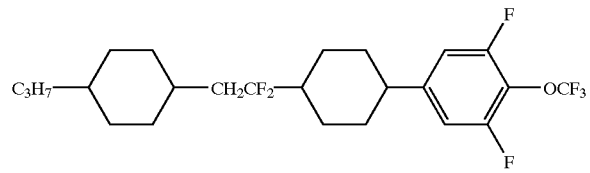 |
| 118 | 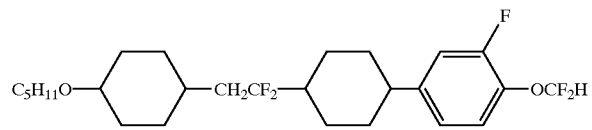 |
| 119 | 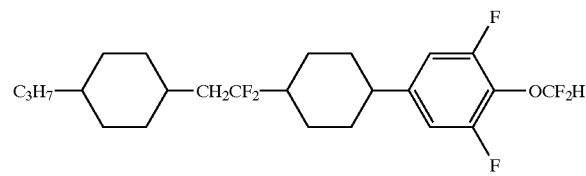 |
| 120 | 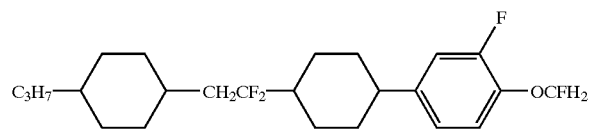 |

-continued
| No. | |
|---|---|
| 121 | 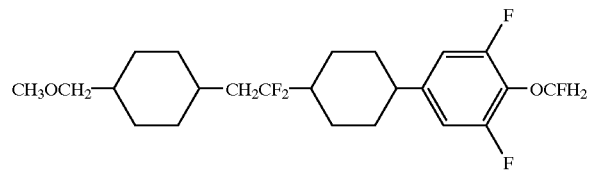 |
| 122 | 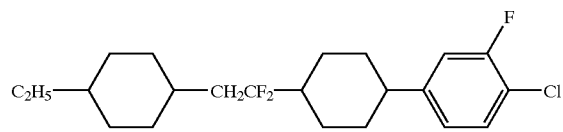 |
| 123 | 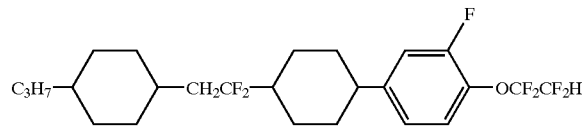 |
| 124 | 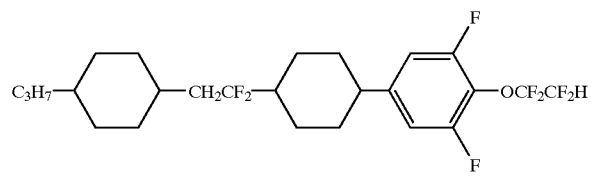 |
| 125 | 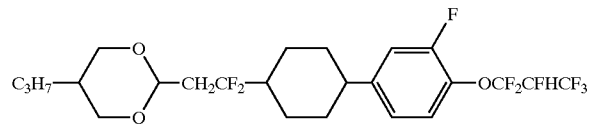 |
| 126 | 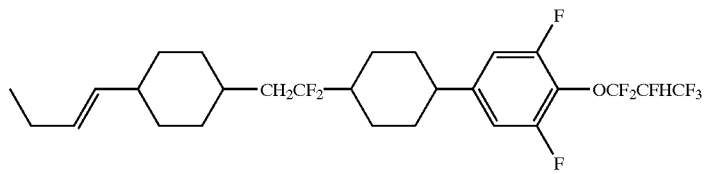 |
| 127 | 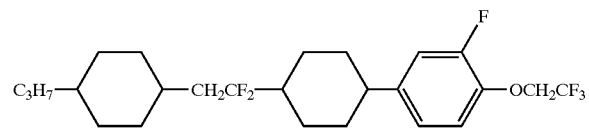 |
| 128 | 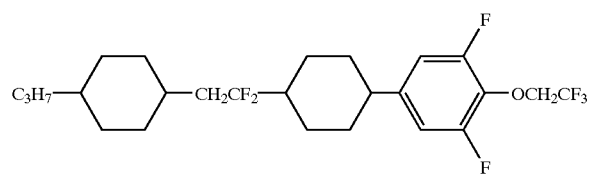 |
| 129 | 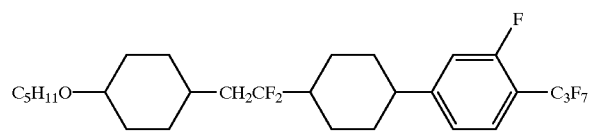 |

-continued
| No. | |
|---|---|
| 130 | 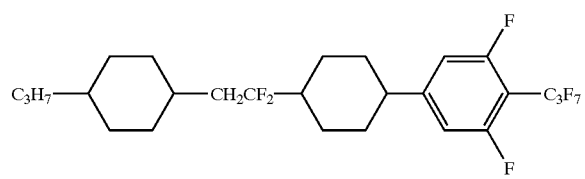 |
| 131 | 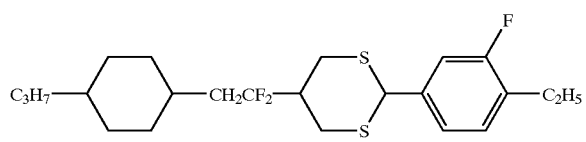 |
| 132 | 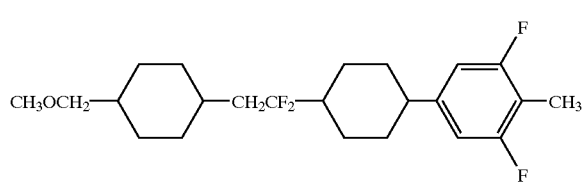 |
| 133 | 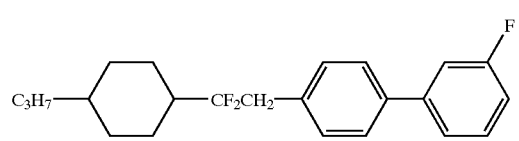 |
| 134 | 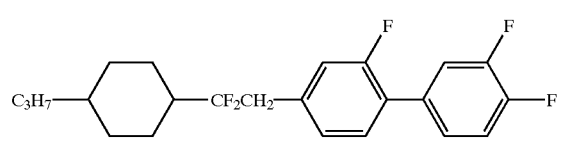 |
| 135 | 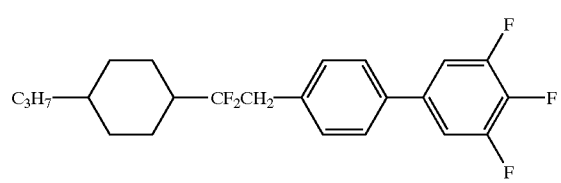 |
| 136 | 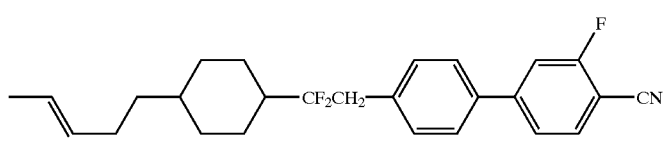 |
| 137 | 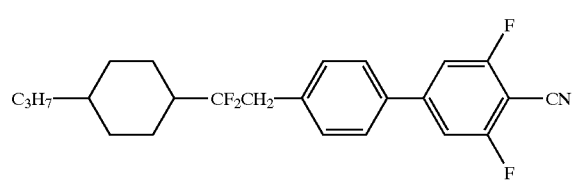 |
| 138 | 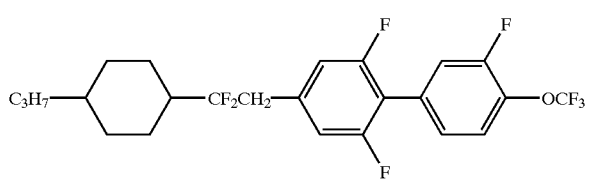 |

-continued
| No. | |
|---|---|
| 139 | 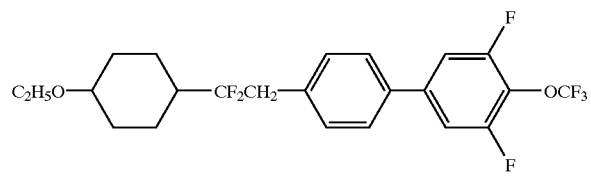 |
| 140 | 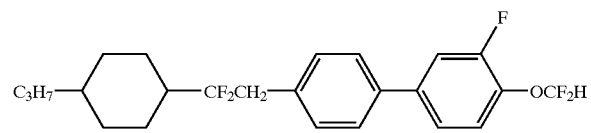 |
| 141 | 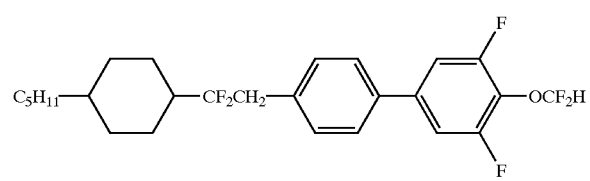 |
| 142 | 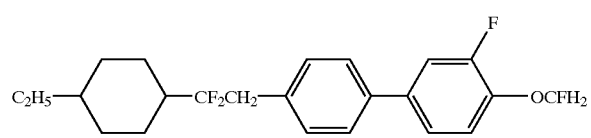 |
| 143 | 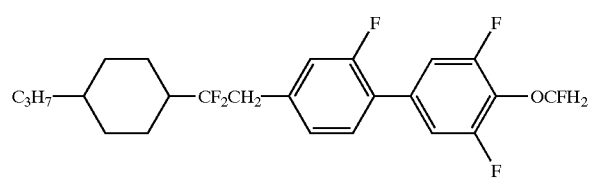 |
| 144 | 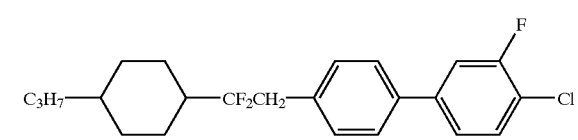 |
| 145 | 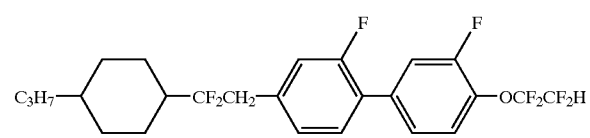 |
| 146 | 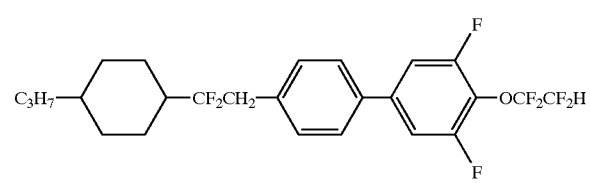 |
| 147 | 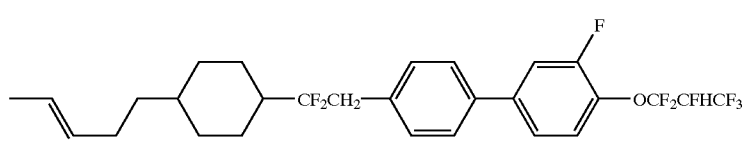 |

-continued
| No. | |
|---|---|
| 148 | 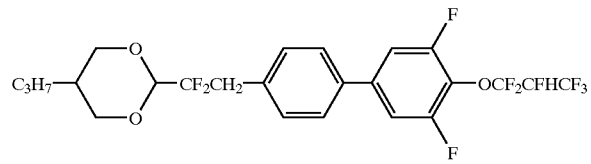 |
| 149 | 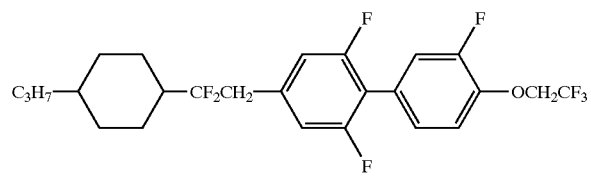 |
| 150 | 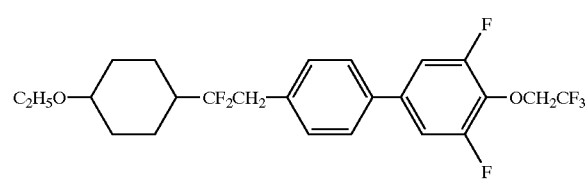 |
| 151 | 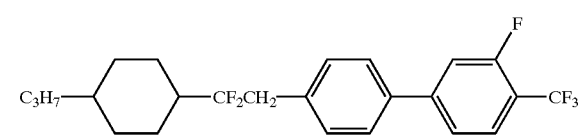 |
| 152 | 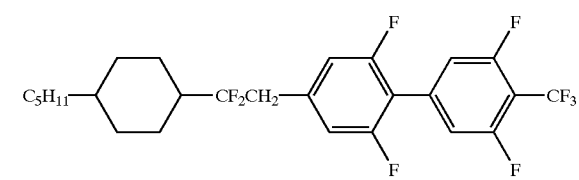 |
| 153 | 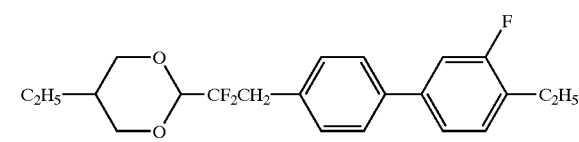 |
| 154 | 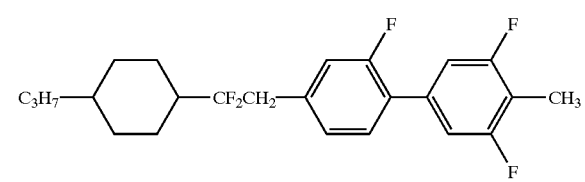 |
| 155 | 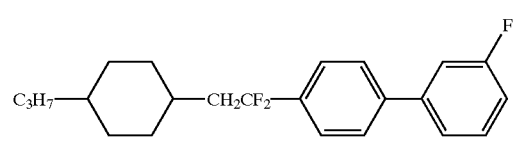 |
| 156 | 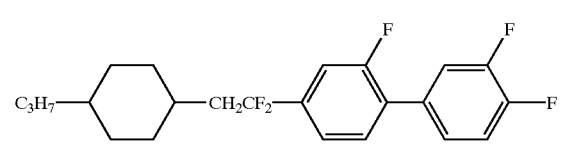 |

-continued
| No. | |
|---|---|
| 157 | 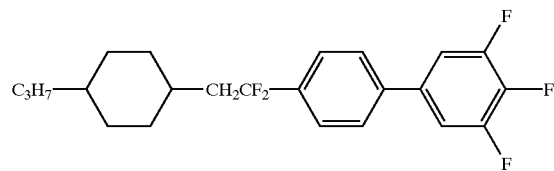 |
| 158 | 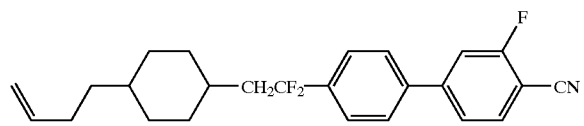 |
| 159 | 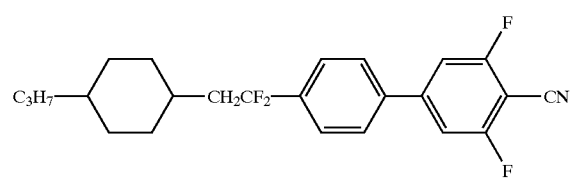 |
| 160 | 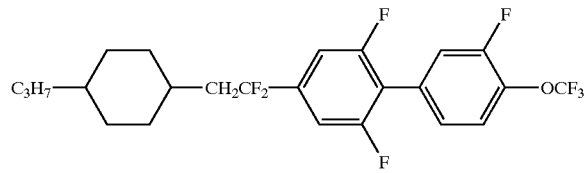 |
| 161 | 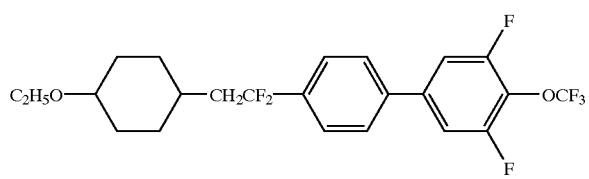 |
| 162 | 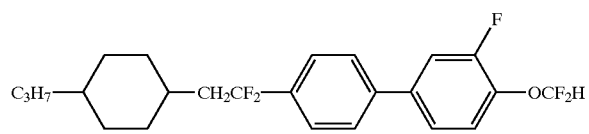 |
| 163 | 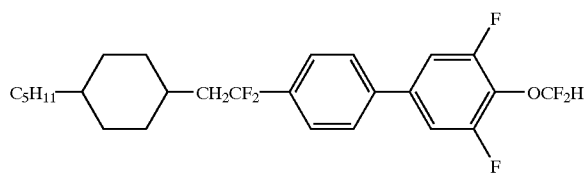 |
| 164 | 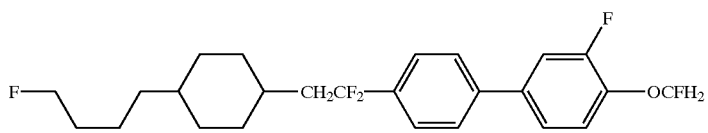 |
| 165 | 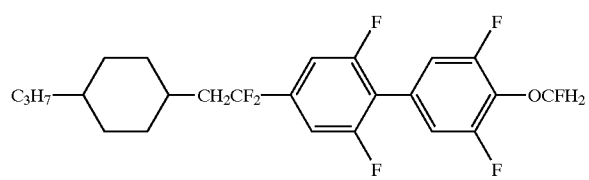 |

-continued
| No. | |
|---|---|
| 166 | 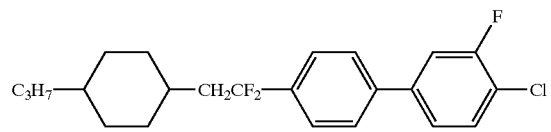 |
| 167 | 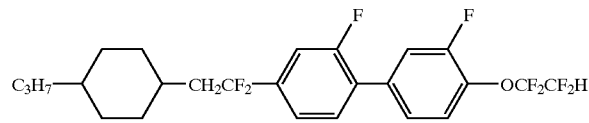 |
| 168 | 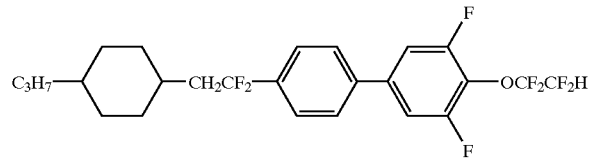 |
| 169 | 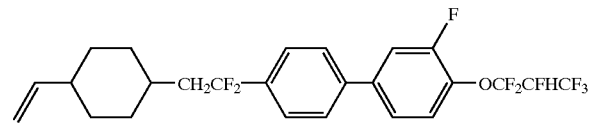 |
| 170 | 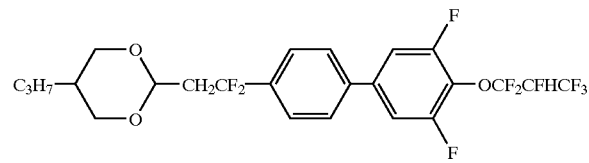 |
| 171 | 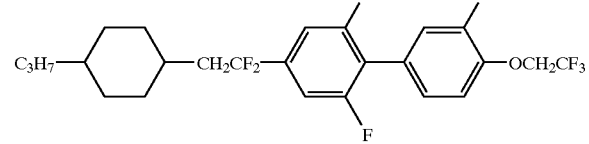 |
| 172 | 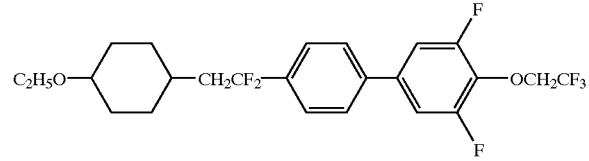 |
| 173 | 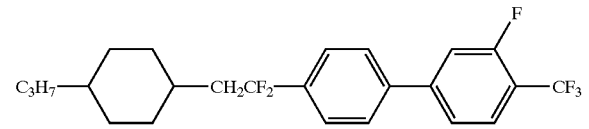 |
| 174 | 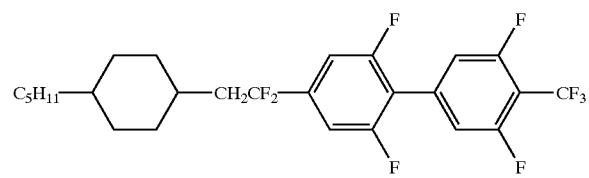 |

-continued
| No. | |
|---|---|
| 175 | 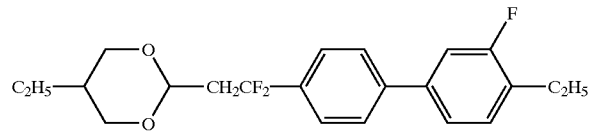 |
| 176 | 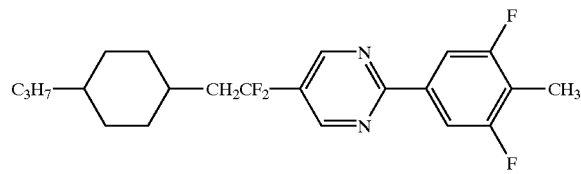 |
| 177 | 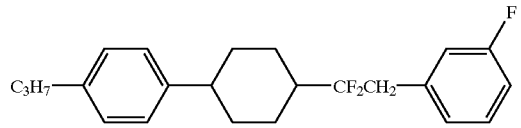 |
| 178 | 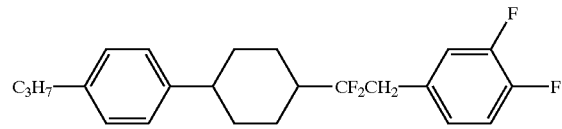 |
| 179 | 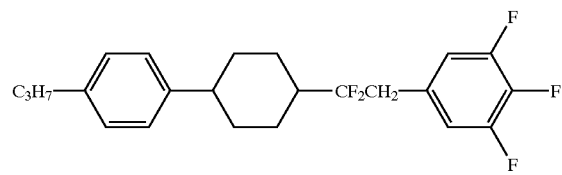 |
| 180 | 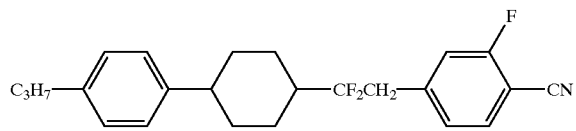 |
| 181 | 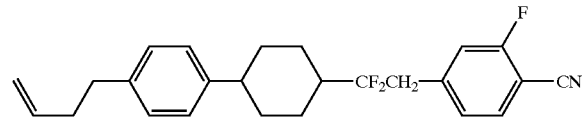 |
| 182 | 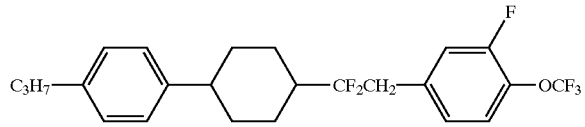 |
| 183 | 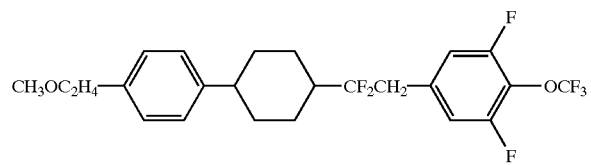 |
| 184 | 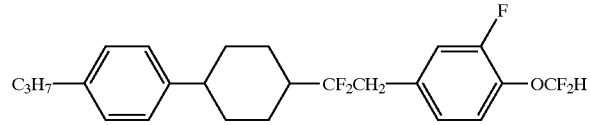 |

-continued
| No. | |
|---|---|
| 185 | 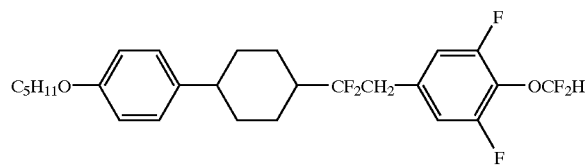 |
| 186 | 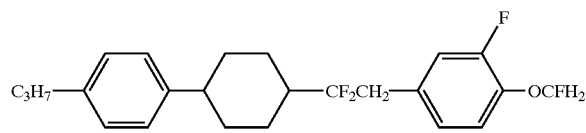 |
| 187 | 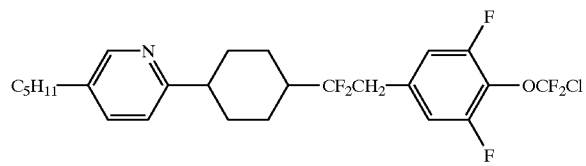 |
| 188 | 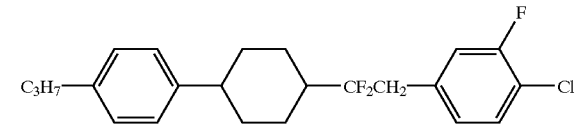 |
| 189 | 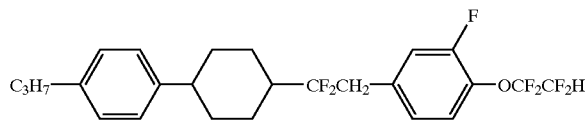 |
| 190 | 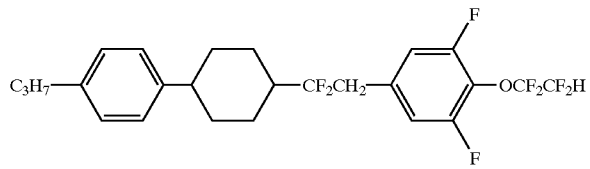 |
| 191 | 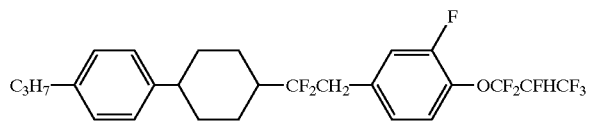 |
| 192 | 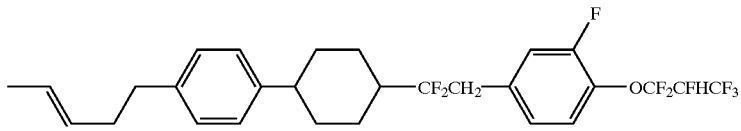 |
| 193 | 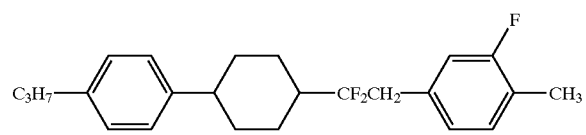 |
| 194 | 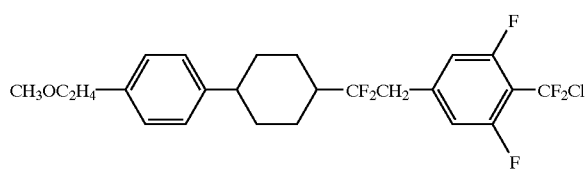 |

-continued
| No. | |
|---|---|
| 195 | 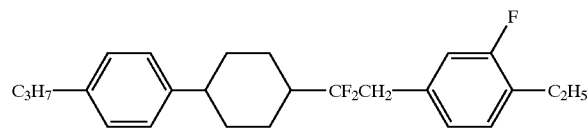 |
| 196 | 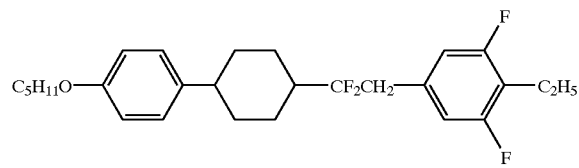 |
| 197 | 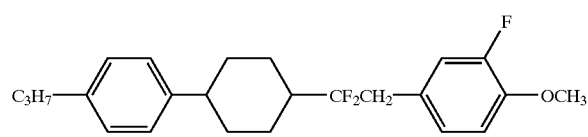 |
| 198 | 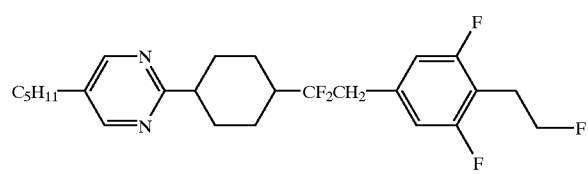 |
| 199 | 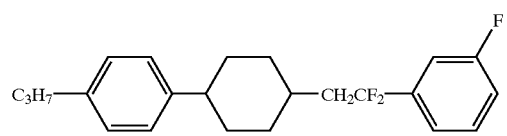 |
| 200 | 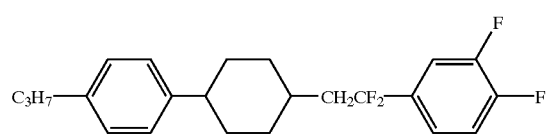 |
| 201 | 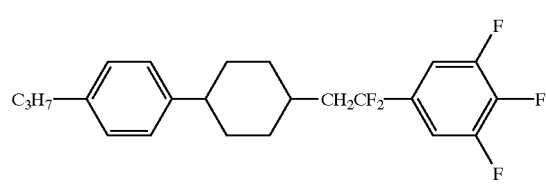 |
| 202 | 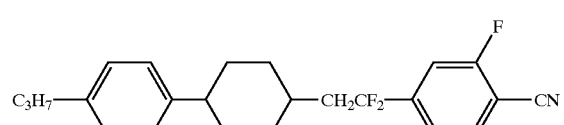 |
| 203 | 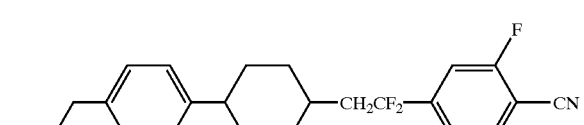 |
| 204 | 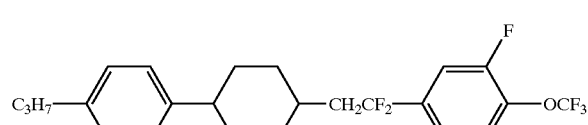 |

| No. | |
|---|---|
| 205 | 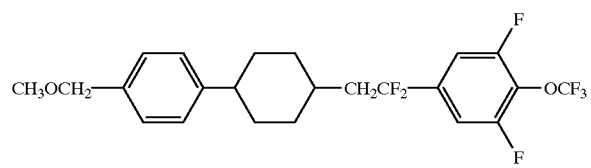 |
| 206 | 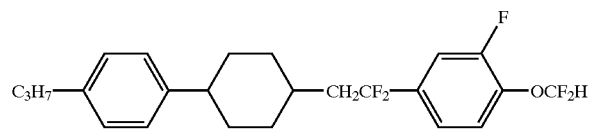 |
| 207 | 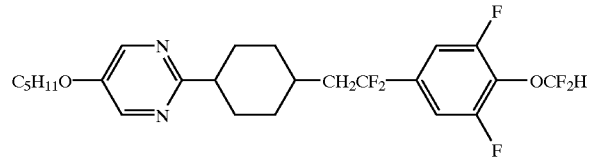 |
| 208 | 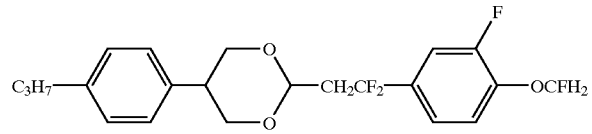 |
| 209 | 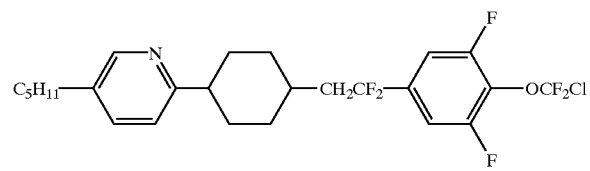 |
| 210 | 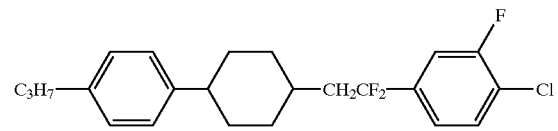 |
| 211 | 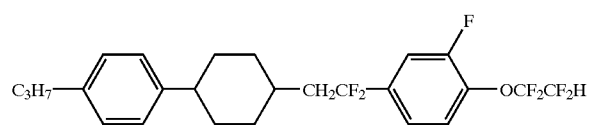 |
| 212 | 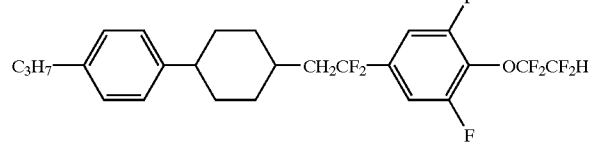 |
| 213 | 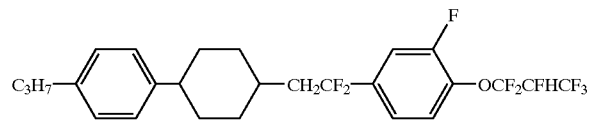 |
| 214 | 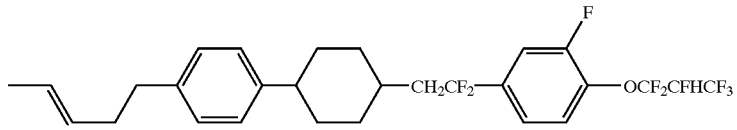 |

-continued
| No. | |
|---|---|
| 215 | 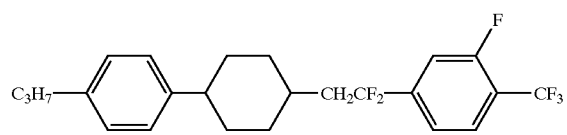 |
| 216 | 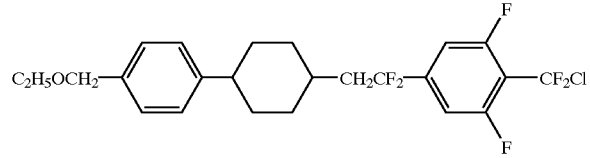 |
| 217 | 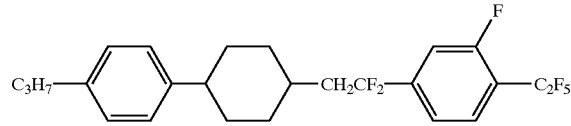 |
| 218 | 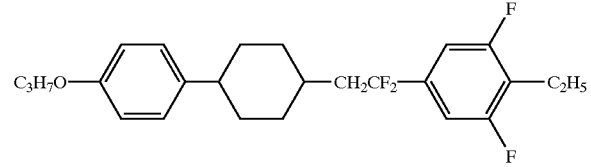 |
| 219 | 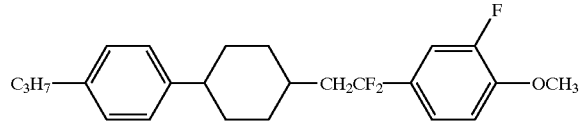 |
| 220 | 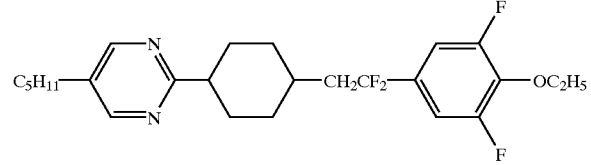 |
| 221 | 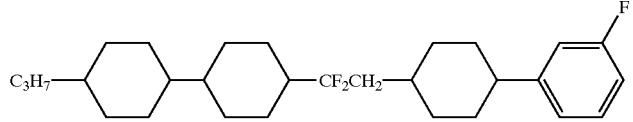 |
| 222 | 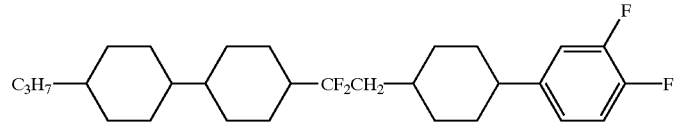 |
| 223 | 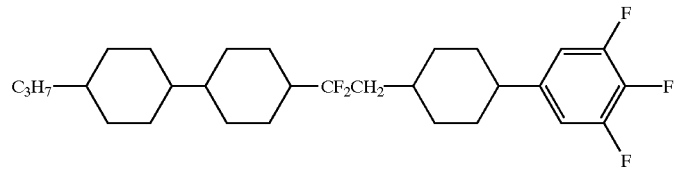 |
| 224 | 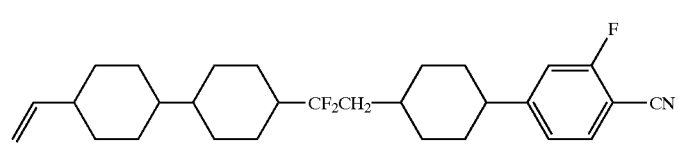 |

-continued
| No. | |
|---|---|
| 225 | 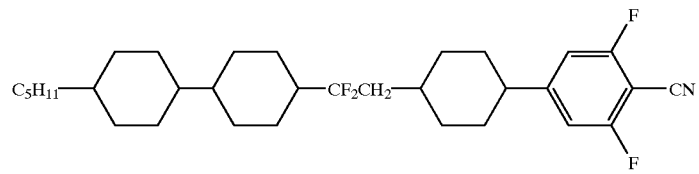 |
| 226 | 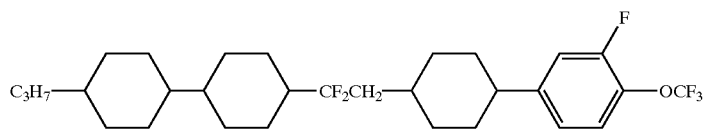 |
| 227 | 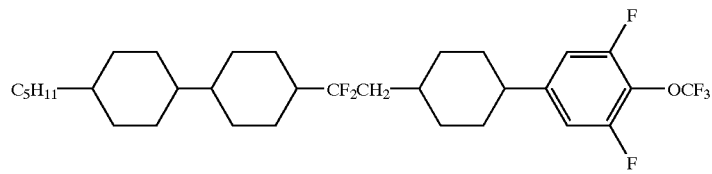 |
| 228 | 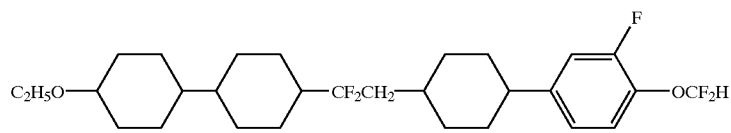 |
| 229 | 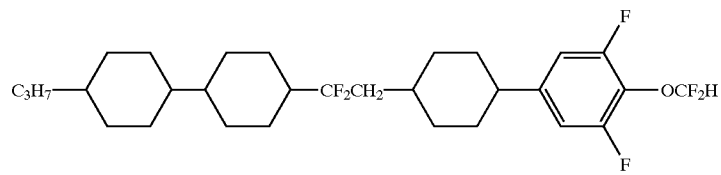 |
| 230 | 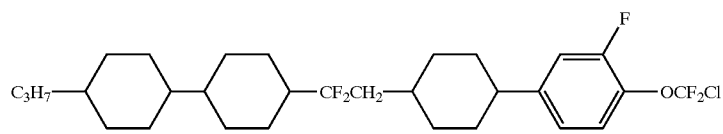 |
| 231 | 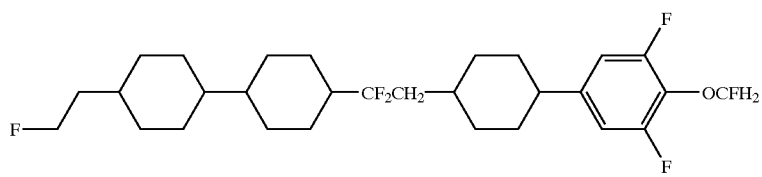 |
| 232 | 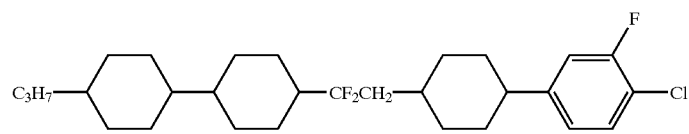 |
| 233 | 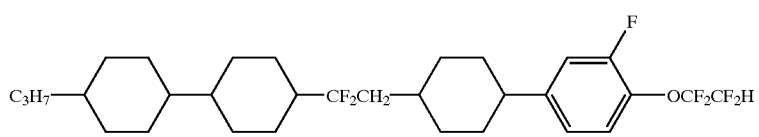 |

-continued
| No. | |
|---|---|
| 234 | 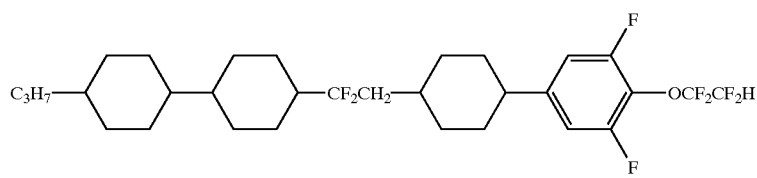 |
| 235 | 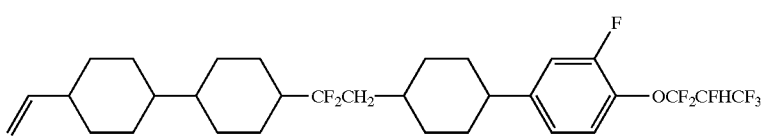 |
| 236 | 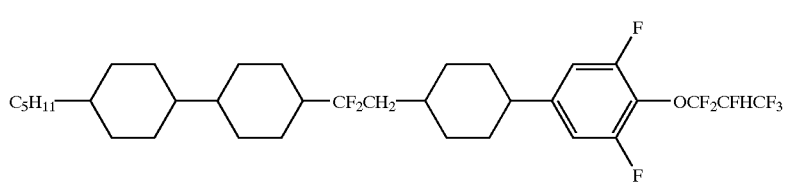 |
| 237 | 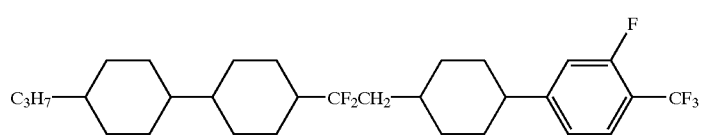 |
| 238 | 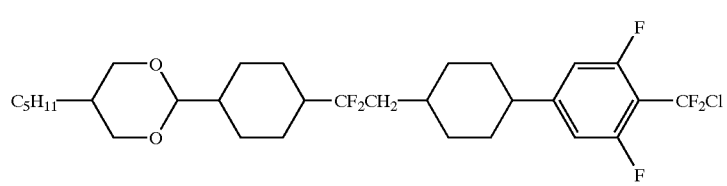 |
| 239 | 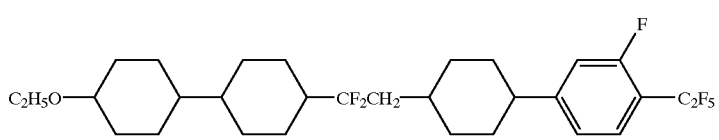 |
| 240 | 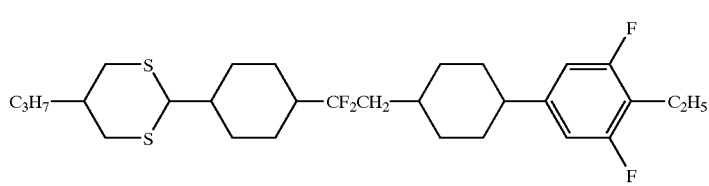 |
| 241 | 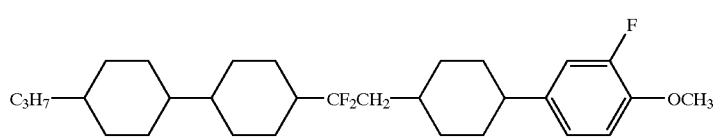 |
| 242 | 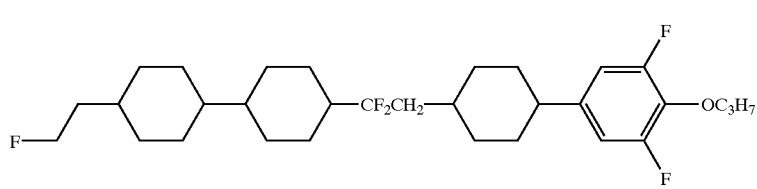 |

-continued
| No. | |
|---|---|
| 243 | 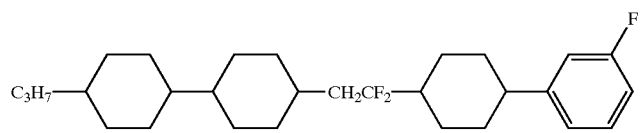 |
| 244 | 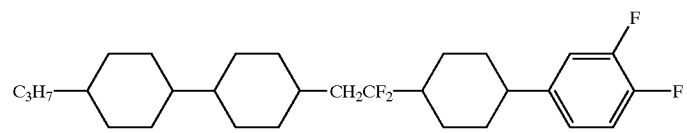 |
| 245 | 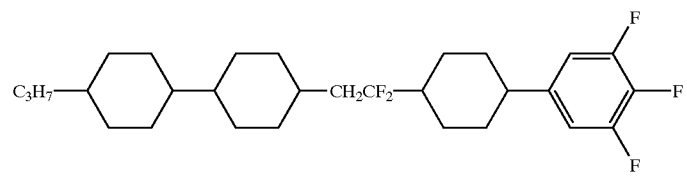 |
| 246 | 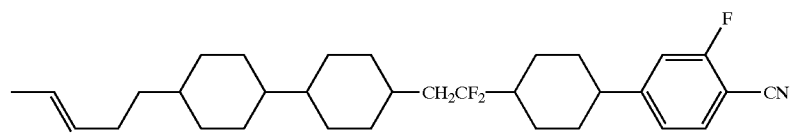 |
| 247 | 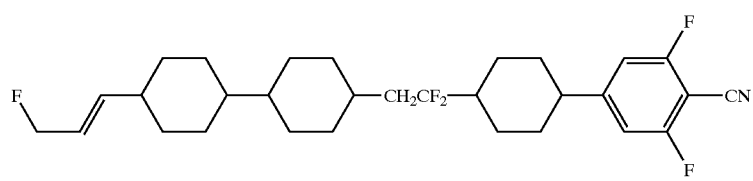 |
| 248 | 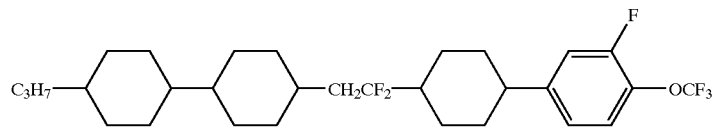 |
| 249 | 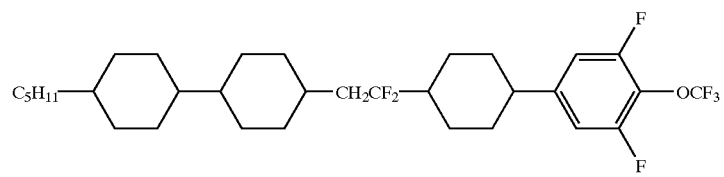 |
| 250 | 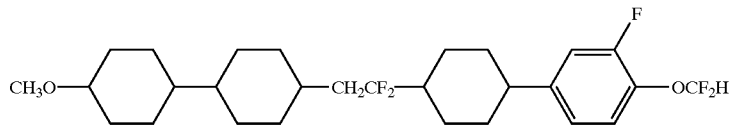 |
| 251 | 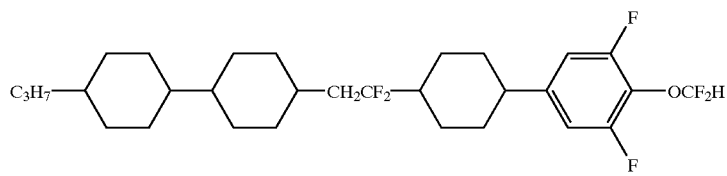 |
| 252 | 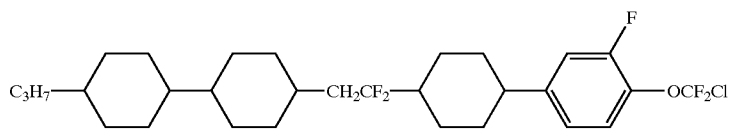 |

-continued
| No. | |
|---|---|
| 253 | 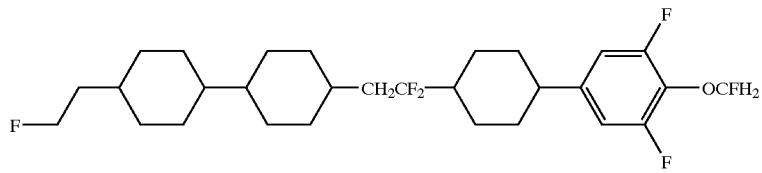 |
| 254 | 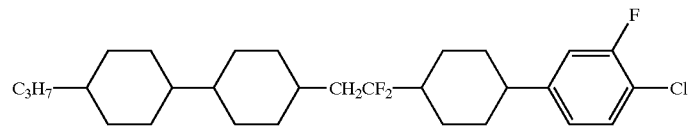 |
| 255 | 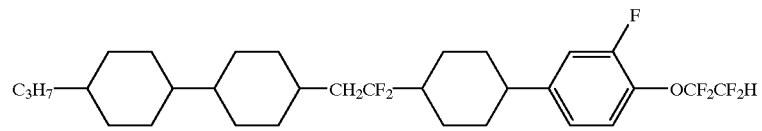 |
| 256 | 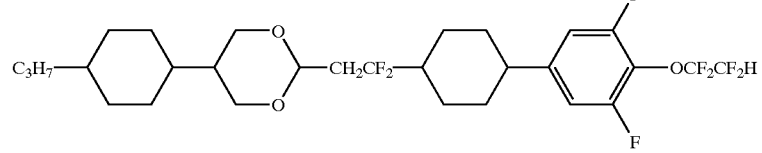 |
| 257 | 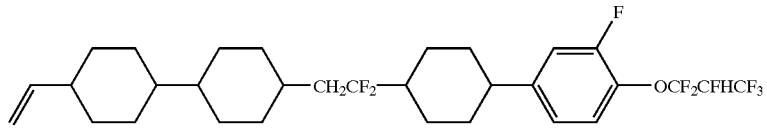 |
| 258 | 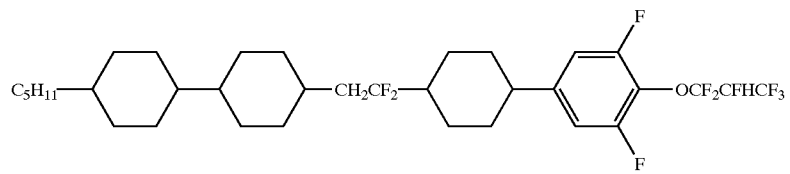 |
| 259 | 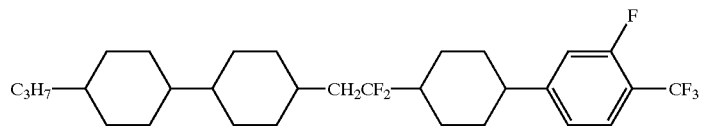 |
| 260 | 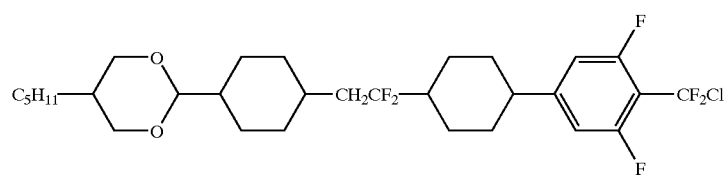 |
| 261 | 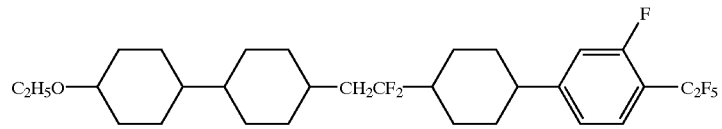 |

| No. | |
|---|---|
| 262 | 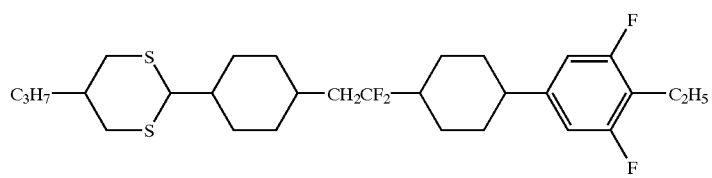 |
| 263 | 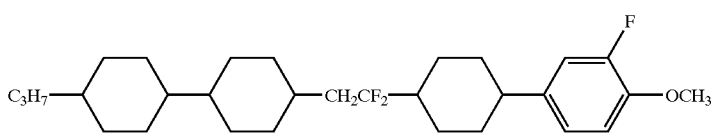 |
| 264 | 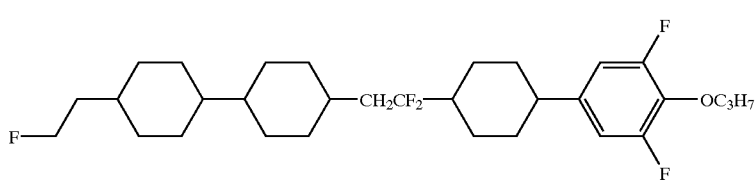 |
| 265 | 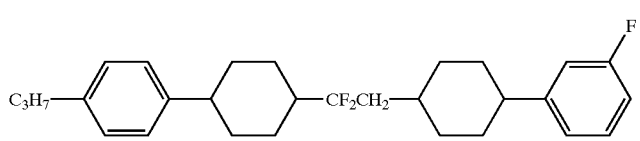 |
| 266 | 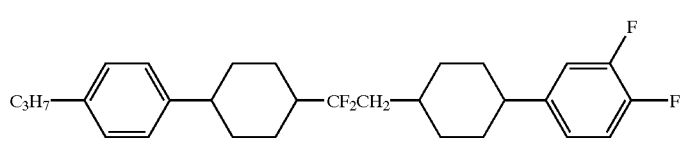 |
| 267 | 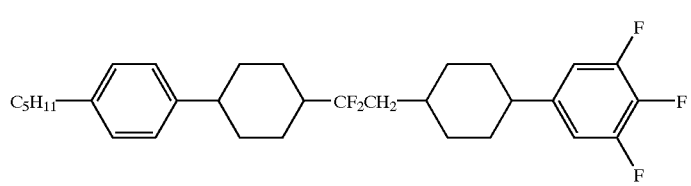 |
| 268 | 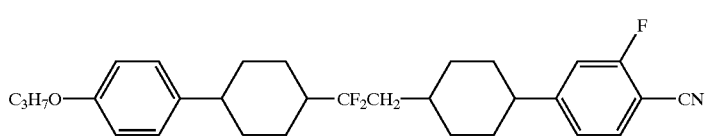 |
| 269 | 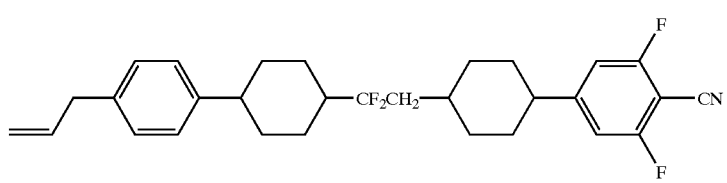 |
| 270 | 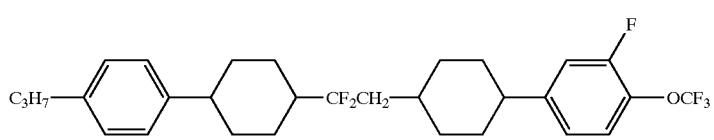 |

-continued
| No. | |
|---|---|
| 271 | 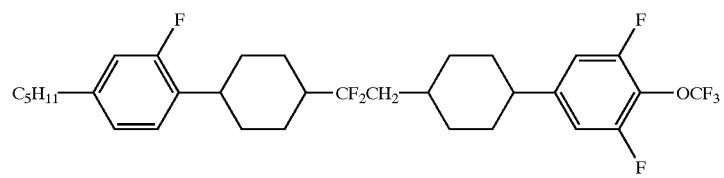 |
| 272 | 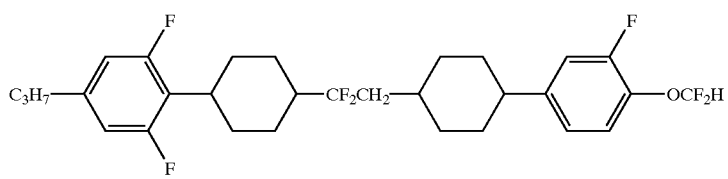 |
| 273 | 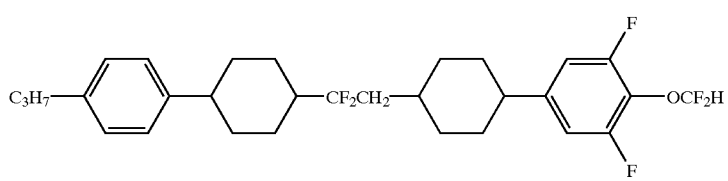 |
| 274 | 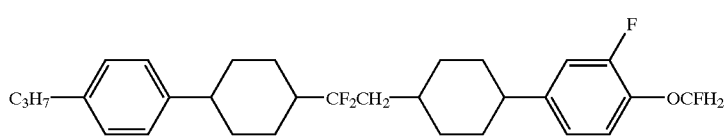 |
| 275 | 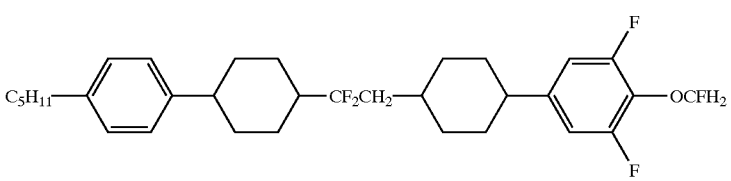 |
| 276 | 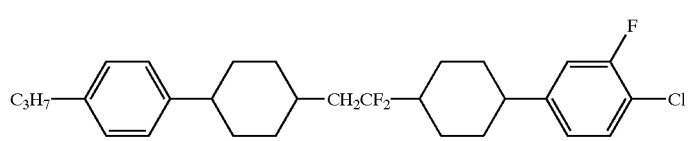 |
| 277 | 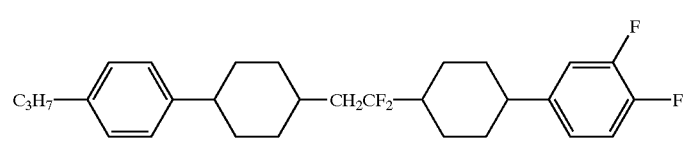 |
| 278 | 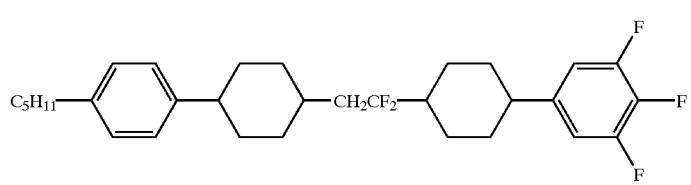 |
| 279 | 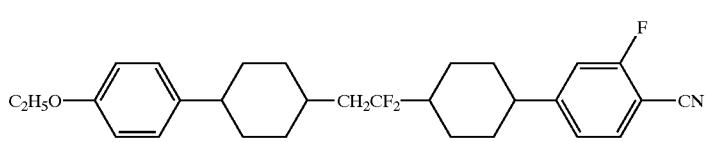 |

| No. | |
|---|---|
| 280 | 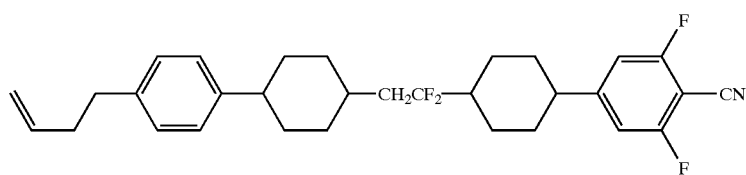 |
| 281 | 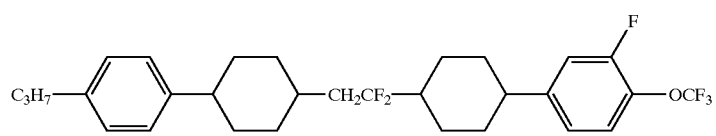 |
| 282 | 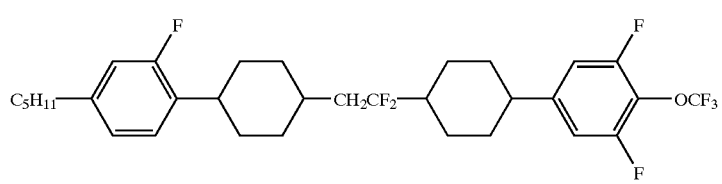 |
| 283 | 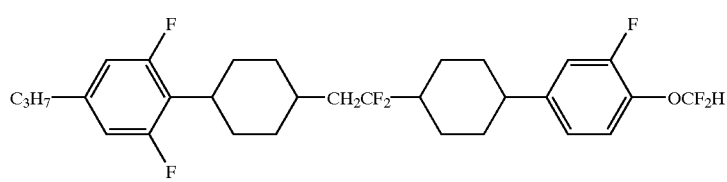 |
| 284 | 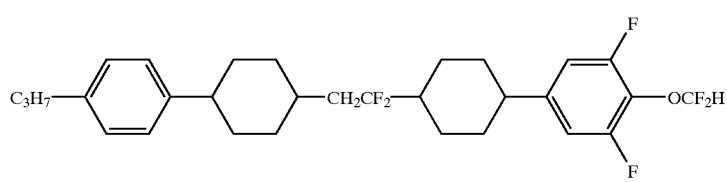 |
| 285 | 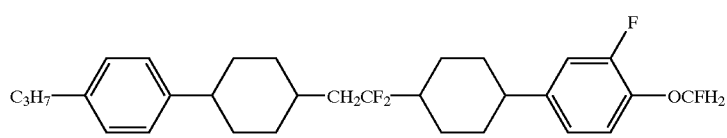 |
| 286 | 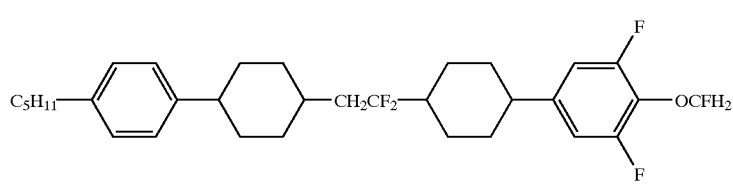 |
| 287 | 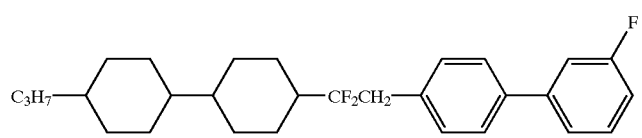 |
| 288 | 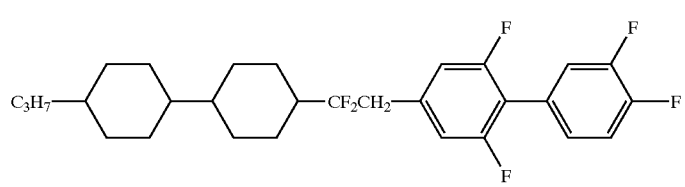 |

-continued
| No. | |
|---|---|
| 289 | 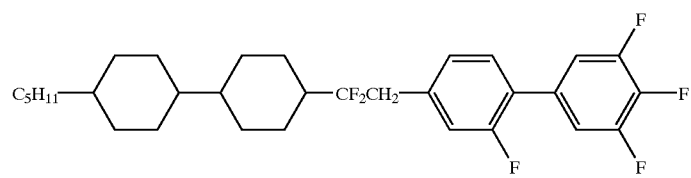 |
| 290 | 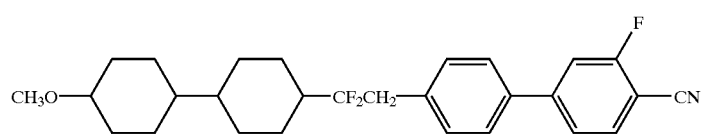 |
| 291 | 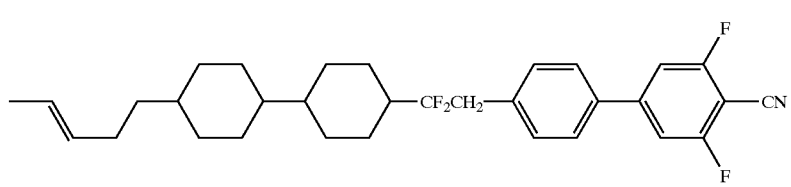 |
| 292 | 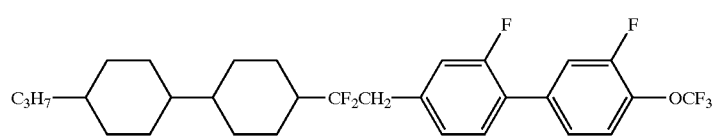 |
| 293 | 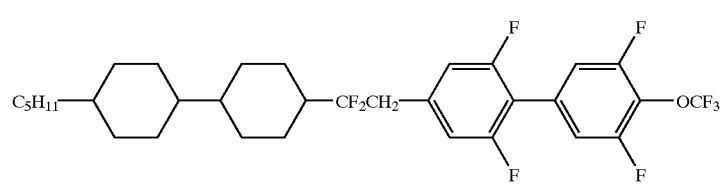 |
| 294 | 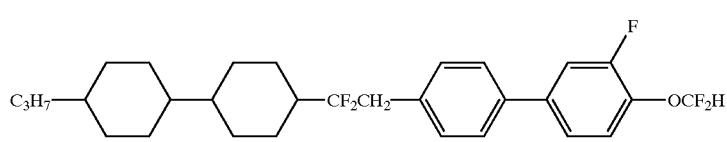 |
| 295 | 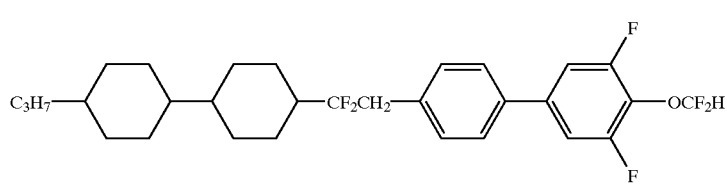 |
| 296 | 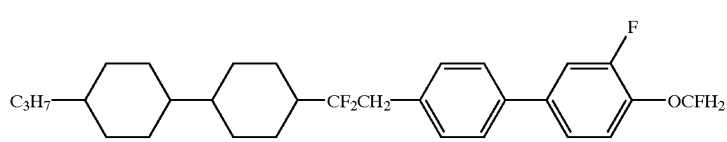 |
| 297 | 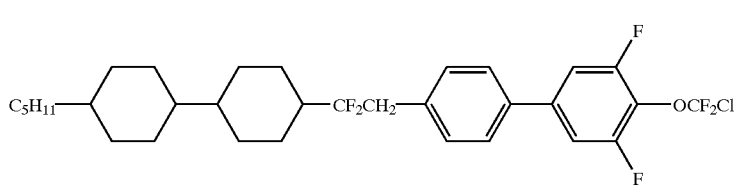 |

-continued
| No. | |
|---|---|
| 298 | 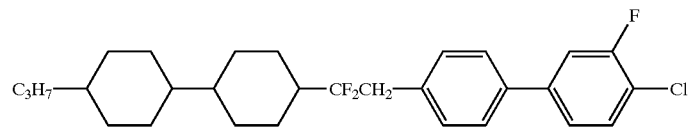 |
| 299 | 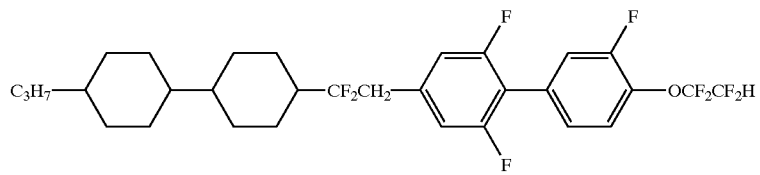 |
| 300 | 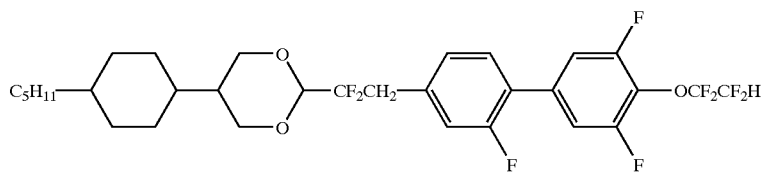 |
| 301 | 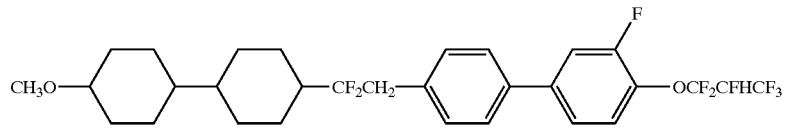 |
| 302 | 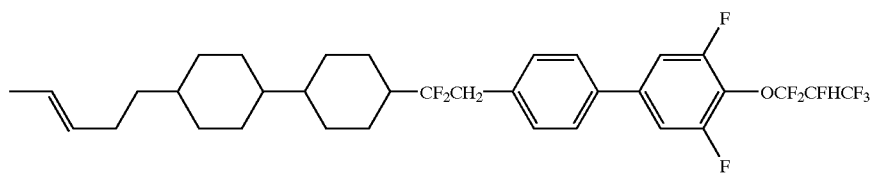 |
| 303 | 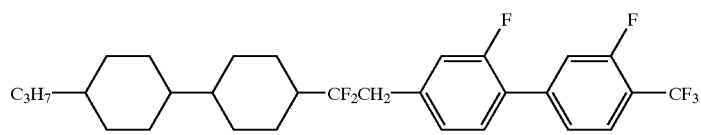 |
| 304 | 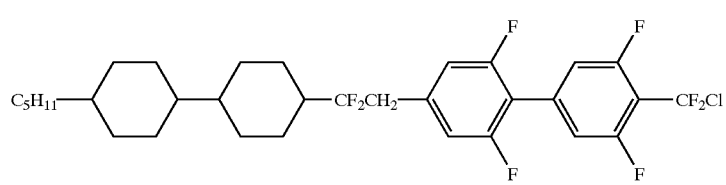 |
| 305 | 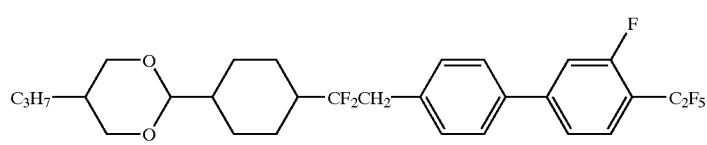 |
| 306 | 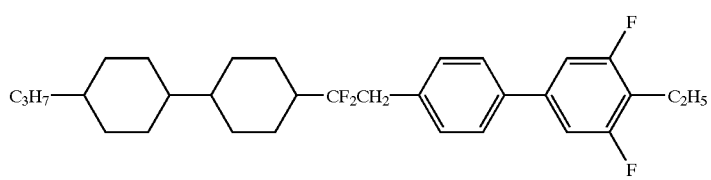 |

| No. | |
|---|---|
| 307 | 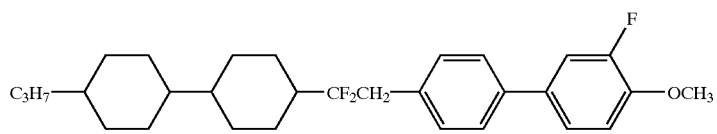 |
| 308 | 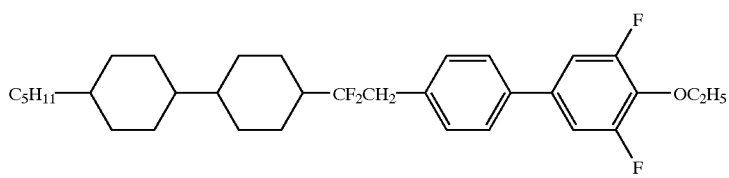 |
| 309 | 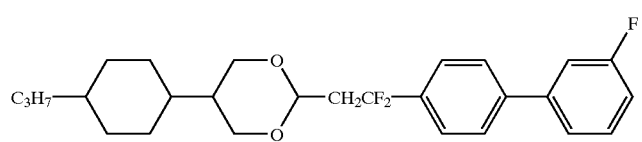 |
| 310 | 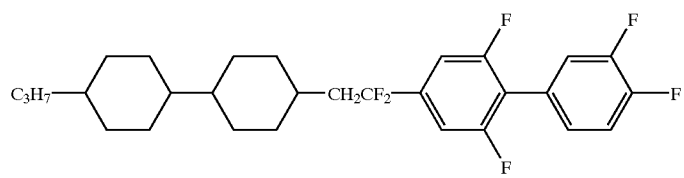 |
| 311 | 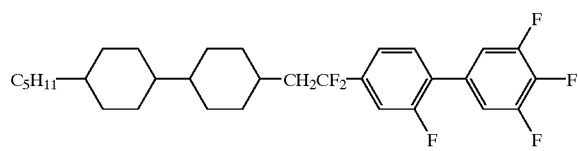 |
| 312 | 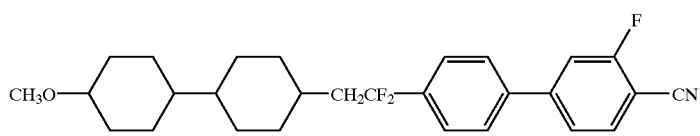 |
| 313 | 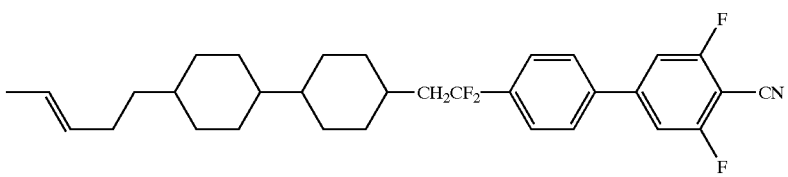 |
| 314 | 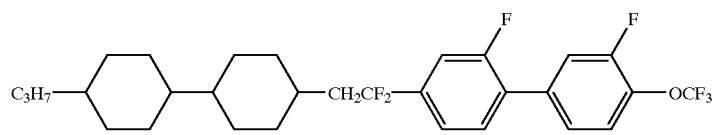 |
| 315 | 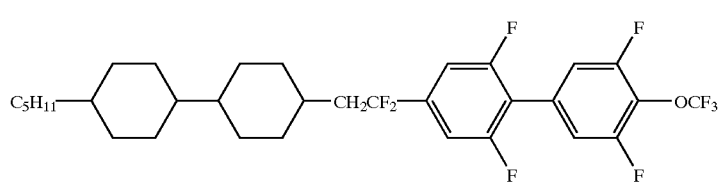 |

-continued
| No. | |
|---|---|
| 316 | 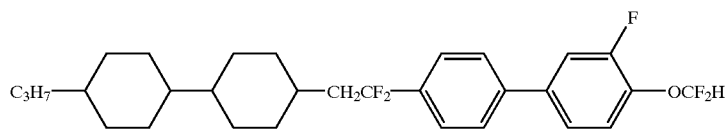 |
| 317 | 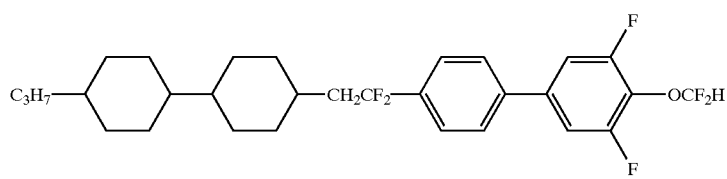 |
| 318 | 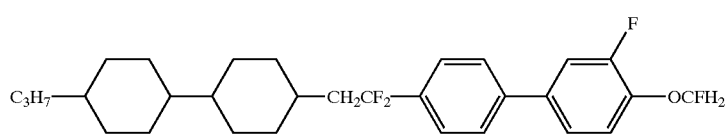 |
| 319 | 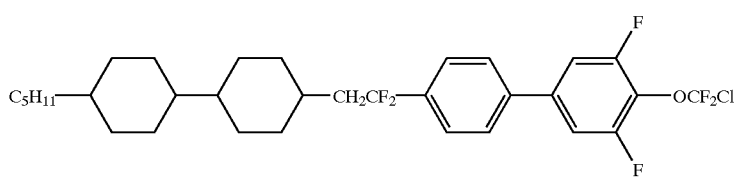 |
| 320 | 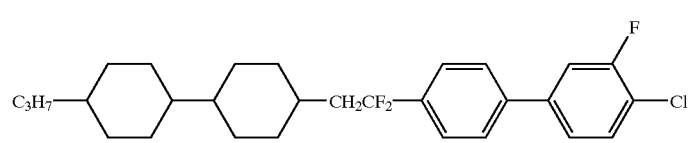 |
| 321 | 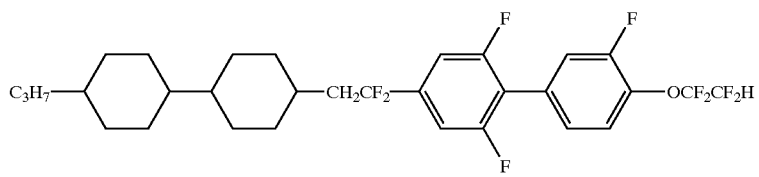 |
| 322 | 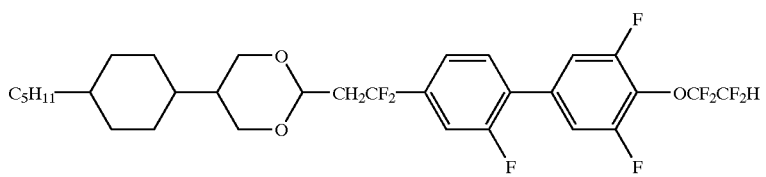 |
| 323 | 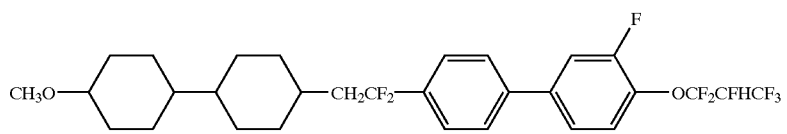 |
| 324 | 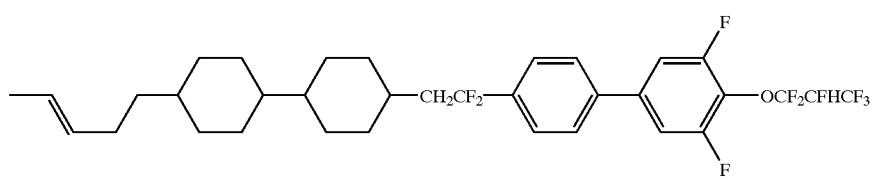 |

-continued
| No. | |
|---|---|
| 325 | 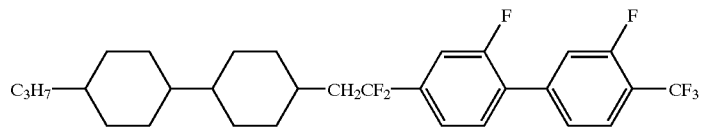 |
| 326 | 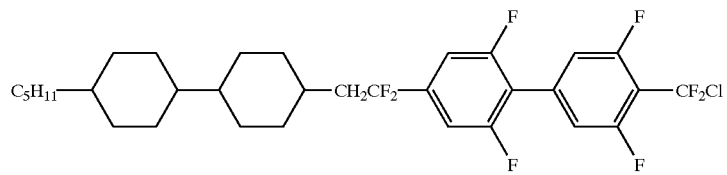 |
| 327 | 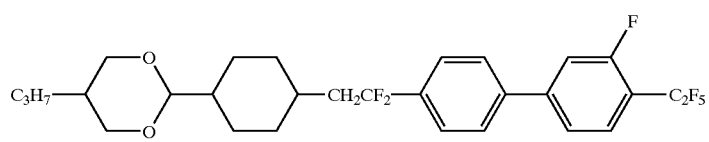 |
| 328 | 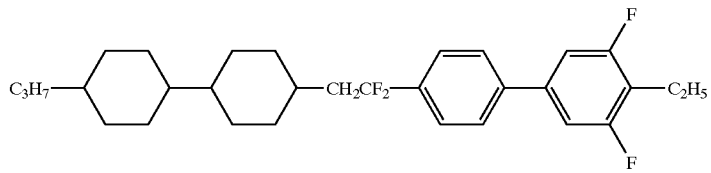 |
| 329 | 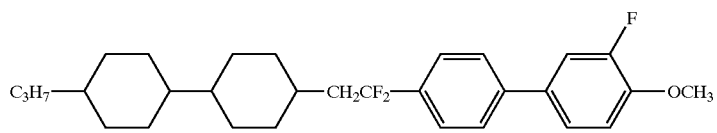 |
| 330 | 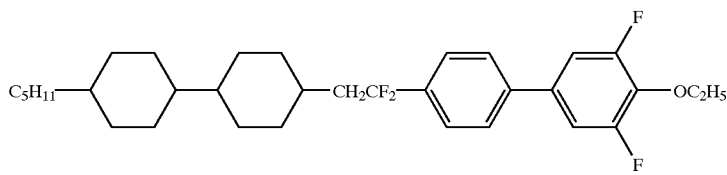 |
| 331 | 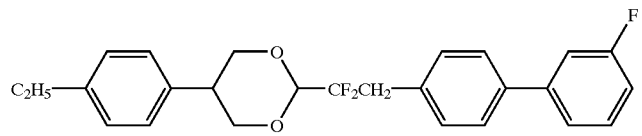 |
| 332 | 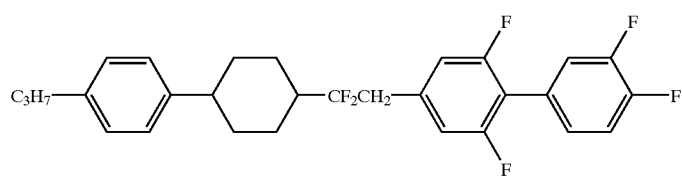 |
| 333 | 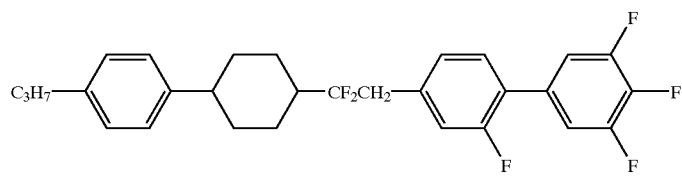 |

-continued
| No. | |
|---|---|
| 334 | 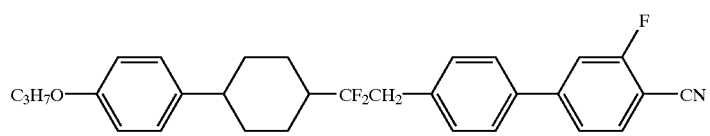 |
| 335 | 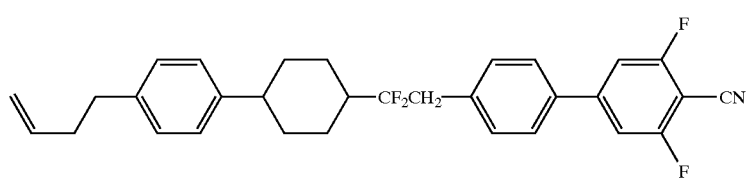 |
| 336 | 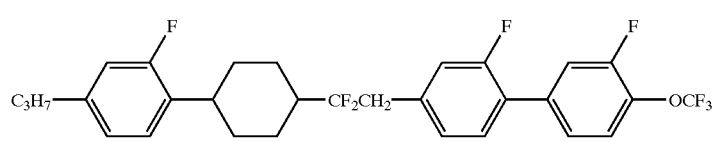 |
| 337 | 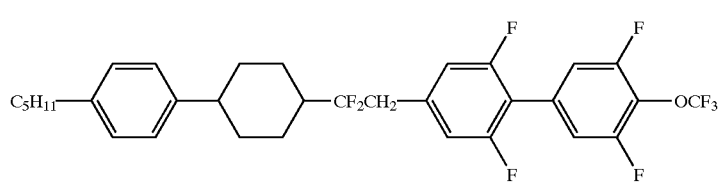 |
| 338 | 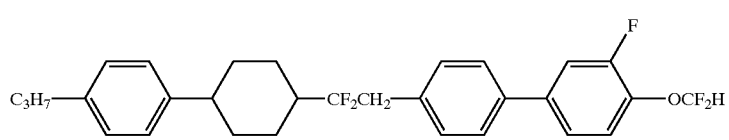 |
| 339 | 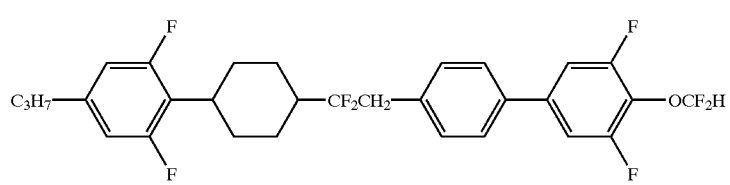 |
| 340 | 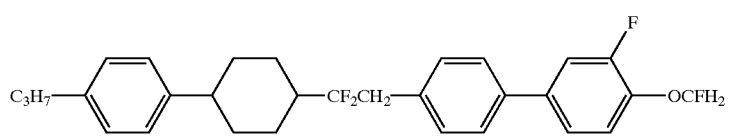 |
| 341 | 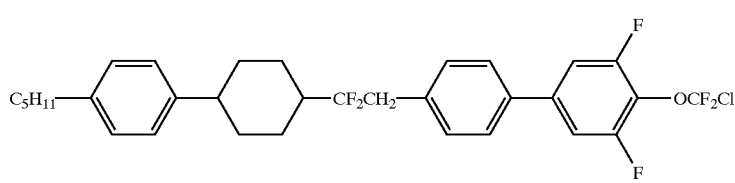 |
| 342 | 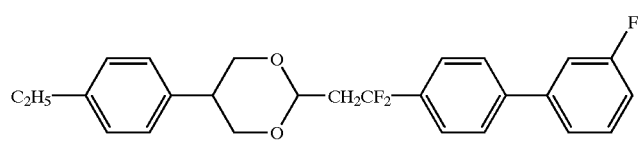 |

-continued
| No. | |
|---|---|
| 343 | 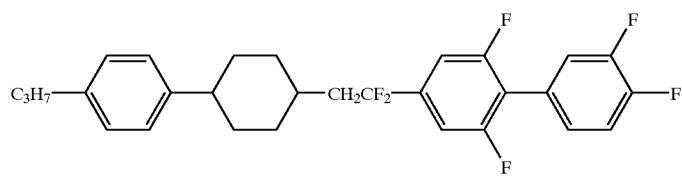 |
| 344 | 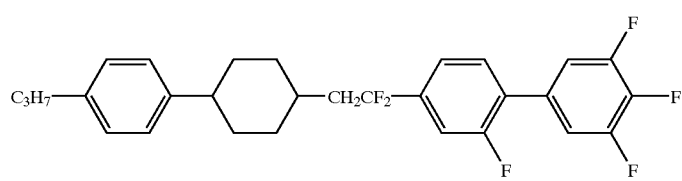 |
| 345 | 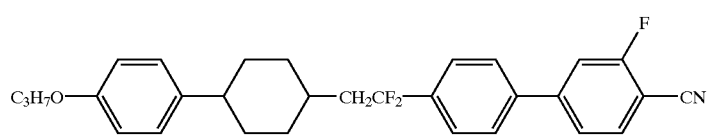 |
| 346 | 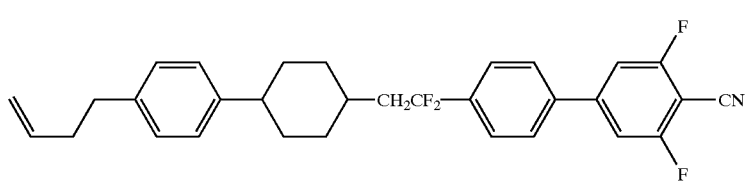 |
| 347 | 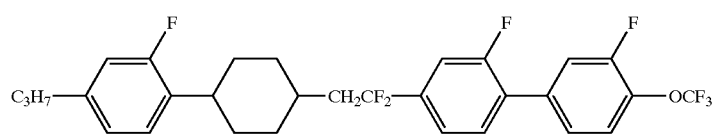 |
| 348 | 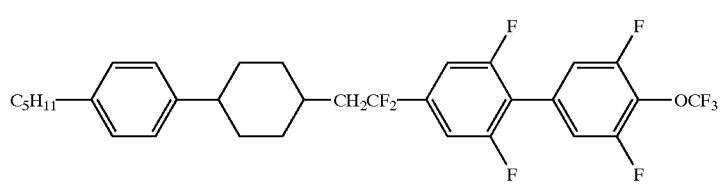 |
| 349 | 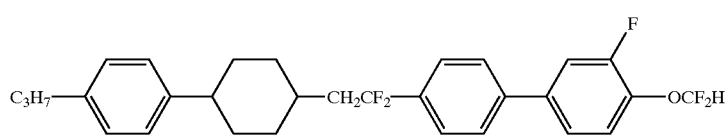 |
| 350 | 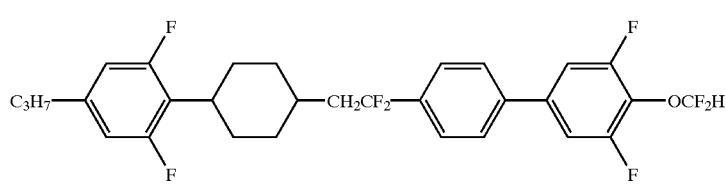 |
| 351 | 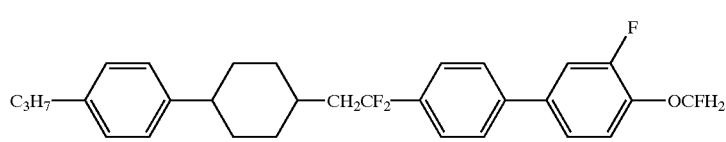 |

-continued
| No. | |
|---|---|
| 352 | 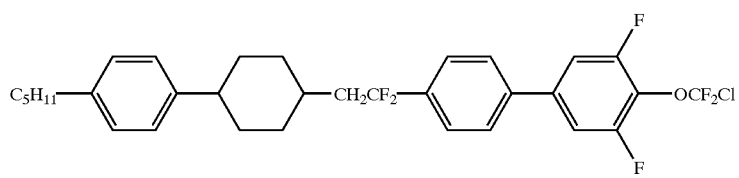 |
| 353 | 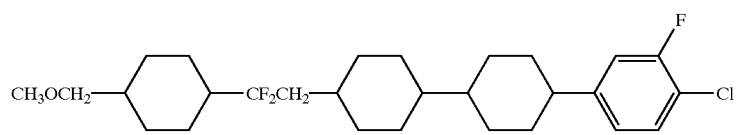 |
| 354 | 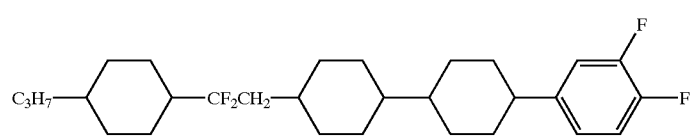 |
| 355 | 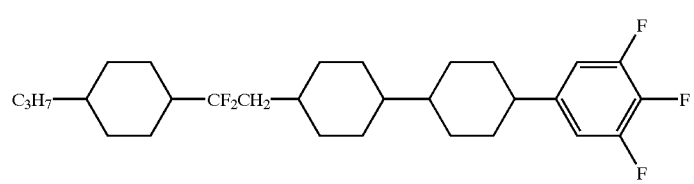 |
| 356 | 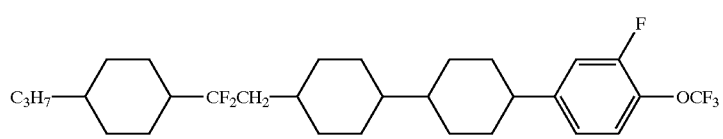 |
| 357 | 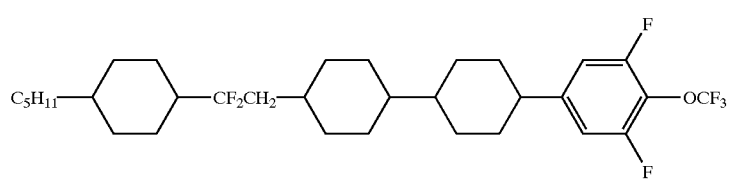 |
| 358 | 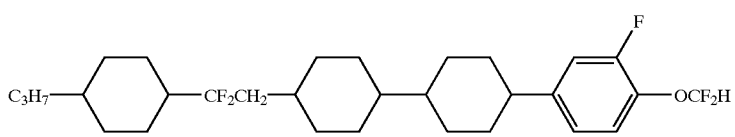 |
| 359 | 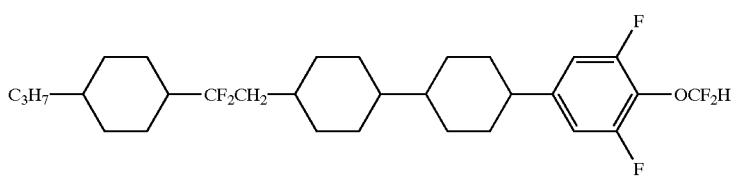 |
| 360 | 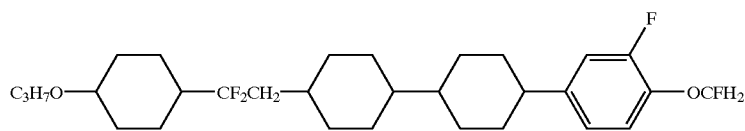 |

-continued
| No. | |
|---|---|
| 361 | 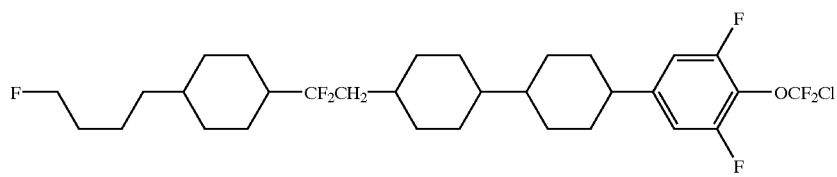 |
| 362 | 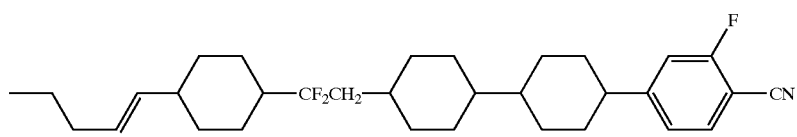 |
| 363 | 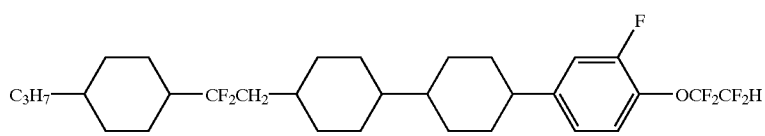 |
| 364 | 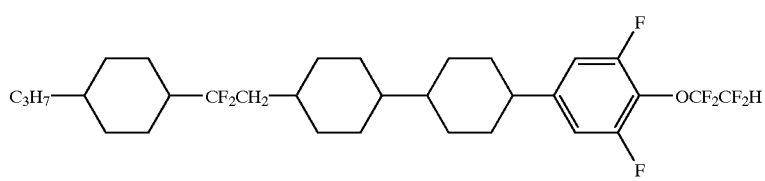 |
| 365 | 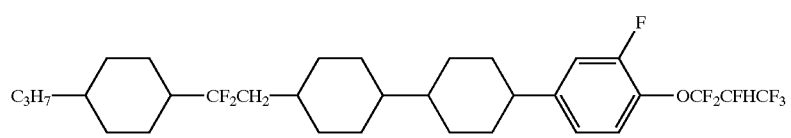 |
| 366 | 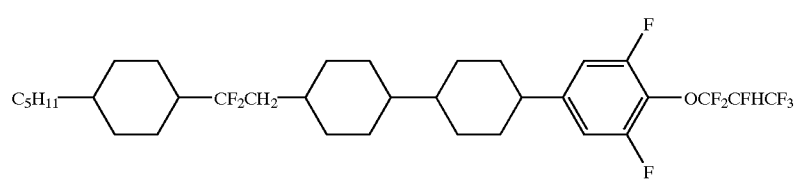 |
| 367 | 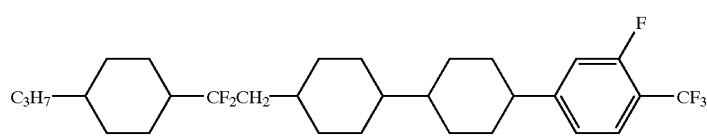 |
| 368 | 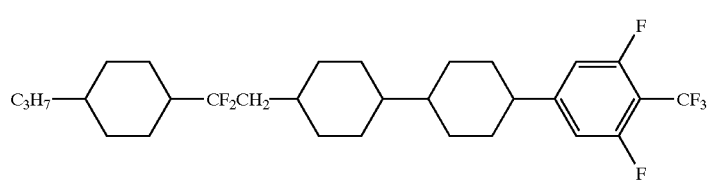 |
| 369 | 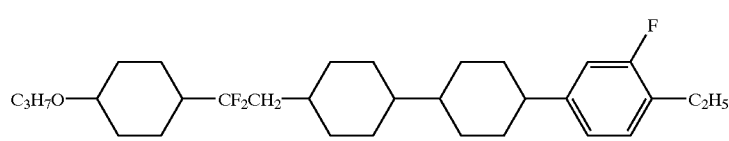 |

-continued
| No. | |
|---|---|
| 370 | 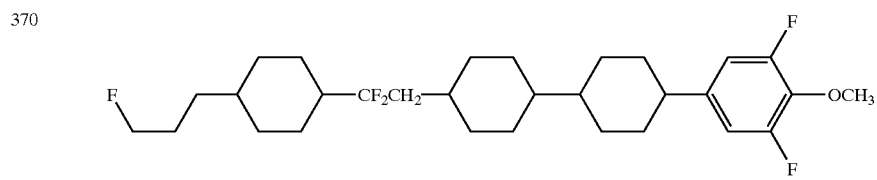 |
| 371 | 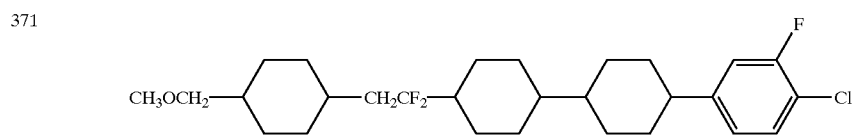 |
| 372 | 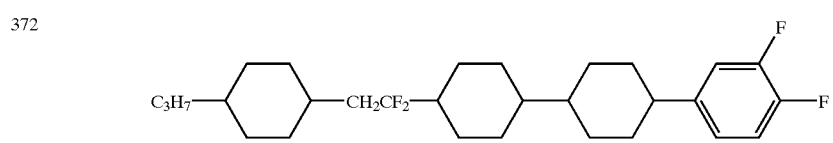 |
| 373 | 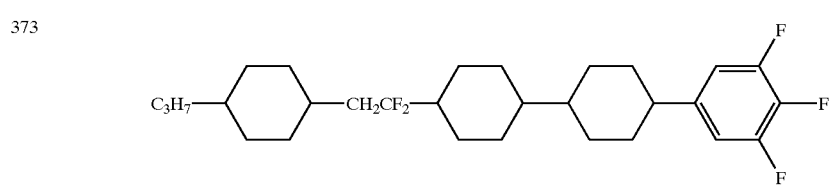 |
| 374 | 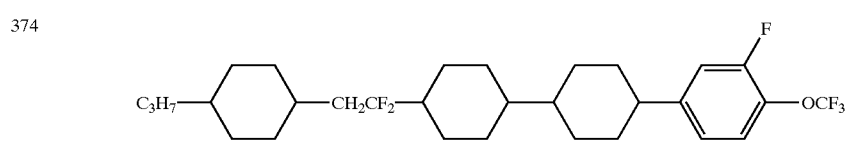 |
| 375 | 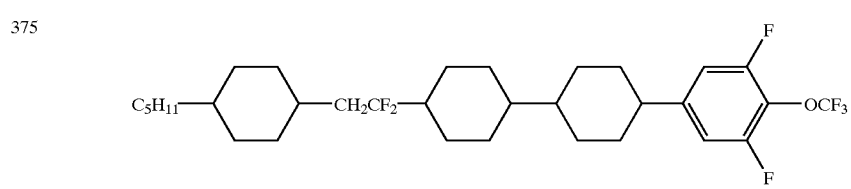 |
| 376 | 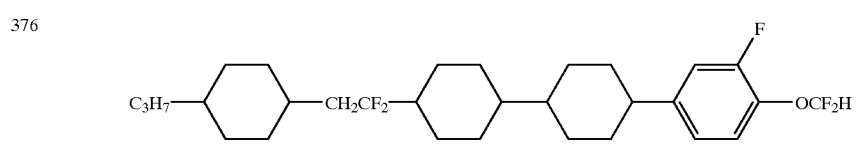 |
| 377 | 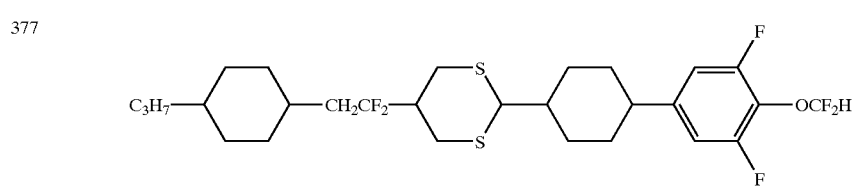 |
| 378 | 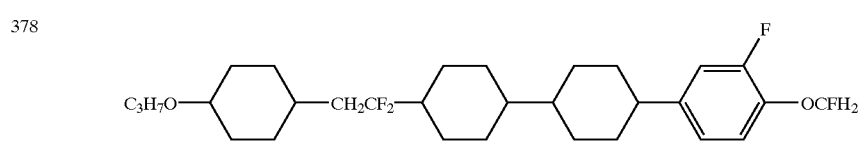 |

-continued
| No. | |
|---|---|
| 379 | 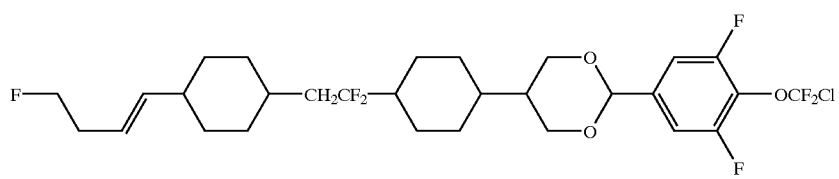 |
| 380 | 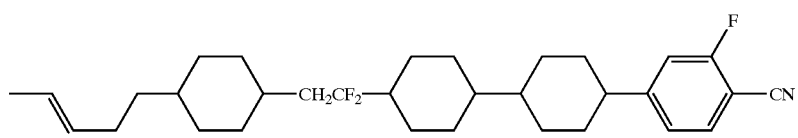 |
| 381 | 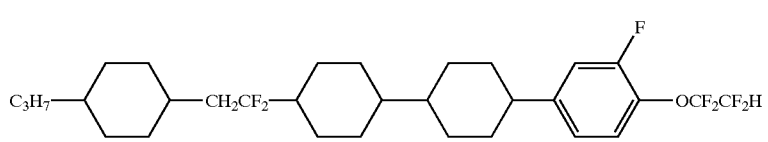 |
| 382 | 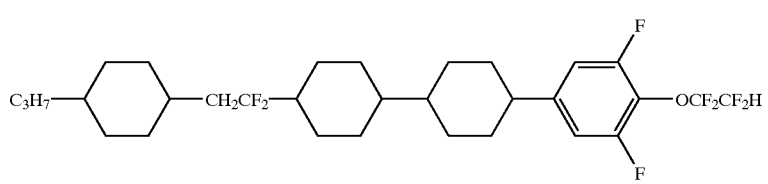 |
| 383 | 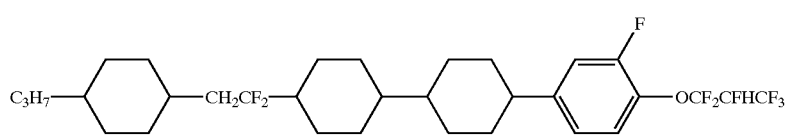 |
| 384 | 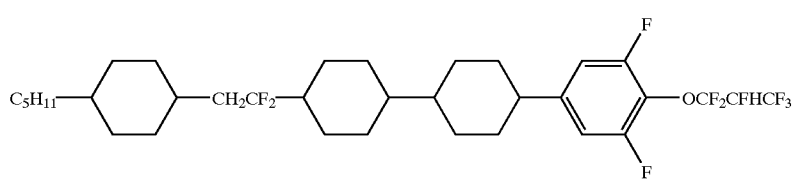 |
| 385 | 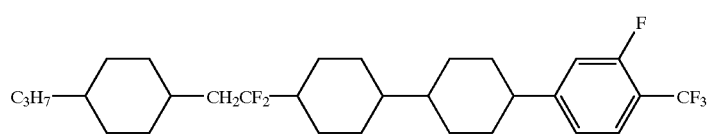 |
| 386 | 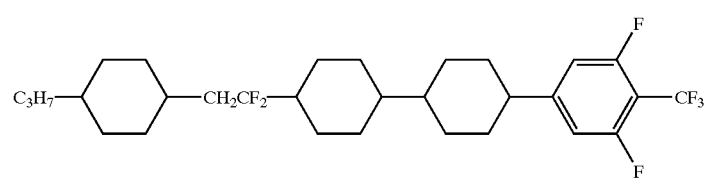 |
| 387 | 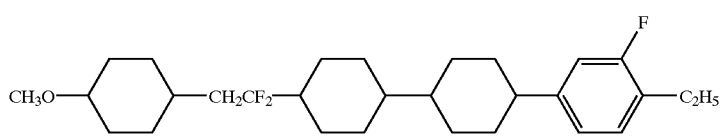 |

| No. | |
|---|---|
| 388 | 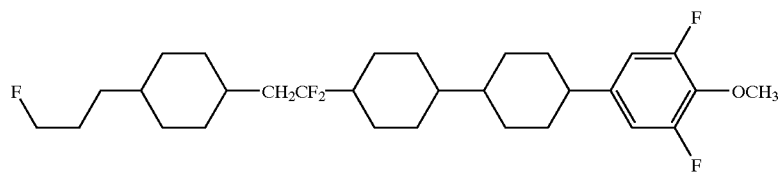 |
| 389 | 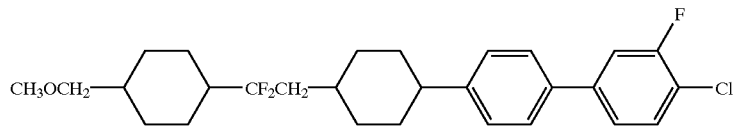 |
| 390 | 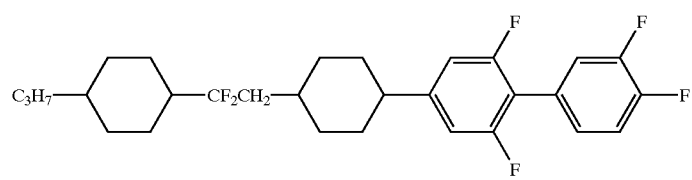 |
| 391 | 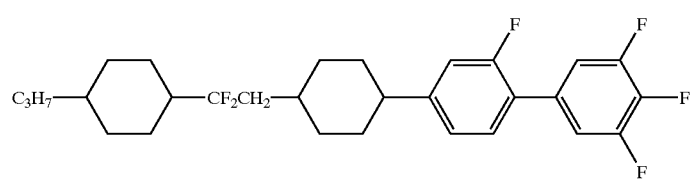 |
| 392 | 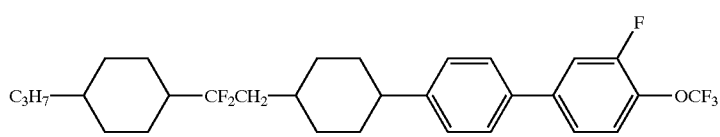 |
| 393 | 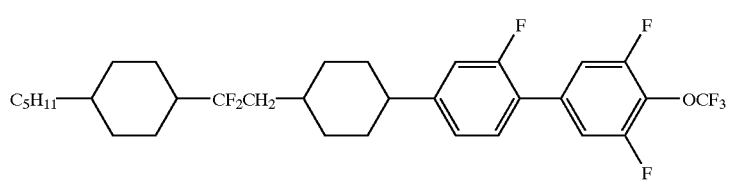 |
| 394 | 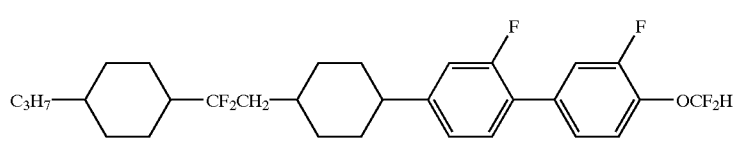 |
| 395 | 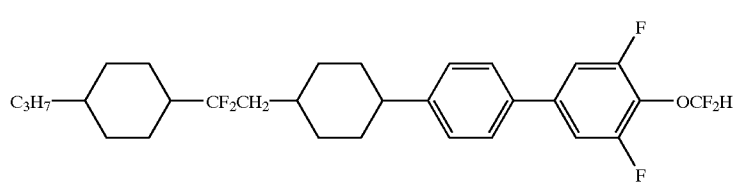 |
| 396 | 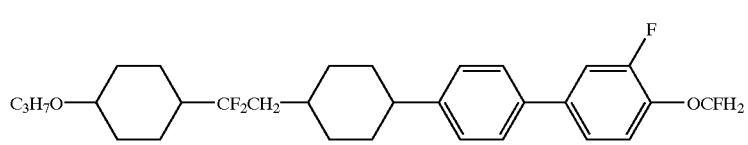 |

| No. | |
|---|---|
| 397 | 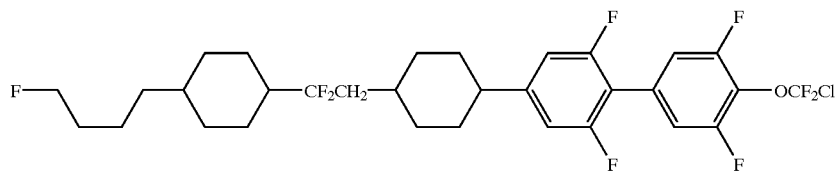 |
| 398 | 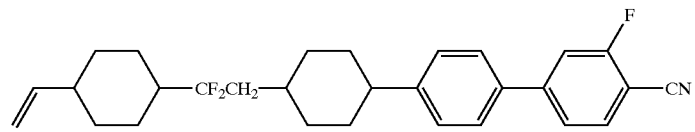 |
| 399 | 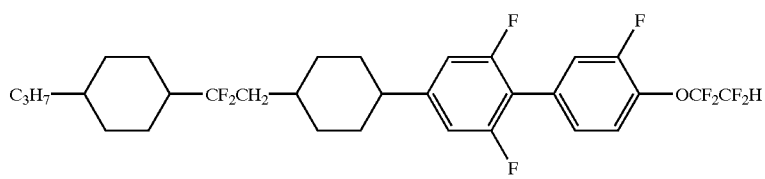 |
| 400 | 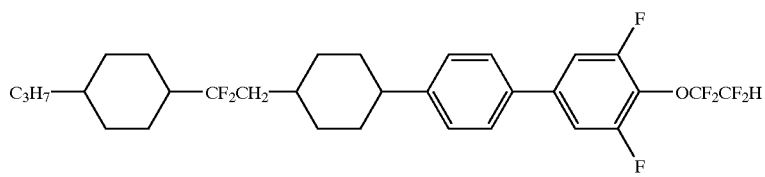 |
| 401 | 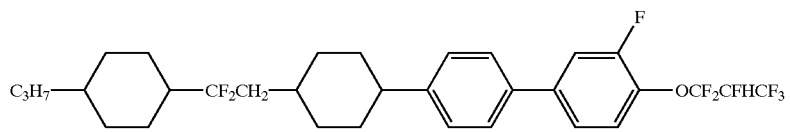 |
| 402 | 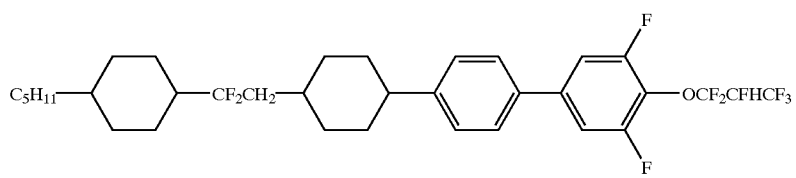 |
| 403 | 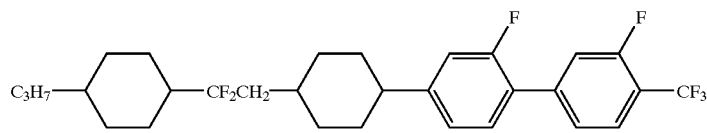 |
| 404 | 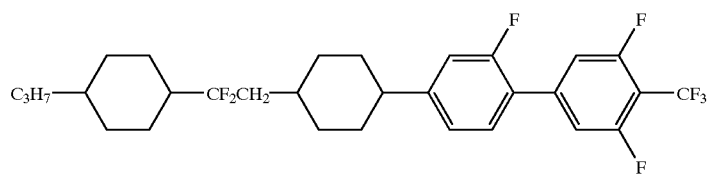 |
| 405 | 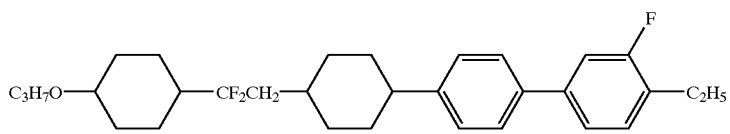 |

| No. | |
|---|---|
| 406 | 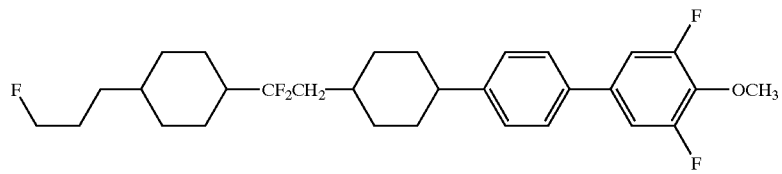 |
| 407 | 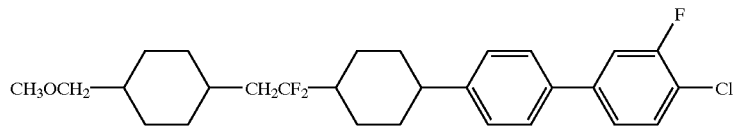 |
| 408 | 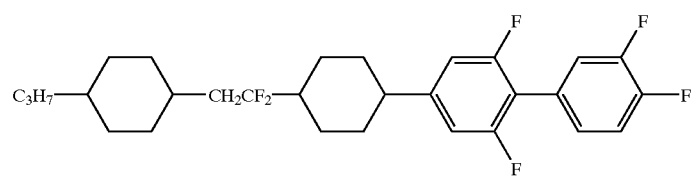 |
| 409 | 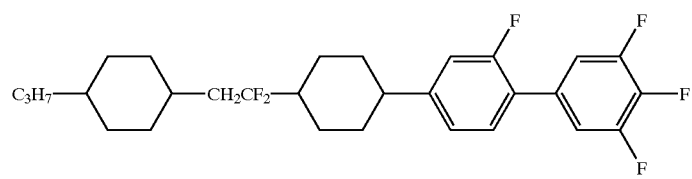 |
| 410 | 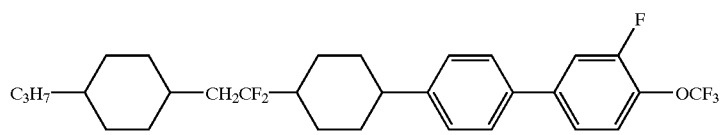 |
| 411 | 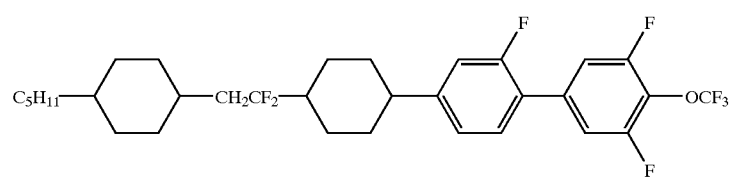 |
| 412 | 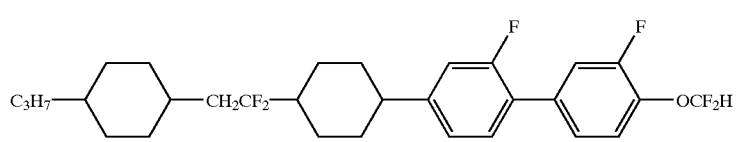 |
| 413 | 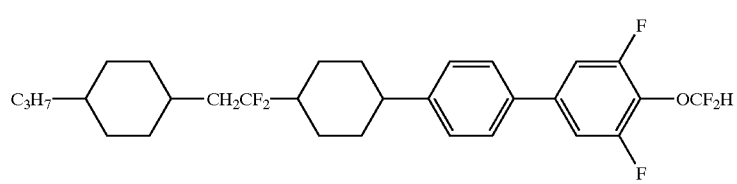 |
| 414 | 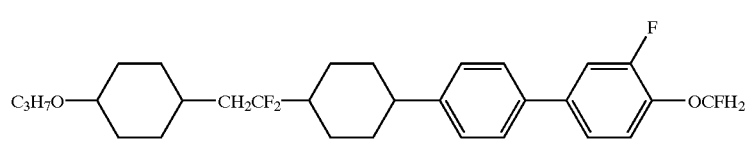 |

-continued
| No. | |
|---|---|
| 415 | 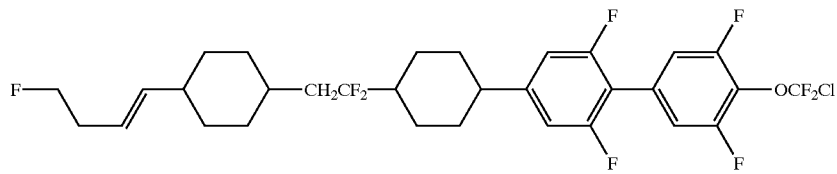 |
| 416 | 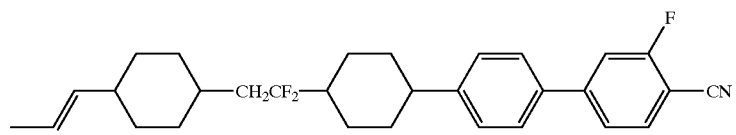 |
| 417 | 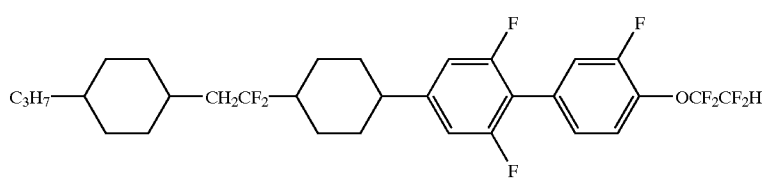 |
| 418 | 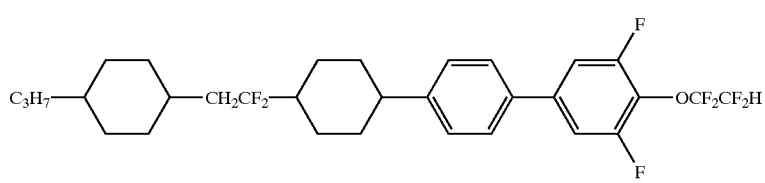 |
| 419 | 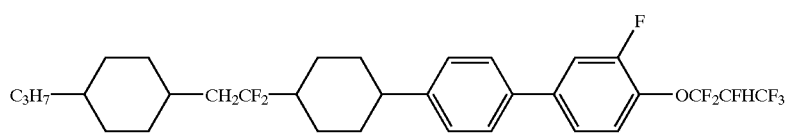 |
| 420 | 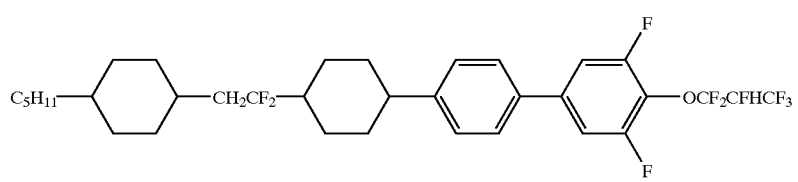 |
| 421 | 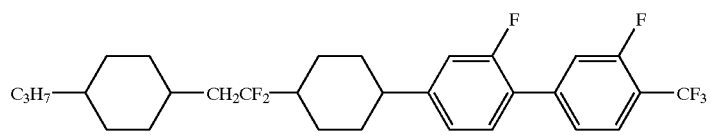 |
| 422 | 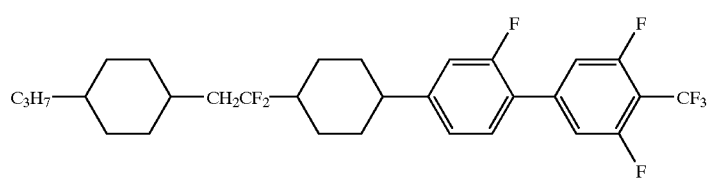 |
| 423 | 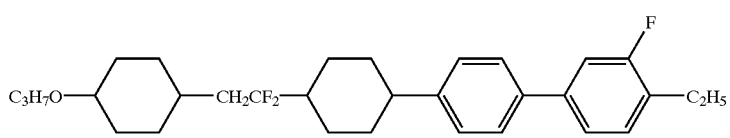 |

| No. | |
|---|---|
| 424 | 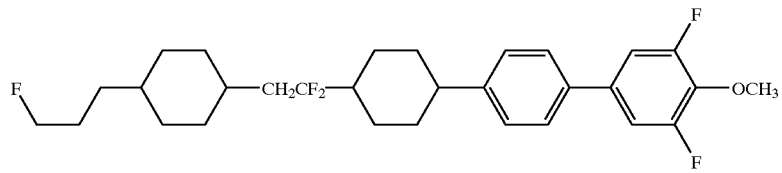 |
| 425 | 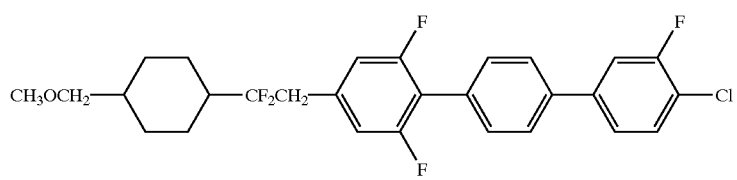 |
| 426 | 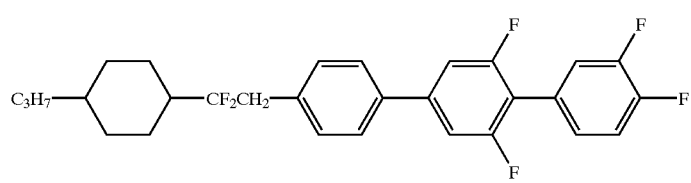 |
| 427 | 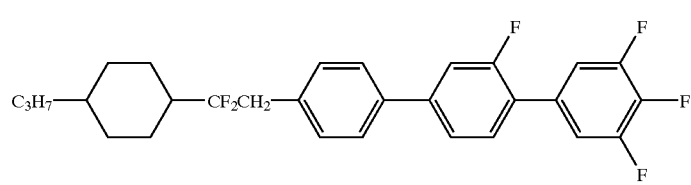 |
| 428 | 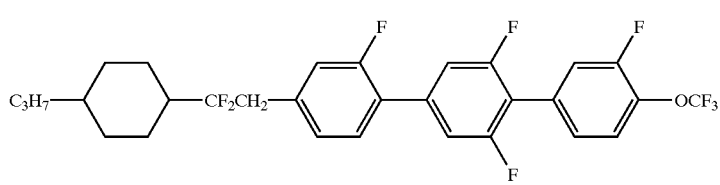 |
| 429 | 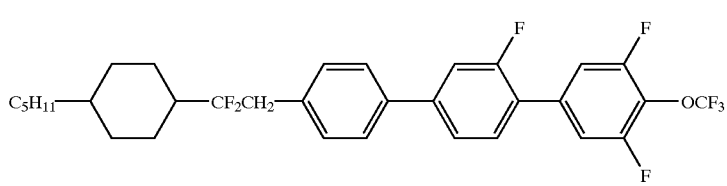 |
| 430 | 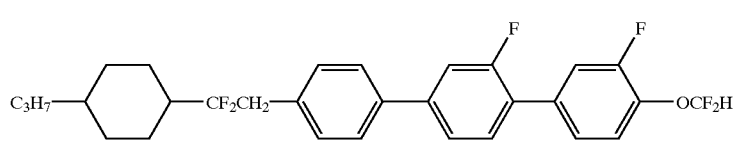 |
| 431 | 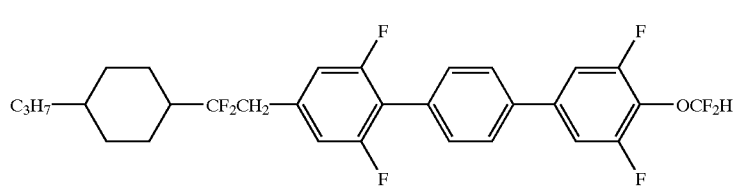 |

-continued
| No. | |
|---|---|
| 432 | 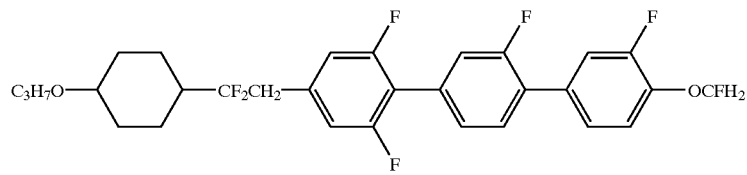 |
| 433 | 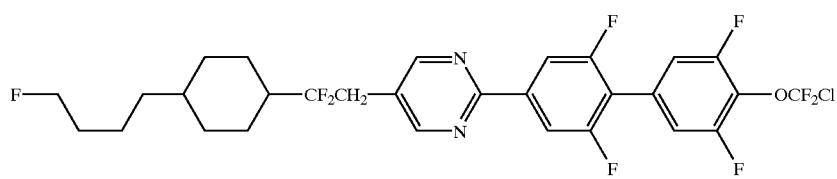 |
| 434 | 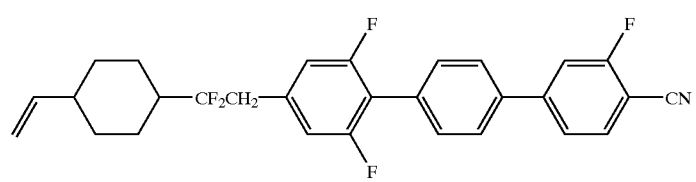 |
| 435 | 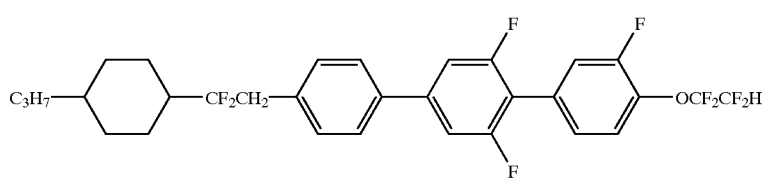 |
| 436 | 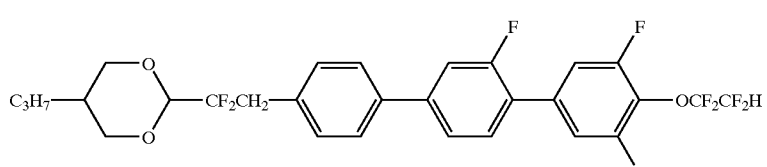 |
| 437 | 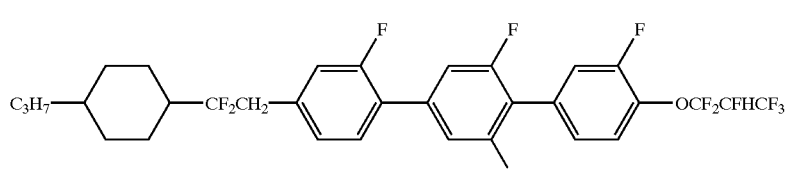 |
| 438 | 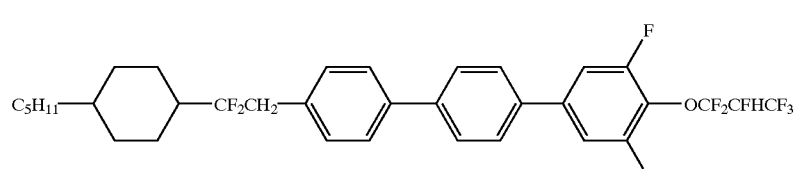 |
| 439 | 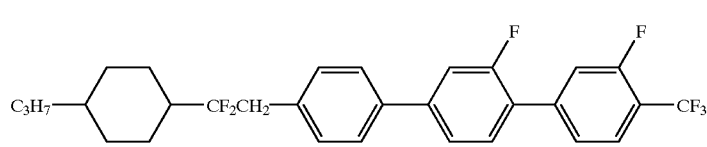 |

| No. | |
|---|---|
| 440 | 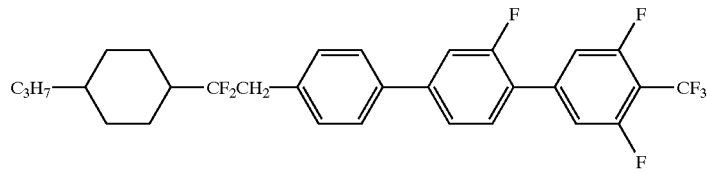 |
| 441 | 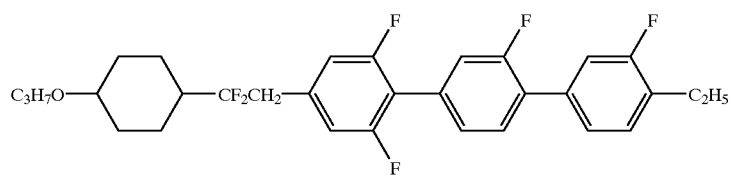 |
| 442 | 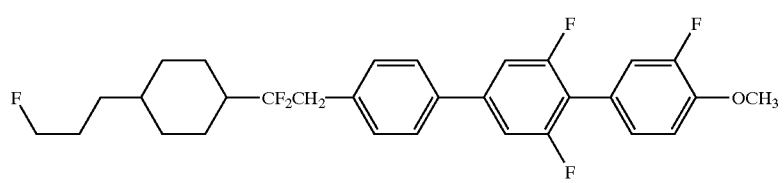 |
| 443 | 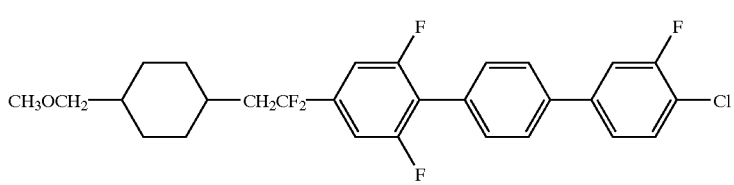 |
| 444 | 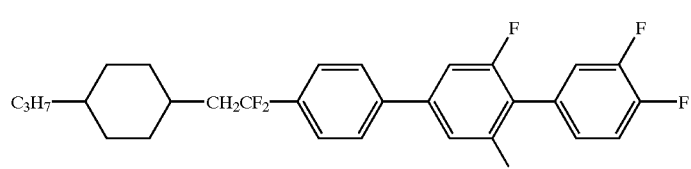 |
| 445 | 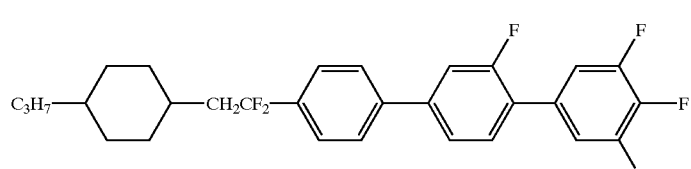 |
| 446 | 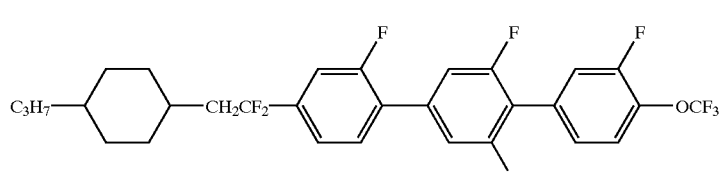 |
| 447 | 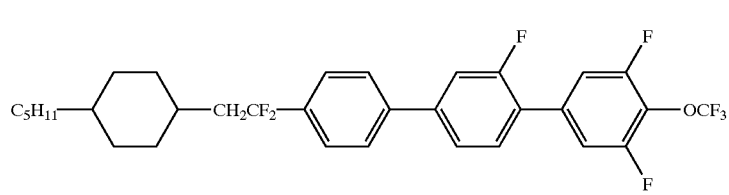 |

-continued
| No. | |
|---|---|
| 448 | 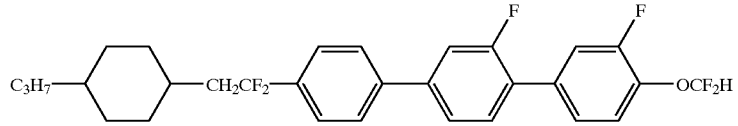 |
| 449 | 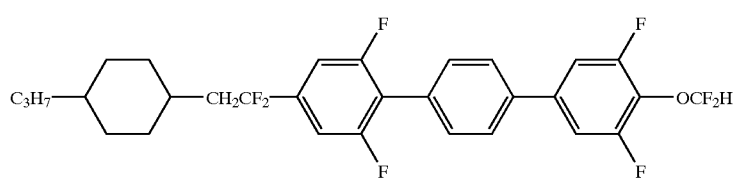 |
| 450 | 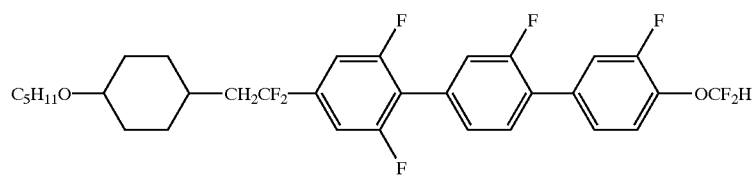 |
| 451 | 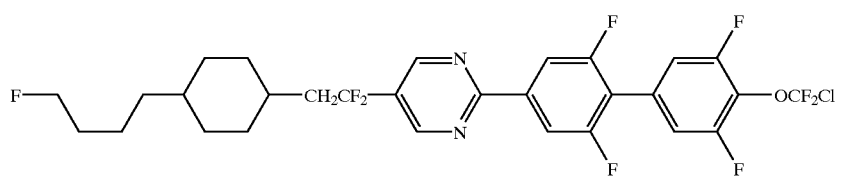 |
| 452 | 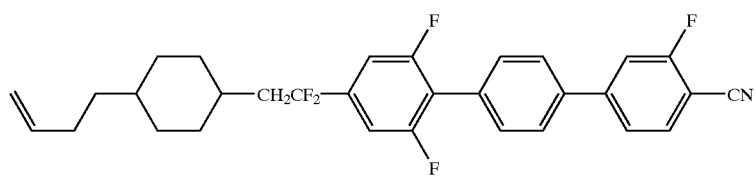 |
| 453 | 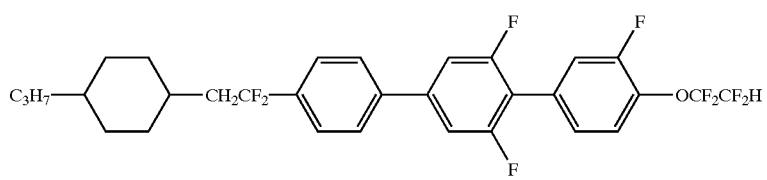 |
| 454 | 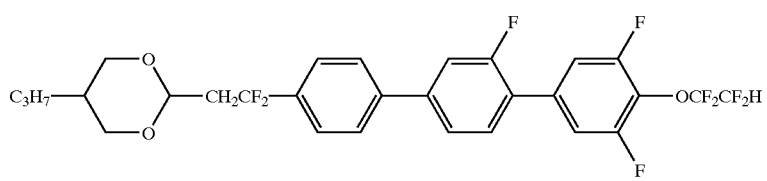 |
| 455 | 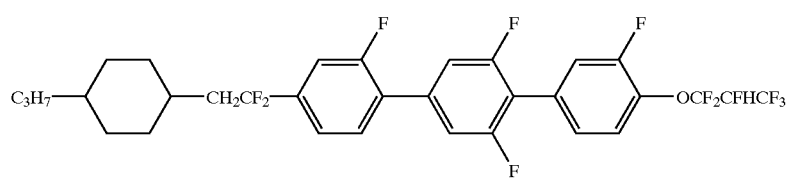 |

-continued
| No. | |
|---|---|
| 456 | 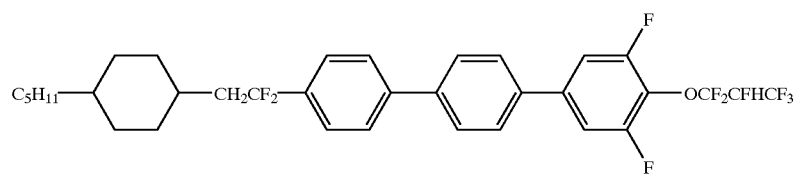 |
| 457 | 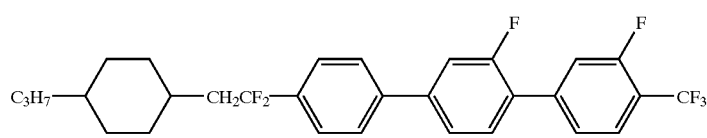 |
| 458 | 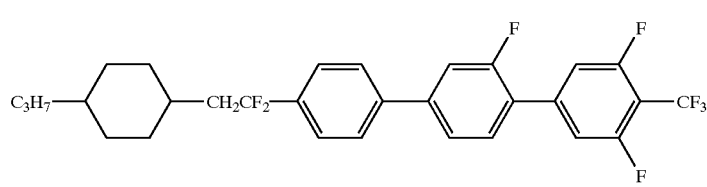 |
| 459 | 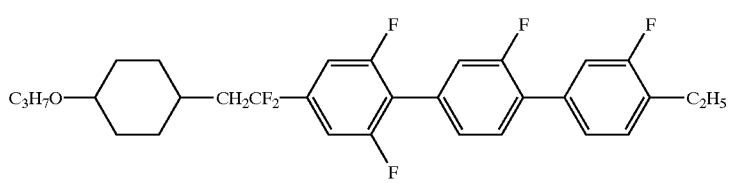 |
| 460 | 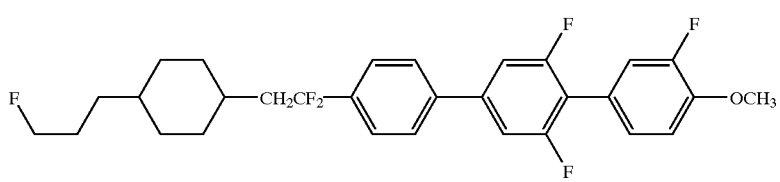 |
| 461 | 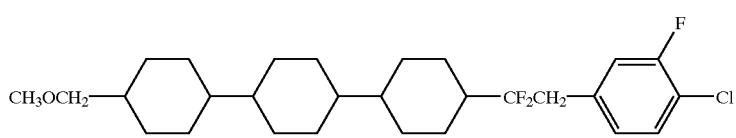 |
| 462 | 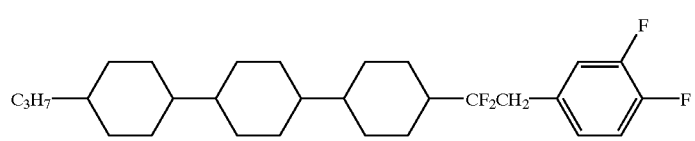 |
| 463 | 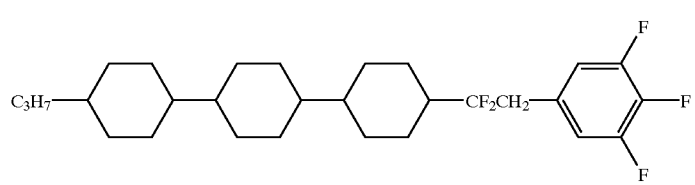 |
| 464 | 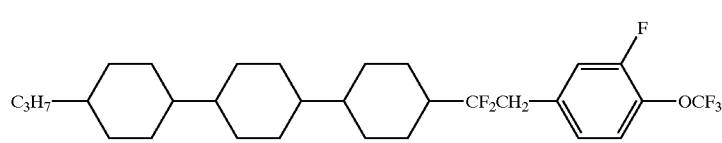 |

-continued
| No. | |
|---|---|
| 465 | 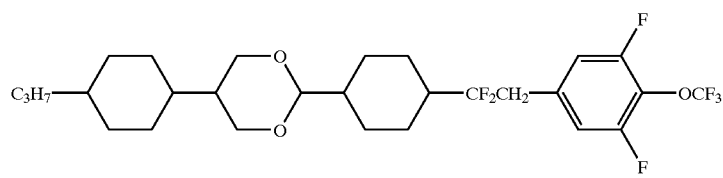 |
| 466 | 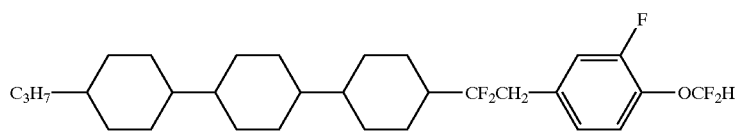 |
| 467 | 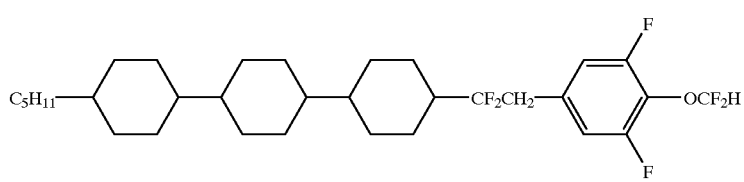 |
| 468 | 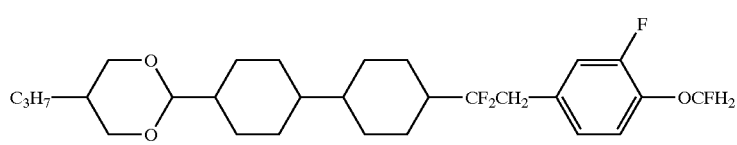 |
| 469 | 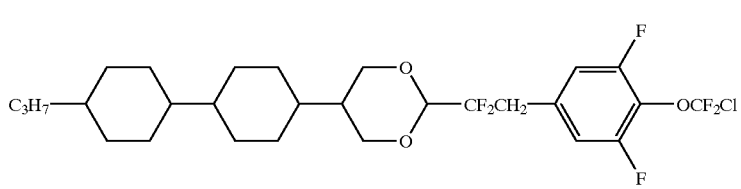 |
| 470 | 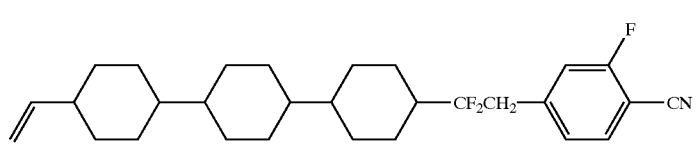 |
| 471 | 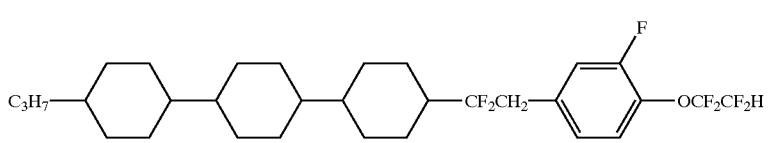 |
| 472 | 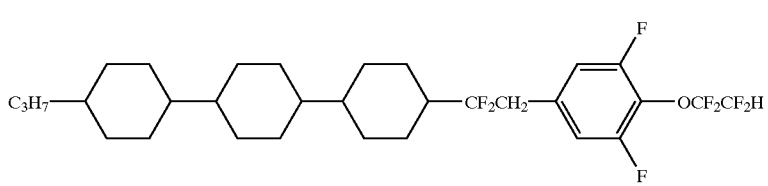 |
| 473 | 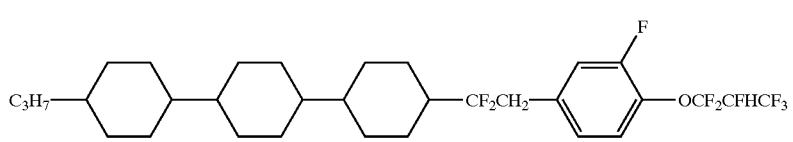 |

-continued
| No. | |
|---|---|
| 474 | 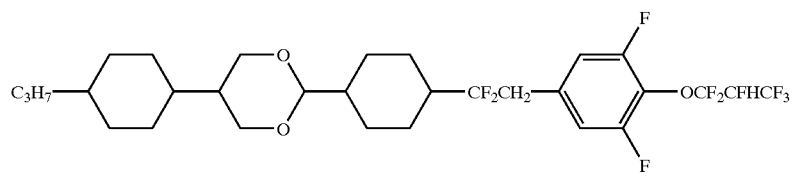 |
| 475 | 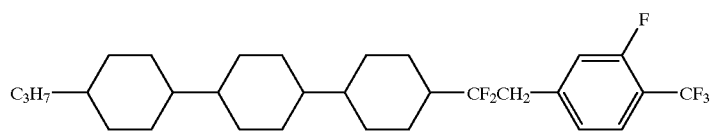 |
| 476 | 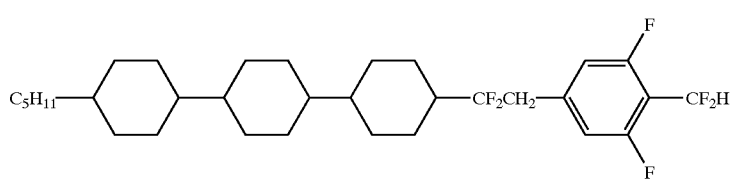 |
| 477 | 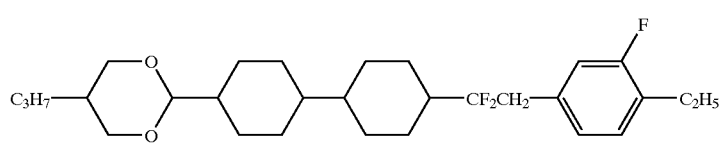 |
| 478 | 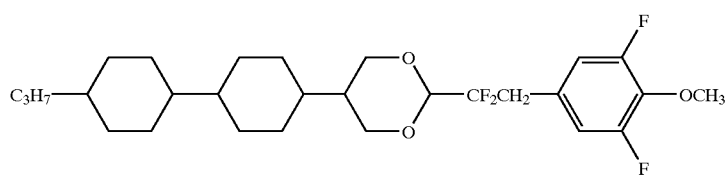 |
| 479 | 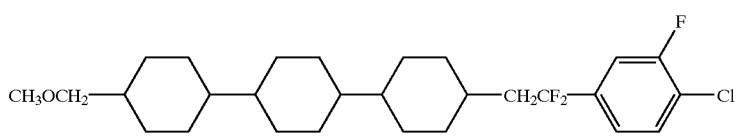 |
| 480 | 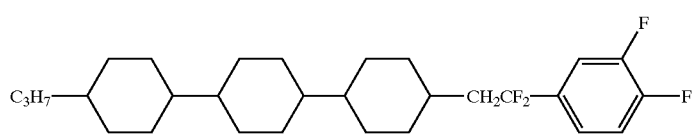 |
| 481 | 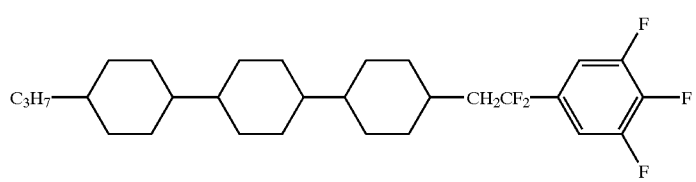 |
| 482 | 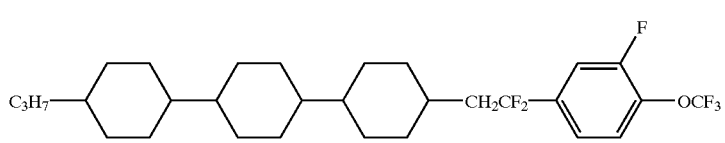 |

| No. | |
|---|---|
| 483 | 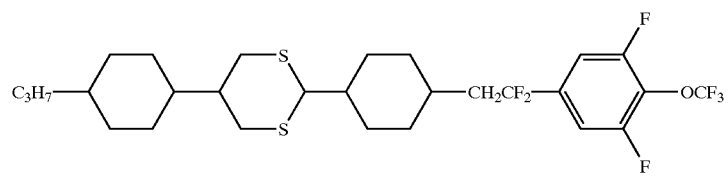 |
| 484 | 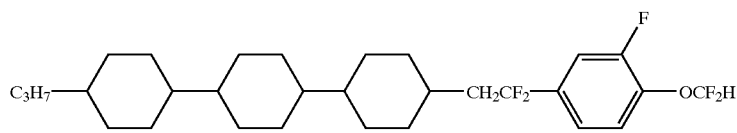 |
| 485 | 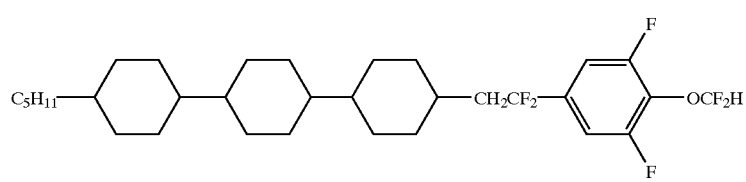 |
| 486 | 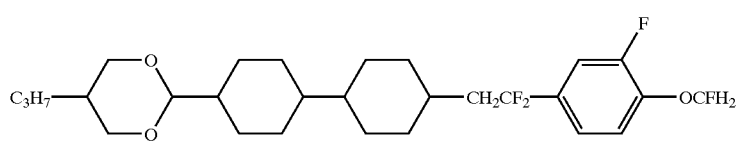 |
| 487 | 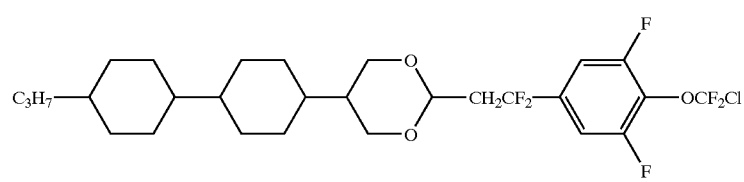 |
| 488 | 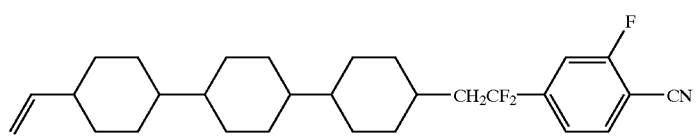 |
| 489 | 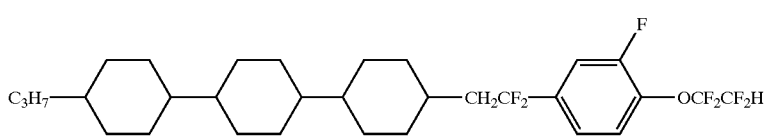 |
| 490 | 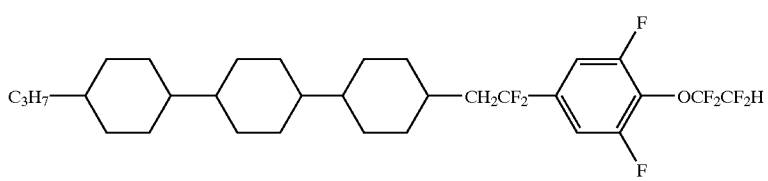 |
| 491 | 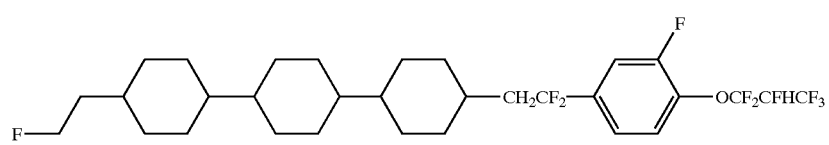 |

-continued
| No. | |
|---|---|
| 492 | 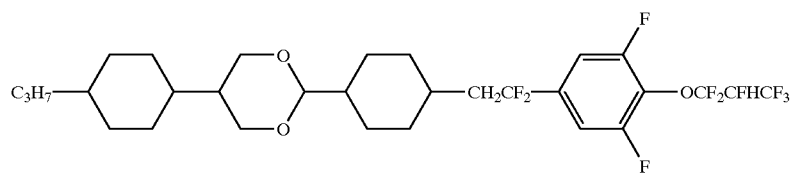 |
| 493 | 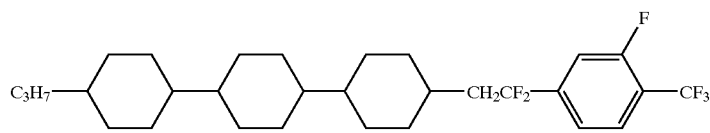 |
| 494 | 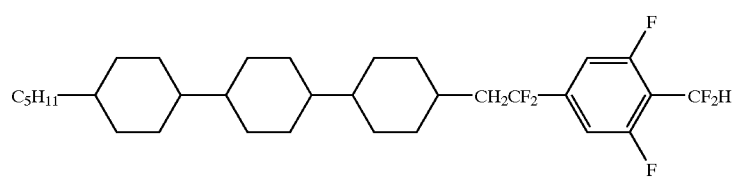 |
| 495 | 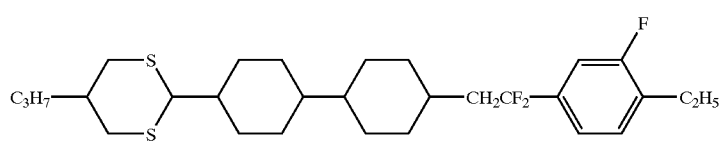 |
| 496 | 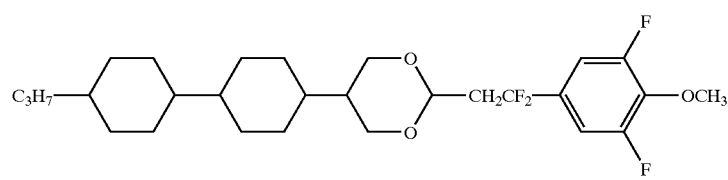 |
| 497 | 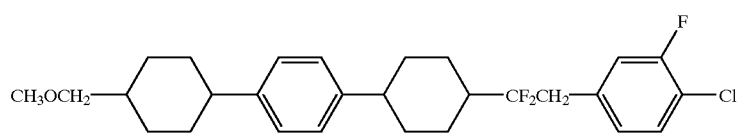 |
| 498 | 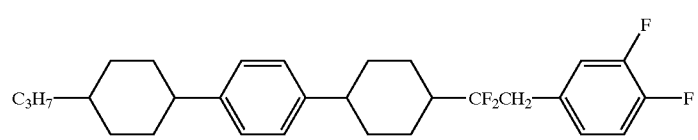 |
| 499 | 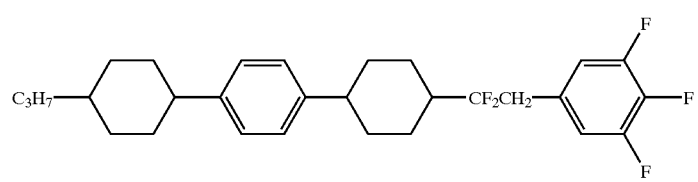 |
| 500 | 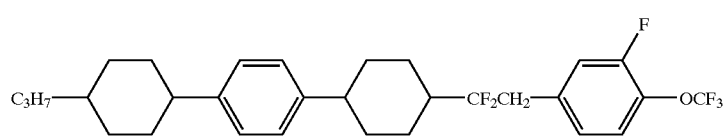 |

-continued
| No. | |
|---|---|
| 501 | 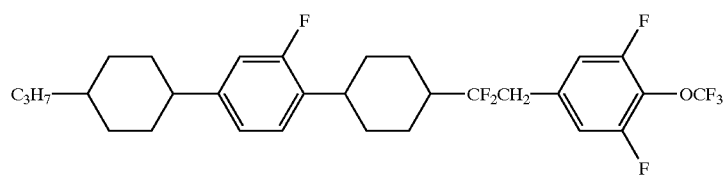 |
| 502 | 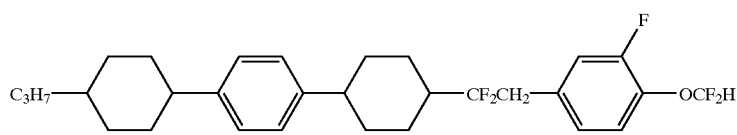 |
| 503 | 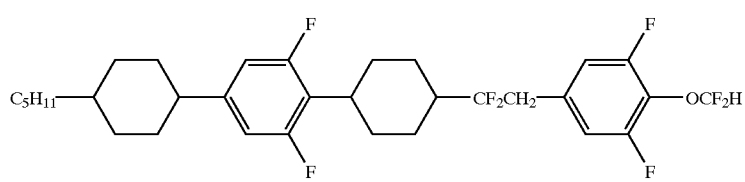 |
| 504 | 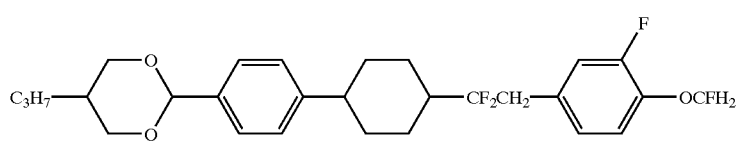 |
| 505 | 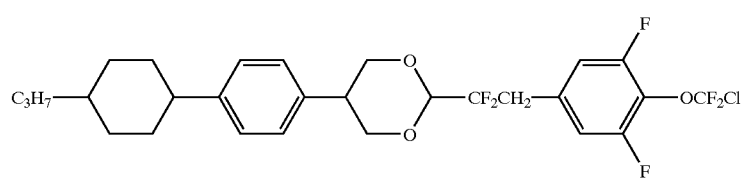 |
| 506 | 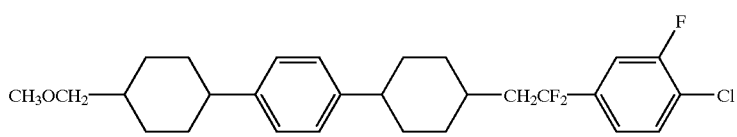 |
| 507 | 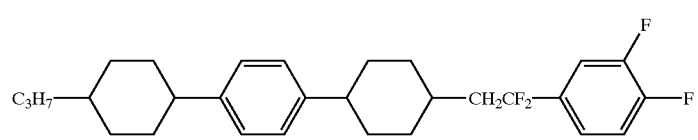 |
| 508 | 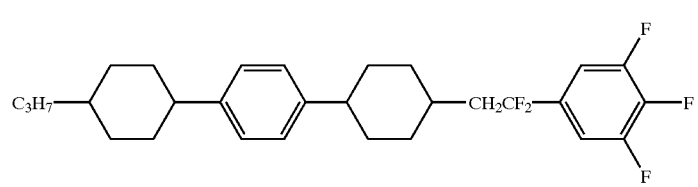 |
| 509 | 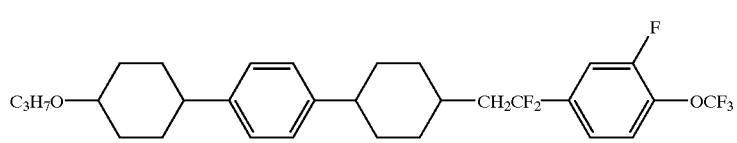 |

| No. | |
|---|---|
| 510 | 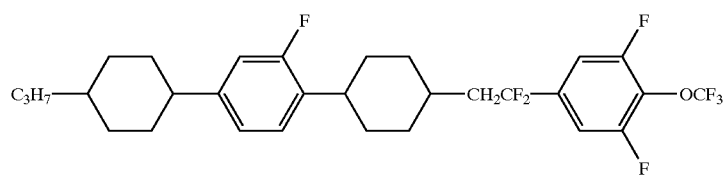 |
| 511 | 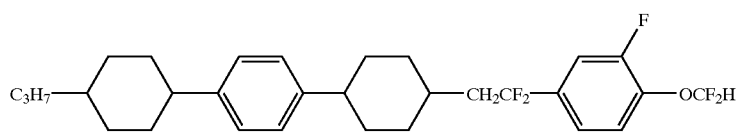 |
| 512 | 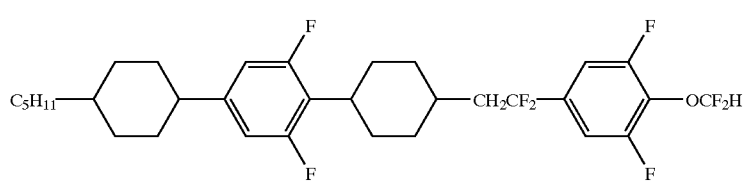 |
| 513 | 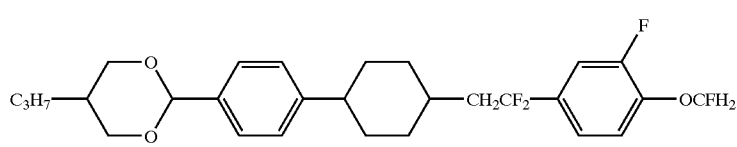 |
| 514 | 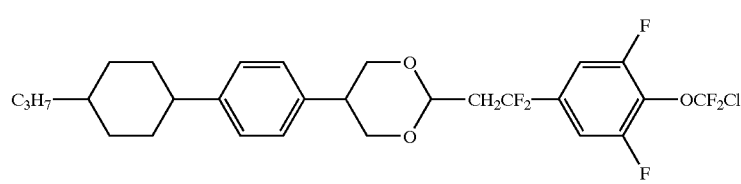 |
| 515 | 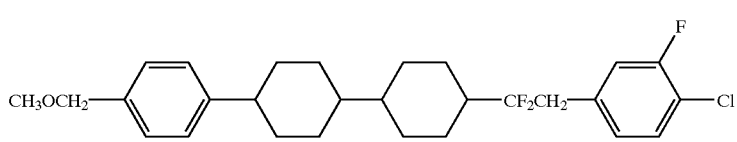 |
| 516 | 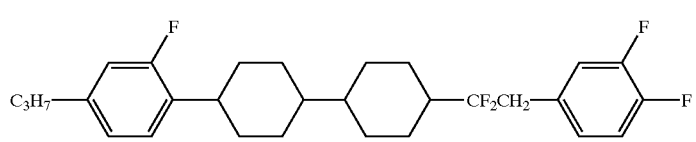 |
| 517 | 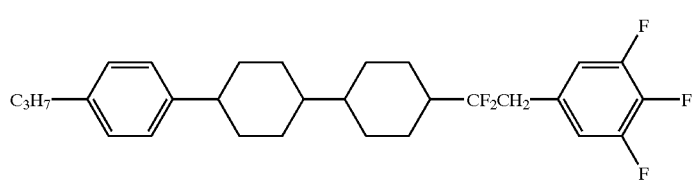 |
| 518 | 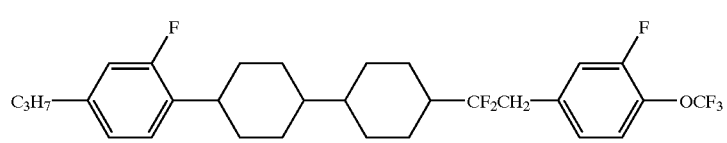 |

-continued
| No. | |
|---|---|
| 519 | 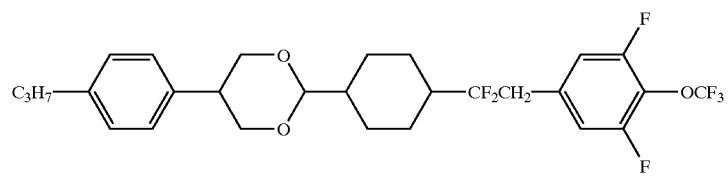 |
| 520 | 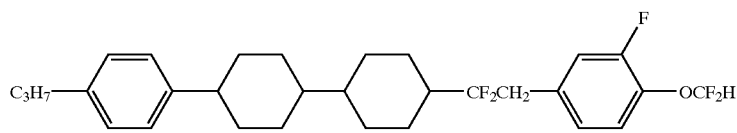 |
| 521 | 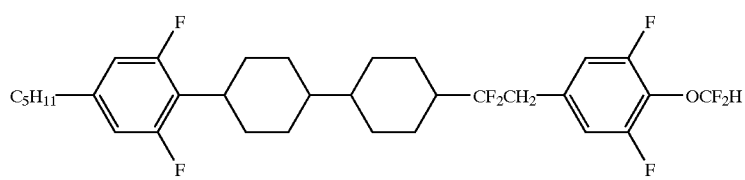 |
| 522 | 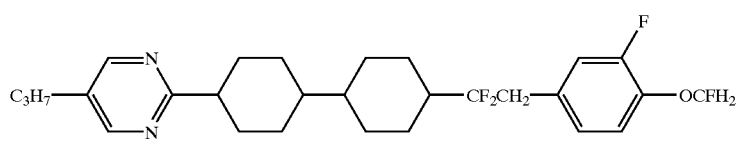 |
| 523 | 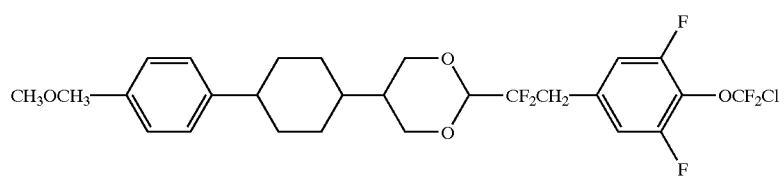 |
| 524 | 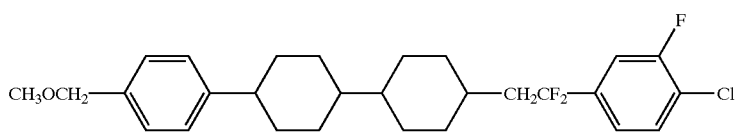 |
| 525 | 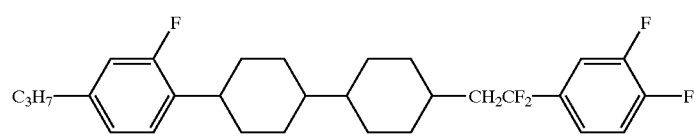 |
| 526 | 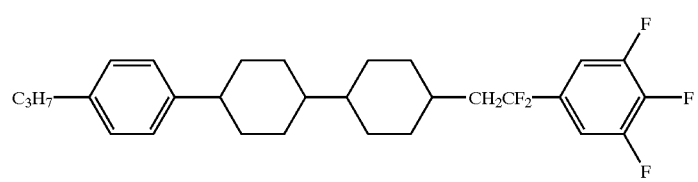 |
| 527 | 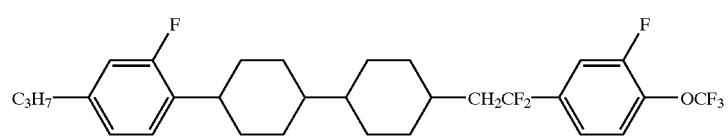 |

| No. | |
|---|---|
| 528 | 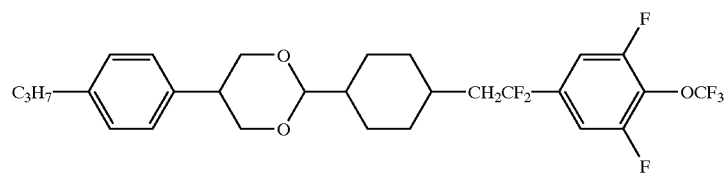 |
| 529 | 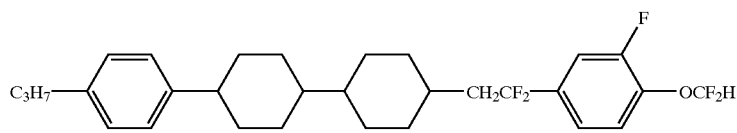 |
| 530 | 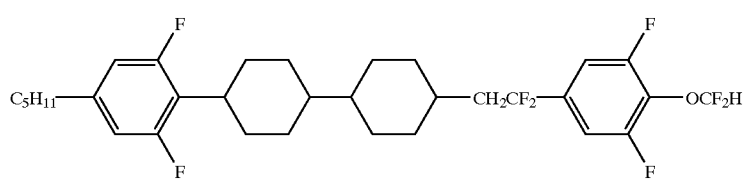 |
| 531 | 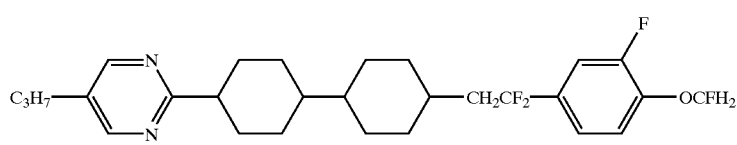 |
| 532 | 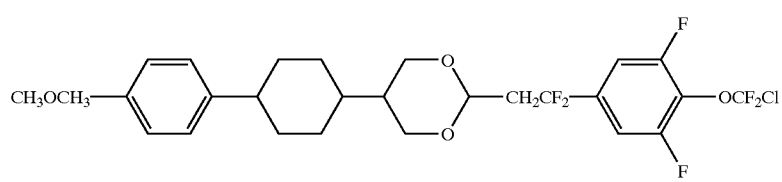 |
| 533 | 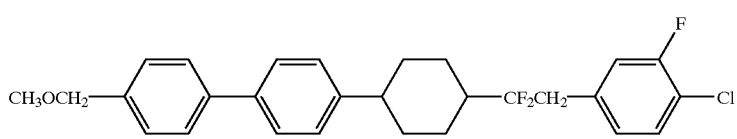 |
| 534 | 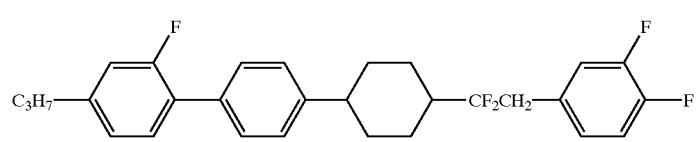 |
| 535 | 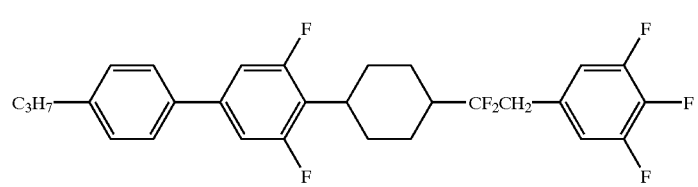 |
| 536 | 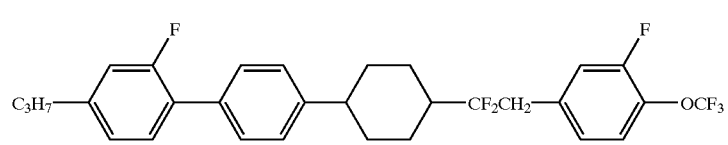 |

-continued
| No. | |
|---|---|
| 537 | 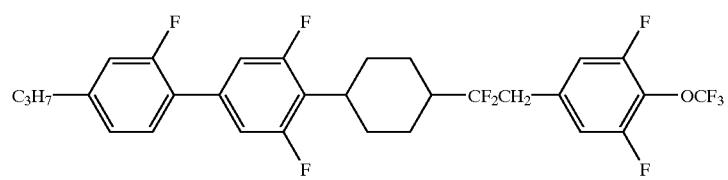 |
| 538 | 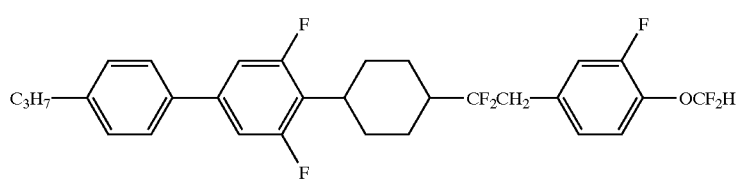 |
| 539 | 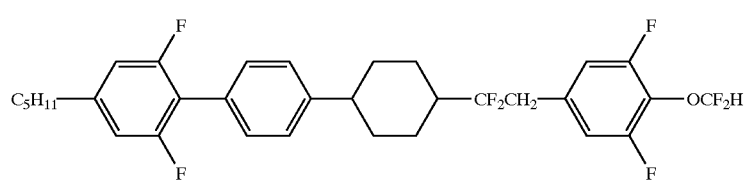 |
| 540 | 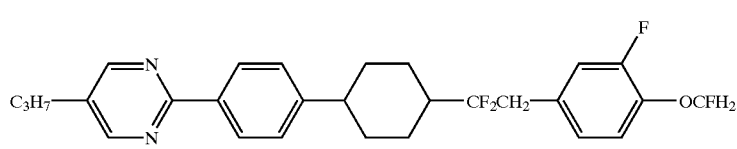 |
| 541 | 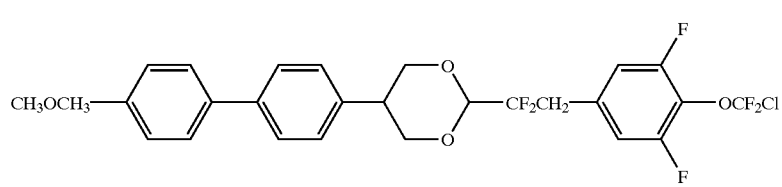 |
| 542 | 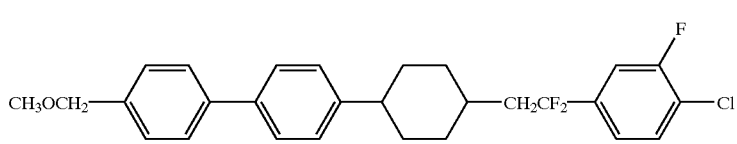 |
| 543 | 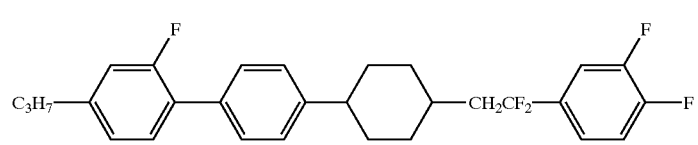 |
| 544 | 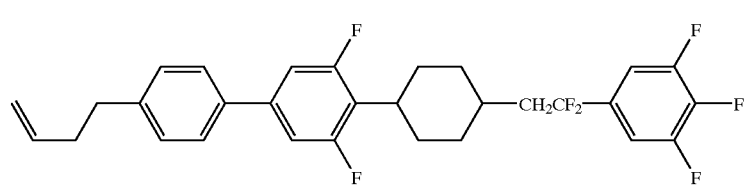 |
| 545 | 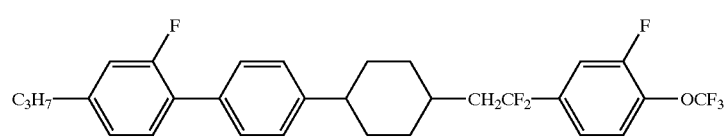 |

-continued
| No. | |
|---|---|
| 546 | 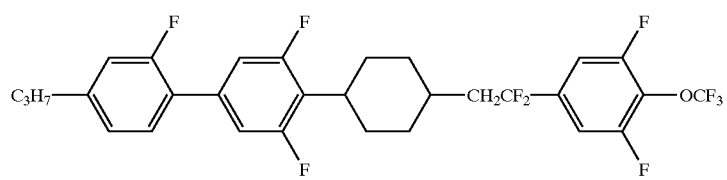 |
| 547 | 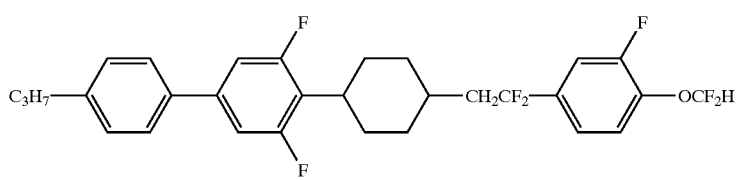 |
| 548 | 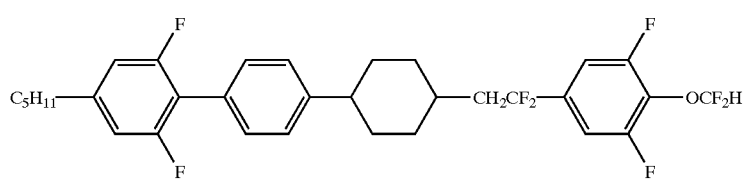 |
| 549 | 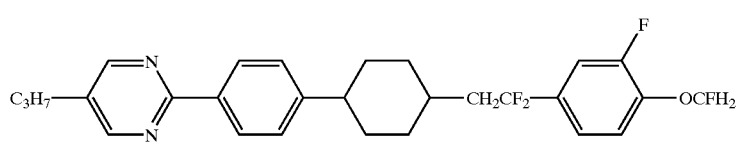 |
| 550 | 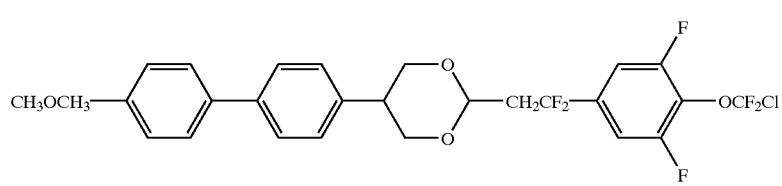 |
| 551 | 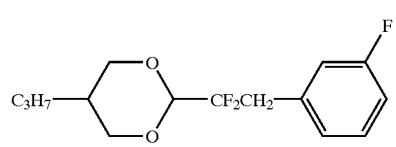 |
| 552 | 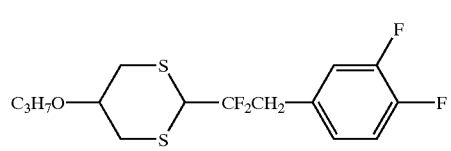 |
| 553 | 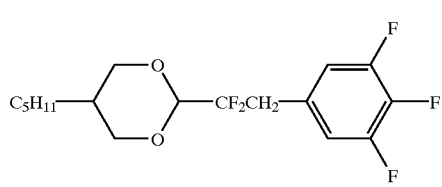 |
| 554 | 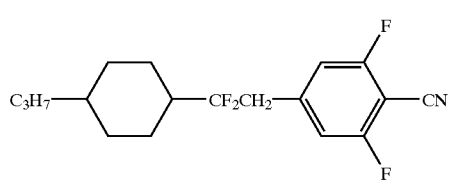 |

-continued
| No. | |
|---|---|
| 555 | 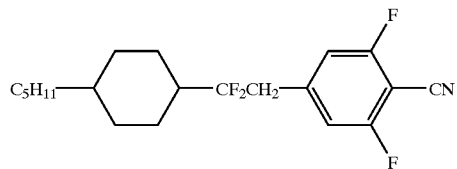 |
| 556 | 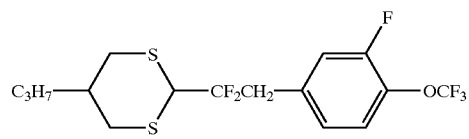 |
| 557 | 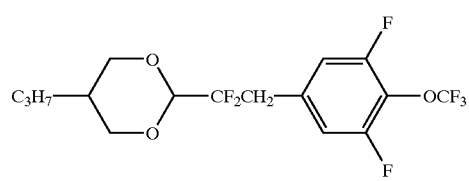 |
| 558 | 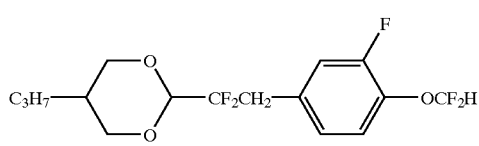 |
| 559 | 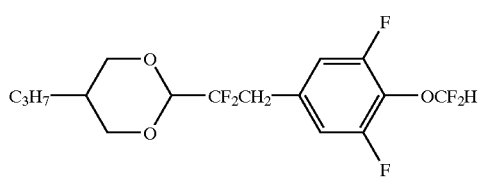 |
| 560 | 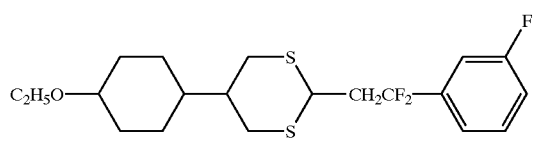 |
| 561 | 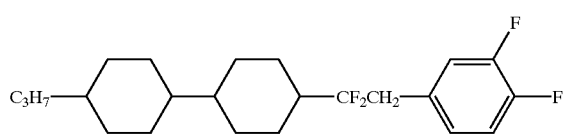 |
| 562 | 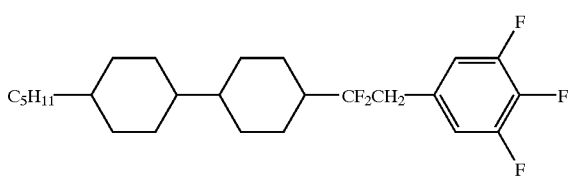 |
| 563 | 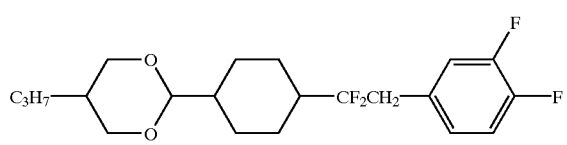 |

| No. | | |
|---|---|---|
| 564 | 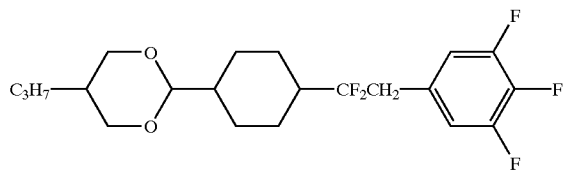 | |
| 565 | 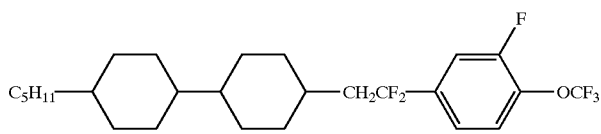 | |
| 566 | 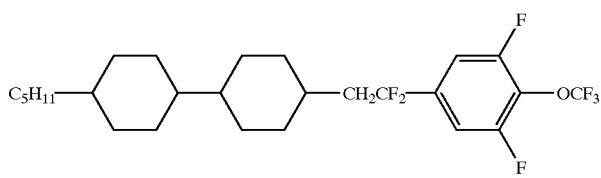 | |

Example 5 (Use Example 1)

Nematic liquid crystal composition A1 comprising 4-(trans-4-propylcyclohexyl)benzonitrile 24%
4-(trans-4-pentylcyclohexyl)benzonitrile 36%
4-(trans-4-heptylcyclohexyl)benzonitrile 25%
4-[4-(4-pentylcyclohexyl)phenyl]benzonitrile 15% the following characteristics.

Clearing point ($T_{NI}$): 72.4° C., $\Delta\epsilon$: 11.0, $\Delta n$: 0.137, viscosity at 20° C. ($\epsilon$-20): 27.0 mPa.s 85 parts by weight of the liquid crystal composition A1 as a mother liquid crystal were mixed with 15 parts by weight of 1,1-difluoro-1-[trans-4-(trans-4-pentylcyclohexyl)cyclohexyl]-2-(3,4-difluorophenyl)ethane (Compound No. 46) obtained in Example 1 to prepare liquid crystal composition B1, for which the physical properties were determined, with the following results: Clearing point ($T_{NI}$): 73.09° C., $\Delta\epsilon$11.41, $\Delta n$: 0.127. The physical properties of the compound extrapolated from that of mother liquid A1 were as shown below.

Clearing point ($T_{NI}$): 77.0° C., $\Delta\epsilon$: 13.7, $\Delta n$: 0.070

Further, this composition B1 was allowed to stand in a freezer at −20° C. for 20 days, but no precipitation of crystals and no production of smectic phase were observed.

Comparative Example 1

Composition B2 was prepared in the same manner as in Example 5, but substituting 2-[trans-4-(trans-4-pentylcyclohexyl)cyclohexyl]-1-(3,4-difluorophenyl)ethane for Compound No. 46, and the physical properties were determined. The physical properties of the compound extrapolated from the result were as shown below.

$T_{NI}$: 109.0° C., $\Delta\epsilon$: 6.33, $\Delta n$: 0.0830

Further, this composition B2 was allowed to stand in a freezer at −20° C. for 20 days, but no precipitation of crystals and no production of smectic phase were observed.

In the following Examples (Use Examples), the compounds used as components in the liquid crystal compositions are designated in accordance with the abbreviated notation shown in the following Table 1.

TABLE 1

Abbreviated notation of compounds using symbols $$R-(A_1)-Z_1-\cdots-Z_n-(A_n)-X$$

| 1) Left terminal group R— | Symbol |
|---|---|
| $C_nH_{2n+1}$— | n- |
| $C_nH_{2n+1}O$— | nO— |
| $C_nH_{2n+1}OC_mH_{2m}$— | nOm- |
| $CH_2=CH$— | V— |
| $CH_2=CHC_nH_{2n}$— | Vn- |
| $C_nH_{2n+1}CH=C_mH_{2m}$— | nVm- |
| $C_nH_{2n+1}CH=CHC_mH_{2m}CH=CHC_kH_{2k}$— | nVmVk- |

| 2) Ring structure —(A_1)—, —(A_n)— | Symbol |
|---|---|
| ![benzene ring] | B |
| ![fluorobenzene ring] | B(F) |
| ![difluorobenzene ring] | B(2F, 3F) |

TABLE 1-continued

Abbreviated notation of compounds using symbols

R—(A₁)—Z₁— ··· —Zₙ—(Aₙ)—X

| Structure | Symbol |
|---|---|
| 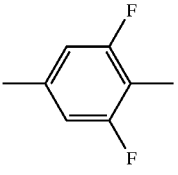 | B(F, F) |
| 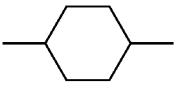 | H |
| 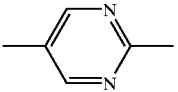 | Py |
| 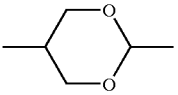 | G |
|  | Ch |

3) Bonding group
—Z₁—, —Zₙ—

| Group | Symbol |
|---|---|
| —C₂H₄— | 2 |
| —C₄H₈— | 4 |
| —COO— | E |
| —C≡C— | T |
| —CH=CH— | V |
| —CF₂O— | CF2O |
| —OCF₂— | OCF2 |
| —CF₂CH₂— | CF2Me |
| —CH₂CF₂— | MeCF2 |

4) Right terminal group
—X

| Group | Symbol |
|---|---|
| —F | —F |
| —Cl | —CL |
| —CN | —C |
| —CF₃ | —CF3 |
| —OCF₃ | —OCF3 |
| —OCF₂H | —OCF2H |
| —OCF₂CF₂H | —OCF2CF2H |
| —CₙH₂ₙ₊₁ | -n |
| —OCₙH₂ₙ₊₁ | —On |
| —COOCH₃ | -EMe |
| —CₙH₂ₙCH=CH₂ | -nV |
| —CₘH₂ₘCH=CHCₙH₂ₙ₊₁ | -mVn |
| —CₘH₂ₘCH=CHCₙH₂ₙF | -mVnF |
| —CₙH₂ₙOCₘH₂ₘ₊₁ | -nOm |
| —CH=CF₂ | —VFF |
| —CₙH₂ₙCH=CF₂ | -nVFF |
| —C≡C—CN | -TC |

TABLE 1-continued

Abbreviated notation of compounds using symbols

R—(A₁)—Z₁— ··· —Zₙ—(Aₙ)—X

5) Example of expression

Example 1; 3-H2B(F, F)B(F)-F

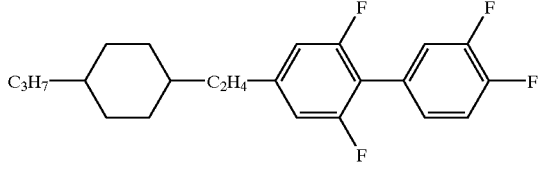

Example 2; 3-HB(F)TB-2

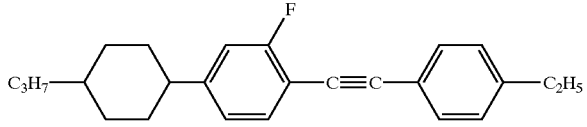

Example 3; 1V2-BEB(F, F)-C

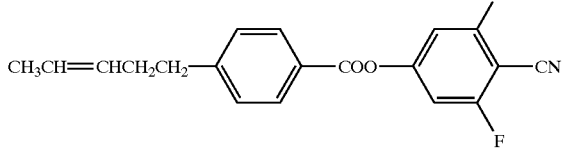

Example 6 (Use Example 2)

A liquid crystal composition was prepared with the following composition:

| | |
|---|---|
| 3-HHCF2MeB (F)—F (No. 561) | 4.0% |
| 3-GHCF2MeB (F)—F (No. 563) | 7.0% |
| 5-GHCF2MeB (F)—F (No. 63) | 7.0% |
| 3-HHCF2MeB (F, F)—F (No. 47) | 4.0% |
| 1V2-BEB (F, F)—C | 5.0% |
| 3-HB—C | 3.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB (F) TB-2 | 6.0% |
| 3-HB (F) TB-3 | 6.0% |

The characteristics of the composition are shown below.

$T_{NI}$=91.9 (° C.)

η=28.4 (mPa·s)

Δn=0.149

Δε=9.4

Vth=1.78 (V)

The helical pitch was 10.5 μm, when 0.8 part of a chiral dopant was added to 100 parts of the above composition.

Example 7 (Use Example 3)

A liquid crystal composition was prepared with the following composition:

| | |
|---|---|
| 3-HHCF2MeB (F)—F (No. 561) | 3.0% |
| 3-HHMeCF2B (F, F)—OCF3 (No. 73) | 3.0% |
| 3-GHCF2MeB (F)—F (No. 563) | 3.0% |
| 5-GHCF2MeB (F)—F (No. 63) | 3.0% |
| 3-GHCF2MeB (F, F)—F (No. 564) | 3.0% |
| 5-GHCF2MeB (F, F)—F (No. 66) | 3.0% |
| 3-HCF2MeB (F, F)—C (No. 554) | 3.0% |
| 5-HCF2MeB (F, F)—C (No. 555) | 3.0% |
| 3-HHCF2MeB (F, F)—F (No. 47) | 3.0% |
| 3-HHMeCF2B (F)—OCF3 (No. 72) | 3.0% |
| 2O1-BEB (F)—C | 6.0% |
| 3O1-BEB (F)—C | 6.0% |
| 4O1-BEB (F)—C | 5.0% |
| 5O1-BEB (F)—C | 5.0% |
| 2-HHB (F)—C | 12.0% |
| 3-HHB (F)—C | 12.0% |
| 3-HB (F) TB-2 | 4.0% |
| 3-HB (F) TB-3 | 4.0% |
| 3-HB (F) TB-4 | 4.0% |
| 3-HHB-1 | 8.0% |
| 3-HHB—O1 | 4.0% |

The characteristics of the composition are shown below.

$T_{NI}$=91.8 (° C.)

$\eta$=89.6 (mPa·s)

$\Delta n$=0.130

$\Delta\epsilon$=29.9

Vth=0.87 (V)

Example 8 (Use Example 4)

A liquid crystal composition was prepared with the following composition:

| | |
|---|---|
| 3-HCF2MeB (F, F)—C (No. 554) | 3.0% |
| 5-PyB-F | 3.0% |
| 3-PyB (F)—F | 2.0% |
| 2-BB—C | 5.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O5 | 3.0% |
| 6-PyB—O6 | 3.0% |
| 6-PyB—O7 | 3.0% |
| 6-PyB—O8 | 3.0% |
| 3-PyBB—F | 6.0% |
| 4-PyBB—F | 6.0% |
| 5-PyBB—F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

The characteristics of the composition are shown below.

$T_{NI}$=93.1 (° C.)

$\eta$=36.7 (mPa·s)

$\Delta n$=0.201

$\Delta\epsilon$=7.1

Vth=2.11 (V)

Example 9 (Use Example 5)

A liquid crystal composition was prepared with the following composition:

| | |
|---|---|
| 3-GHCF2MeB (F, F)—F (No. 564) | 5.0% |
| 5-GHCF2MeB (F, F)—F (No. 66) | 5.0% |
| 3-HCF2MeB (F, F)—C (No. 554) | 3.0% |
| 3-GB—C | 5.0% |
| 4-GB—C | 5.0% |
| 2-BEB—C | 12.0% |
| 3-BEB—C | 4.0% |
| 3-PyB (F)—F | 3.0%. |
| 3-HEB—O4 | 8.0% |
| 4-HEB—O2 | 6.0% |
| 5-HEB—O1 | 6.0% |
| 3-HEB—O2 | 5.0% |
| 5-HEB—O2 | 4.0% |
| 5-HEB-5 | 5.0% |
| 4-HEB-5 | 5.0% |
| 1O—BEB-2 | 4.0% |
| 3-HHB-1 | 6.0% |
| 3-HHEBB—C | 3.0% |
| 3-HBEBB—C | 3.0% |
| 5-HBEBB—C | 3.0% |

The characteristics of the composition are shown below.

NI=67.2 (° C.)

$\eta$=47.6 (mPa·s)

$\Delta n$=0.114

$\Delta\epsilon$=13.1

Vth=1.25 (V)

Example 10 (Use Example 6).

A liquid crystal composition was prepared with the following composition:

| | |
|---|---|
| 3-HHMeCF2B (F, F)—OCF3 (No. 73) | 3.0% |
| 5-HHMeCF2B (F, F)—OCF3 (No. 566) | 3.0% |
| 5-GHCF2MeB (F)—F (No. 63) | 3.0% |
| 5-GHCF2MeB (F, F)—F (No. 66) | 3.0% |
| 3-HHCF2MeB (F, F)—F (No. 47) | 3.0% |
| 5-HHCF2MeB (F, F)—F (No. 562) | 3.0% |
| 3-HHMeCF2B (F)—OCF3 (No. 72) | 3.0% |
| 3-HB—C | 3.0% |
| 7-HB—C | 3.0% |
| 1O1-HB—C | 7.0% |
| 3-HB (F)—C | 7.0% |
| 2-PyB-2 | 2.0% |
| 3-PyB-2 | 2.0% |
| 4-PyB-2 | 2.0% |
| 1O1-HH-3 | 7.0% |
| 2-BTB—O1 | 7.0% |
| 3-HHB-1 | 7.0% |
| 3-HHB—F | 4.0% |
| 3-HHB—O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

The characteristics of the composition are shown below.

$T_{NI}$=82.2 (° C.)

$\eta$=29.4 (mPa·s)

$\Delta n$=0.127

$\Delta\epsilon$=9.7

Vth=1.73 (V)

Example 11 (Use Example 7)

A liquid crystal composition was prepared with the following composition:

| | |
|---|---|
| 3-GHCF2MeB (F)—F (No. 563) | 6.0% |
| 5-GHCF2MeB (F)—F (No. 63) | 6.0% |
| 5-HCF2MeB (F, F)—C (No. 555) | 3.0% |
| 2-BEB (F)—C | 4.0% |
| 3-BEB (F)—C | 4.0% |
| 4-BEB (F)—C | 4.0% |
| 1V2-BEB (F, F)—C | 4.0% |
| 3-HH-EMe | 10.0% |
| 3-HB—O2 | 18.0% |
| 7-HEB—F | 2.0% |
| 3-HHEB—F | 2.0% |
| 5-HHEB—F | 2.0% |
| 3-HBEB—F | 4.0% |
| 2O1-HBEB (F)—C | 2.0% |
| 3-HB (F) EB (F)—C | 2.0% |
| 3-HBEB (F, F)—C | 2.0% |
| 3-HHB—F | 4.0% |
| 3-HHB—O1 | 4.0% |
| 3-HHB-3 | 13.0% |
| 3-HEBEB—F | 2.0% |
| 3-HEBEB-1 | 2.0% |

The characteristics of the composition are shown below.

$T_{NI}$=80.9 (° C.)

$\eta$=39.8 (mPa·s)

$\Delta n$=0.105

$\Delta \epsilon$=21.8

Vth=1.13 (V)

Example 12 (Use Example 8)

A liquid crystal composition was prepared with the following composition:

| | |
|---|---|
| 3-GHCF2MeB (F, F)—F (No. 564) | 7.0% |
| 5-GHCF2MeB (F, F)—F (No. 66) | 7.0% |
| 2-BEB (F)—C | 4.0% |
| 3-BEB (F)—C | 4.0% |
| 4-BEB (F)—C | 6.0% |
| 1V2-BEB (F, F)—C | 9.0% |
| 3-HB—O2 | 10.0% |
| 3-HH-4 | 3.0% |
| 3-HHB—F | 3.0% |
| 3-HHB-1 | 8.0% |
| 3-HHB—O1 | 4.0% |
| 3-HBEB—F | 4.0% |
| 3-HHEB—F | 7.0% |
| 5-HHEB—F | 7.0% |
| 3-H2BTB-2 | 4.0% |
| 3-H2BTB-3 | 4.0% |
| 3-H2BTB-4 | 4.0% |
| 3-HB (F) TB-2 | 5.0% |

The characteristics of the composition are shown below.

$T_{NI}$=89.9 (° C.)

$\eta$=45.6 (mPa·s)

$\Delta n$=0.129

$\Delta \epsilon$=25.3

Vth=1.06 (V)

Example 13 (Use Example 9)

A liquid crystal composition was prepared with the following composition:

| | |
|---|---|
| 3-HHCF2MeB (F)—F (No. 561) | 5.0% |
| 5-HHCF2MeB (F)—F (No. 46) | 5.0% |
| 2-BEB—C | 12.0% |
| 3-BEB—C | 4.0% |
| 4-BEB—C | 6.0% |
| 3-HB—C | 18.0% |
| 3-HEB—O4 | 12.0% |
| 4-HEB—O2 | 8.0% |
| 5-HEB—O1 | 8.0% |
| 3-HEB—O2 | 6.0% |
| 5-HEB—O2 | 5.0% |
| 3-HHB-1 | 7.0% |
| 3-HHB—O1 | 4.0% |

The characteristics of the composition are shown below.

$T_{NI}$=65.5 (° C.)

$\eta$=29.4 (mPa·s)

$\Delta n$=0.107

$\Delta \epsilon$=10.2

Vth=1.31 (V)

Example 14 (Use Example 10)

A liquid crystal composition was prepared with the following composition:

| | |
|---|---|
| 3-HHMeCF2B (F)—OCF3 (No. 72) | 3.0% |
| 5-HHMeCF2B (F)—OCF3 (No. 565) | 3.0% |
| 2-BEB—C | 7.0% |
| 5-BB—C | 9.0% |
| 7-BB—C | 7.0% |
| 1-BTB-3 | 7.0% |
| 2-BTB-1 | 10.0% |
| 1O—BEB-2 | 10.0% |
| 1O—BEB-5 | 12.0% |
| 2-HHB-1 | 4.0% |
| 3-HHB—F | 4.0% |
| 3-HHB-1 | 7.0% |
| 3-HHB—O1 | 4.0% |
| 3-HHB-3 | 13.0% |

The characteristics of the composition are shown below.

$T_{NI}$=67.7 (° C.)

$\eta$=21.9 (mPa·s)

$\Delta n$=0.153

$\Delta \epsilon$32 6.4

Vth=1.80 (V)

Example 15 (Use Example 11)

A liquid crystal composition was prepared with the following composition:

| | |
|---|---|
| 3-HHCF2MeB (F)—F (No. 561) | 4.0% |
| 5-HHCF2MeB (F)—F (No. 46) | 4.0% |
| 3-HHMeCF2B (F)—OCF3 (No. 72) | 4.0% |
| 5-HHMeCF2B (F)—OCF3 (No. 565) | 4.0% |
| 2-HB—C | 5.0% |
| 3-HB—C | 3.0% |
| 3-HB—O2 | 15.0% |

-continued

| | |
|---|---|
| 2-BTB-1 | 3.0% |
| 3-HHB-1 | 8.0% |
| 3-HHB—F | 4.0% |
| 3-HHB—O1 | 5.0% |
| 3-HHB-3 | 14.0% |
| 3-HHEB—F | 4.0% |
| 5-HHEB—F | 4.0% |
| 2-HHB (F)—F | 5.0% |
| 3-HHB (F)—F | 5.0% |
| 5-HHB (F)—F | 4.0% |
| 3-HHB (F, F)—F | 5.0% |

The characteristics of the composition are shown below.
$T_{NI}$=100.3 (° C.)
η=24.1 (mPa·s)
Δn=0.094
Δε=5.4
Vth=2.30 (V)

Example 16 (Use Example 12)

A liquid crystal composition was prepared with the following composition:

| | |
|---|---|
| 3-GHCF2MeB (F)—F (No. 563) | 3.0% |
| 3-HHCF2MeB (F, F)—F (No. 47) | 3.0% |
| 3-BEB (F)—C | 8.0% |
| 3-HB—C | 2.0% |
| V-HB—C | 8.0% |
| 1V-HB—C | 8.0% |
| 3-HB—O2 | 3.0% |
| 3-HH-2V | 14.0% |
| 3-HH-2V1 | 7.0% |
| V2-HHB-1 | 15.0% |
| 3-HHB-1 | 5.0% |
| 3-HHEB—F | 7.0% |
| 3-H2BTB-2 | 6.0% |
| 3-H2BTB-3 | 6.0% |
| 3-H2BTB-4 | 5.0% |

The characteristics of the composition are shown below.
$T_{NI}$=989 (° C.)
η=19.6 (mPa·s)
Δn=0.129
Δε=9.0
Vth=2.07 (V)

Example 17 (Use Example 13)

A liquid crystal composition was prepared with the following composition:

| | |
|---|---|
| 3-HHCF2MeB (F)—F (No. 561) | 5.0% |
| 5-HHCF2MeB (F)—F (No. 46) | 5.0% |
| 3-HHMeCF2B (F, F)—OCF3 (No. 73) | 5.0% |
| 5-HHMeCF2B (F, F)—OCF3 (No. 566) | 5.0% |
| 3-HHCF2MeB (F, F)—F (No. 47) | 5.0% |
| 5-HHCF2MeB (F, F)—F (No. 562) | 5.0% |
| 3-HHMeCF2B (F)—OCF3 (No. 72) | 5.0% |
| 5-HHMeCF2B (F)—OCF3 (No. 565) | 5.0% |
| V2-HB—C | 3.0% |
| 1V2-HB—C | 3.0% |
| 3-HB—C | 3.0% |
| 3-HB (F)—C | 4.0% |
| 2-BTB-1 | 2.0% |

-continued

| | |
|---|---|
| 3-HH-4 | 8.0% |
| 3-HH—VFF | 6.0% |
| 2-HHB—C | 3.0% |
| 3-HHB—C | 6.0% |
| 3-HB (F) TB-2 | 8.0% |
| 3-H2BTB-2 | 5.0% |
| 3-H2BTB-3 | 5.0% |
| 3-H2BTB-4 | 4.0% |

The characteristics of the composition are shown below.
$T_{NI}$=92.0 (° C.)
η=34.9 (mPa·s)
Δn=0.125
Δε=10.9
Vth=1.74 (V)

Example 18 (Use Example 14)

A liquid crystal composition was prepared with the following composition:

| | |
|---|---|
| 5-GHCF2MeB (F)—F (No. 63) | 6.0% |
| 5-BEB(F)—C | 3.0% |
| V—HB—C | 7.0% |
| 5-PyB—C | 6.0% |
| 4-BB-3 | 11.0% |
| 3-HH-2V | 10.0% |
| 5-HH—V | 11.0% |
| V—HHB-1 | 7.0% |
| V2-HHB-1 | 15.0% |
| 3-HHB-1 | 9.0% |
| 1V2-HBB-2 | 10.0% |
| 3-HHEBH-3 | 5.0% |

The characteristics of the composition are shown below.
$T_{NI}$=93.1 (° C.)
η=18.8 (mPa·s)
Δn=0.111
Δε=5.2
Vth=2.22 (V)

Example 19 (Use Example 15)

A liquid crystal composition was prepared with the following composition:

| | |
|---|---|
| 3-HHCF2MeB (F)—F (No. 561) | 6.0% |
| 3-HHCF2MeB (F, F)—F (No. 47) | 4.0% |
| 1V2-BEB (F, F)—C | 8.0% |
| 3-HB—C | 6.0% |
| V2V—HB—C | 8.0% |
| V2V—HH-3 | 19.0% |
| 3-HB—O2 | 4.0% |
| 3-HHB-1 | 10.0% |
| 3-HHB-3 | 15.0% |
| 3-HB (F) TB-2 | 4.0% |
| 3-HB (F) TB-3 | 4.0% |
| 3-H2BTB-2 | 4.0% |
| 3-H2BTB-3 | 4.0% |
| 3-H2BTB-4 | 4.0% |

The characteristics of the composition are shown below.
$T_{NI}$=102.0 (° C.)
η=20.8 (mPa·s)
Δn=0.123

Δε=8.3
Vth=2.05 (V)

Example 20 (Use Example 16)

A liquid crystal composition was prepared with the following composition:

| | |
|---|---|
| 3-HHMeCF2B (F, F)-OCF3 (No. 73) | 3.0% |
| 3-HHCF2MeB (F, F)-F (No. 47) | 3.0% |
| 5-HHCF2MeB (F, F)-F (No. 562) | 3.0% |
| 3-HHMeCF2B (F)-OCF3 (No. 72) | 3.0% |
| 5-HHMeCF2B (F)-OCF3 (No. 565) | 3.0% |
| V2-HB-TC | 6.0% |
| 3-HB-TC | 10.0% |
| 3-HB-C | 3.0% |
| 5-HB-C | 3.0% |
| 5-BB-C | 3.0% |
| 2-BTB-1 | 10.0% |
| 2-BTB-O1 | 5.0% |
| 3-HH-4 | 5.0% |
| 3-HHB-1 | 10.0% |
| 3-HHB-3 | 11.0% |
| 3-H2BTB-2 | 3.0% |
| 3-H2BTB-3 | 3.0% |
| 3-HB (F) TB-2 | 3.0% |
| 5-BTB (F) TB-3 | 10.0% |

The characteristics of the composition are shown below.
$T_{NI}$=100.0 (° C.)
η=21.3 (mPa·s)
Δn=0.191
Δε=7.5
Vth=1.97 (V)

Example 21 (Use Example 17)

A liquid crystal composition was prepared with the following composition:

| | |
|---|---|
| 3-HHCF2MeB (F)-F (No. 561) | 3.0% |
| 5-HHCF2MeB (F)-F (No. 46) | 4.0% |
| 3-HHMeCF2B (F, F)-OCF3 (No. 73) | 4.0% |
| 5-HHMeCF2B (F, F)-OCF3 (No. 566) | 4.0% |
| 5-GHCF2MeB (F, F)-F (No. 66) | 3.0% |
| 1V2-BEB (F, F)-C | 3.0% |
| 3-HB-C | 3.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-2 | 5.0% |
| 3-H2BTB-3 | 4.0% |
| 3-H2BTB-4 | 4.0% |
| 3-HHB-1 | 4.0% |

The characteristics of the composition are shown below.
$T_{NI}$=84.6 (° C.)
η=20.9 (mPa·s)
Δn=0.118
Δε=6.3
Vth=2.08 (V)

Example 22 (Use Example 18)

A liquid crystal composition was prepared with the following composition:

| | |
|---|---|
| 3-HHCF2MeB (F)-F (No. 561) | 3.0% |
| 2-HHB (F)-F | 14.0% |
| 3-HHB (F)-F | 17.0% |
| 5-HHB (F)-F | 16.0% |
| 2-H2HB (F)-F | 10.0% |
| 3-H2HB (F)-F | 5.0% |
| 5-H2HB (F)-F | 10.0% |
| 2-HBB (F)-F | 6.0% |
| 3-HBB (F)-F | 6.0% |
| 5-HBB (F)-F | 13.0% |

The characteristics of the composition are shown below.
$T_{NI}$=99.8 (° C.)
η=26.2 (mPa·s)
Δn=0.093
Δε=5.3
Vth=2.20 (V)

Example 23 (Use Example 19)

A liquid crystal composition was prepared with the following composition:

| | |
|---|---|
| 3-HHCF2MeB (F)-F (No. 561) | 3.0% |
| 5-HHCF2MeB (F)-F (No. 46) | 3.0% |
| 3-HHMeCF2B (F)-OCF3 (No. 72) | 3.0% |
| 5-HHMeCF2B (F)-OCF3 (No. 565) | 3.0% |
| 7-HB (F, F)-F | 2.0% |
| 3-HB-O2 | 7.0% |
| 2-HHB (F)-F | 6.0% |
| 3-HHB (F)-F | 6.0% |
| 5-HHB (F)-F | 7.0% |
| 2-HBB (F)-F | 9.0% |
| 3-HBB (F)-F | 9.0% |
| 5-HBB (F)-F | 16.0% |
| 2-HBB-F | 4.0% |
| 3-HBB-F | 4.0% |
| 5-HBB-F | 3.0% |
| 3-HBB (F, F)-F | 5.0% |
| 5-HBB (F, F)-F | 10.0% |

The characteristics of the composition are shown below.
$T_{NI}$=83.3 (° C.)
η=29.1 (mPa·s)
Δn=0.114
Δε=6.9
Vth=1.88 (V)

Example 24 (Use Example 20)

A liquid crystal composition was prepared with the following composition:

| | |
|---|---|
| 3-HHCF2MeB (F)-F (No. 561) | 3.0% |
| 3-GHCF2MeB (F)-F (No. 563) | 3.0% |
| 3-GHCF2MeB (F, F)-F (No. 564) | 3.0% |
| 3-HHCF2MeB (F, F)-F (No. 47) | 3.0% |
| 5-HHCF2MeB (F, F)-F (No. 562) | 3.0% |
| 3-HHMeCF2B (F)-OCF3 (No. 72) | 3.0% |
| 5-HB-CL | 6.0% |
| 3-HH-4 | 12.0% |
| 3-HH-5 | 4.0% |
| 3-HHB-F | 4.0% |
| 3-HHB-CL | 3.0% |
| 4-HHB-CL | 4.0% |

-continued

| | |
|---|---|
| 3-HHB (F)-F | 7.0% |
| 4-HHB (F)-F | 7.0% |
| 5-HHB (F)-F | 7.0% |
| 7-HHB (F)-F | 7.0% |
| 5-HBB (F)-F | 4.0% |
| 5-HBBH-1O1 | 3.0% |
| 3-HHBB (F, F)-F | 2.0% |
| 4-HHBB (F, F)-F | 3.0% |
| 5-HHBB (F, F)-F | 3.0% |
| 3-HH2BB (F, F)-F | 3.0% |
| 4-HH2BB (F, F)-F | 3.0% |

The characteristics of the composition are shown below.
NI 114.7 (° C.)
$\eta$=31.7 (mPa·s)
$\Delta n$=0.088
$\Delta\epsilon$=6.5
Vth=2.13 (V)

Example 25 (Use Example 21)

A liquid crystal composition was prepared with the following composition:

| | |
|---|---|
| 3-HHCF2MeB (F)-F (No. 561) | 5.0% |
| 5-HHCF2MeB (F)-F (No. 46) | 5.0% |
| 3-HHMeCF2B (F, F)-OCF3 (No. 73) | 3.0% |
| 3-GHCF2MeB (F)-F (No. 563) | 5.0% |
| 5-GHCF2MeB (F)-F (No. 63) | 4.0% |
| 3-GHCF2MeB (F, F)-F (No. 564) | 6.0% |
| 5-GHCF2MeB (F, F)-F (No. 66) | 3.0% |
| 3-HHMeCF2B (F)-OCF3 (No. 72) | 5.0% |
| 5-HHMeCF2B (F)-OCF3 (No. 565) | 4.0% |
| 3-HHB (F, F)-F | 4.0% |
| 3-H2HB (F, F)-F | 3.0% |
| 4-H2HB (F, F)-F | 3.0% |
| 5-H2HB (F, F)-F | 3.0% |
| 3-HBB (F, F)-F | 11.0% |
| 5-HBB (F, F)-F | 10.0% |
| 3-H2BB (F, F)-F | 10.0% |
| 5-HHBB (F, F)-F | 3.0% |
| 5-HHEBB-F | 2.0% |
| 3-HH2BB (F, F)-F | 3.0% |
| 1O1-HBBH-4 | 4.0% |
| 1O1-HBBH-5 | 4.0% |

The characteristics of the composition are shown below.
$T_{NI}$=91.9 (° C.)
$\eta$=52.4 (mPa·s)
$\Delta n$=0.103
$\Delta\epsilon$=13.8
Vth=1.50 (V)

Example 26 (Use Example 22)

A liquid crystal composition was prepared with the following composition:

| | |
|---|---|
| 3-HHMeCF2B (F, F)-OCF3 (No. 73) | 5.0% |
| 5-HHMeCF2B (F, F)-OCF3 (No. 566) | 4.0% |
| 3-HHMeCF2B (F)-OCF3 (No. 72) | 3.0% |
| 5-HHMeCF2B (F)-OCF3 (No. 565) | 3.0% |
| 5-HB-F | 12.0% |
| 6-HB-F | 9.0% |
| 7-HB-F | 7.0% |

-continued

| | |
|---|---|
| 2-HHB-OCF3 | 4.0% |
| 3-HHB-OCF3 | 4.0% |
| 4-HHB-OCF3 | 4.0% |
| 5-HHB-OCF3 | 3.0% |
| 3-HH2B-OCF3 | 3.0% |
| 5-HH2B-OCF3 | 3.0% |
| 3-HHB (F, F)-OCF3 | 3.0% |
| 3-HBB (F)-F | 10.0% |
| 5-HBB (F)-F | 10.0% |
| 3-HH2B (F)-F | 3.0% |
| 3-HB (F) BH-3 | 3.0% |
| 5-HBBH-3 | 3.0% |
| 3-HHB (F, F)-OCF2H | 4.0% |

The characteristics of the composition are shown below.
$T_{NI}$=77.7 (° C.)
$\eta$=22.3 (mPa·s)
$\Delta n$=0.089
$\Delta\epsilon$=6.2
Vth=1.88 (V)

Example 27 (Use Example 23)

A liquid crystal composition was prepared with the following composition:

| | |
|---|---|
| 3-HHCF2MeB (F)-F (No. 561) | 3.0% |
| 5-HHCF2MeB (F)-F (No. 46) | 3.0% |
| 3-HHCF2MeB (F, F)-F (No. 47) | 5.0% |
| 5-HHCF2MeB (F, F)-F (No. 562) | 3.0% |
| 2-HHB (F)-F | 3.0% |
| 2-HBB (F)-F | 7.0% |
| 3-HBB (F)-F | 7.0% |
| 4-HBB (F)-F | 2.0% |
| 5-HBB (F)-F | 15.0% |
| 2-H2BB (F)-F | 7.0% |
| 3-H2BB (F)-F | 7.0% |
| 3-HBB (F, F)-F | 14.0% |
| 5-HBB (F, F)-F | 6.0% |
| 2-HHB (F, F)-F | 5.0% |
| 3-HHB (F, F)-F | 5.0% |
| 4-HHB (F, F)-F | 5.0% |
| 3-HHB-F | 3.0% |

The characteristics of the composition are shown below.
$T_{NI}$=96.8 (° C.)
$\eta$=37.6 (mPa·s)
$\Delta n$=0.128
$\Delta\epsilon$=8.2
Vth=1.87 (V)

Example 28 (Use Example 24)

A liquid crystal composition was prepared with the following composition:

| | |
|---|---|
| 3-HHMeCF2B (F, F)-OCF3 (No. 73) | 4.0% |
| 5-HHMeCF2B (F, F)-OCF3 (No. 566) | 4.0% |
| 3-GHCF2MeB (F, F)-F (No. 564) | 4.0% |
| 5-GHCF2MeB (F, F)-F (No. 66) | 3.0% |
| 3-HHCF2MeB (F, F)-F (No. 47) | 4.0% |
| 5-HHCF2MeB (F, F)-F (No. 562) | 4.0% |
| 3-H2HB (F, F)-F | 5.0% |
| 5-H2HB (F, F)-F | 5.0% |
| 3-HHB (F, F)-F | 5.0% |

-continued

| | |
|---|---|
| 4-HHB (F, F)-F | 5.0% |
| 3-HH2B (F, F)-F | 9.0% |
| 5-HH2B (F, F)-F | 9.0% |
| 3-HBB (F, F)-F | 11.0% |
| 5-HBB (F, F)-F | 11.0% |
| 3-HBEB (F, F)-F | 2.0% |
| 4-HBEB (F, F)-F | 2.0% |
| 5-HBEB (F, F)-F | 2.0% |
| 3-HHEB (F, F)-F | 5.0% |
| 4-HHEB (F, F)-F | 3.0% |
| 5-HHEB (F, F)-F | 3.0% |

The characteristics of the composition are shown below.
$T_{NI}$=74.1 (° C.)
$\eta$=42.5 (mPa·s)
$\Delta n$=0.085
$\Delta \epsilon$=14.1
Vth=1.24 (V)

Example 29 (Use Example 25)

A liquid crystal composition was prepared with the following composition:

| | |
|---|---|
| 3-HHCF2MeB (F)-F (No. 561) | 4.0% |
| 5-HHCF2MeB (F)-F (No. 46) | 3.0% |
| 3-HCF2MeB (F, F)-C (No. 554) | 3.0% |
| 5-HCF2MeB (F, F)-C (No. 555) | 2.0% |
| 3-HHMeCF2B (F)-OCF3 (No. 72) | 3.0% |
| 7-HB (F)-F | 2.0% |
| 5-H2B (F)-F | 2.0% |
| 3-HB-O2 | 10.0% |
| 3-HH-4 | 5.0% |
| 2-HHB (F)-F | 10.0% |
| 3-HHB (F)-F | 10.0% |
| 5-HHB (F)-F | 10.0% |
| 3-H2HB (F)-F | 3.0% |
| 2-HBB (F)-F | 3.0% |
| 3-HBB (F)-F | 3.0% |
| 5-HBB (F)-F | 3.0% |
| 2-H2BB (F)-F | 3.0% |
| 3-H2BB (F)-F | 4.0% |
| 3-HHB-1 | 8.0% |
| 3-HHB-O1 | 5.0% |
| 3-HHB-3 | 4.0% |

The characteristics of the composition are shown below.
$T_{NI}$=87.7 (° C.)
$\eta$=25.2 (mPa·s)
$\Delta n$=0.090
$\Delta \epsilon$=5.4
Vth=2.17 (V)

Example 30 (Use Example 26)

A liquid crystal composition was prepared with the following composition:

| | |
|---|---|
| 3-GHCF2MeB (F)-F (No. 563) | 6.0% |
| 5-GHCF2MeB (F)-F (No. 63) | 4.0% |
| 3-HHCF2MeB (F, F)-F (No. 47) | 4.0% |
| 5-HHCF2MeB (F, F)-F (No. 562) | 3.0% |
| 3-HHMeCF2B (F)-OCF3 (No. 72) | 3.0% |
| 5-HHMeCF2B (F)-OCF3 (No. 565) | 3.0% |
| 7-HB (F, F)-F | 3.0% |

-continued

| | |
|---|---|
| 3-H2HB (F, F)-F | 9.0% |
| 4-H2HB (F, F)-F | 9.0% |
| 5-H2HB (F, F)-F | 9.0% |
| 3-HHB (F, F)-F | 5.0% |
| 4-HHB (F, F)-F | 5.0% |
| 3-HH2B (F, F)-F | 15.0% |
| 5-HH2B (F, F)-F | 10.0% |
| 3-HBB (F, F)-F | 3.0% |
| 5-HBB (F, F)-F | 3.0% |
| 3-HBCF2OB (F, F)-F | 6.0% |

The characteristics of the composition are shown below.
$T_{NI}$=71.6 (° C.)
$\eta$=35.1 (mPa·s)
$\Delta n$=0.076
$\Delta \epsilon$=11.4
Vth=1.36 (V)

Example 31 (Use Example 27)

A liquid crystal composition was prepared with the following composition:

| | |
|---|---|
| 3-HHCF2MeB (F)-F (No. 561) | 5.0% |
| 3-HHMeCF2B (F, F)-OCF3 (No. 73) | 3.0% |
| 3-GHCF2MeB (F)-F (No. 563) | 3.0% |
| 5-GHCF2MeB (F)-F (No. 63) | 7.0% |
| 5-GHCF2MeB (F, F)-F (No. 66) | 7.0% |
| 3-HHMeCF2B (F)-OCF3 (No. 72) | 3.0% |
| 5-HHMeCF2B (F)-OCF3 (No. 565) | 3.0% |
| 7-HB (F, F)-F | 3.0% |
| 3-H2HB (F, F)-F | 10.0% |
| 4-H2HB (F, F)-F | 10.0% |
| 3-HHB (F, F)-F | 10.0% |
| 4-HHB (F, F)-F | 5.0% |
| 3-HBB (F, F)-F | 3.0% |
| 3-HHEB (F, F)-F | 4.0% |
| 4-HHEB (F, F)-F | 3.0% |
| 5-HHEB (F, F)-F | 3.0% |
| 2-HBEB (F, F)-F | 3.0% |
| 3-HBEB (F, F)-F | 3.0% |
| 5-HBEB (F, F)-F | 3.0% |
| 3-HGB (F, F)-F | 3.0% |
| 3-HHBB (F, F)-F | 6.0% |

The characteristics of the composition are shown below.
$T_{NI}$=72.5 (° C.)
$\eta$=48.4 (mPa·s)
$\Delta n$=0.078
$\Delta \epsilon$=16.2
Vth=1.17 (V)

Example 32 (Use Example 28)

A liquid crystal composition was prepared with the following composition:

| | |
|---|---|
| 5-HCF2MeB (F, F)-C (No. 555) | 4.0% |
| 5-HHMeCF2B (F)-OCF3 (No. 565) | 4.0% |
| 5-H4HB (F, F)-F | 7.0% |
| 5-H4HB-OCF3 | 15.0% |
| 3-H4HB (F, F)-CF3 | 8.0% |
| 5-H4HB (F, F)-CF3 | 10.0% |
| 3-HB-CL | 3.0% |
| 5-HB-CL | 3.0% |

-continued

| | |
|---|---|
| 2-H2BB (F)-F | 5.0% |
| 3-H2BB (F)-F | 10.0% |
| 5-H2HB (F, F)-F | 3.0% |
| 3-HHB-OCF3 | 5.0% |
| 3-H2HB-OCF3 | 5.0% |
| V-HHB (F)-F | 5.0% |
| 3-HHB (F)-F | 5.0% |
| 5-HHB (F)-F | 5.0% |
| 3-HBEB (F, F)-F | 3.0% |

The characteristics of the composition are shown below.

$T_{NI}$=67.6 (° C.)

η=28.7 (mPa·s)

Δn=0.095

Δε=9.4

Vth=1.46 (V)

Example 33 (Use Example 29)

A liquid crystal composition was prepared with the following composition:

| | |
|---|---|
| 3-HHMeCF2B (F, F)-OCF3 (No. 73) | 4.0% |
| 3-GHCF2MeB (F)-F (No. 563) | 3.0% |
| 3-HHCF2MeB (F, F)-F (No. 47) | 5.0% |
| 5-HB-CL | 6.0% |
| 3-HH-4 | 7.0% |
| 3-HB-O2 | 20.0% |
| 3-H2HB (F, F)-F | 5.0% |
| 3-HHB (F, F)-F | 5.0% |
| 3-HBB (F, F)-F | 6.0% |
| 2-HHB (F)-F | 5.0% |
| 3-HHB (F)-F | 5.0% |
| 5-HHB (F)-F | 5.0% |
| 2-H2HB (F)-F | 2.0% |
| 3-H2HB (F)-F | 1.0% |
| 5-H2HB (F)-F | 2.0% |
| 3-HHBB (F, F)-F | 4.0% |
| 3-HBCF2OB-OCF3 | 4.0% |
| 5-HBCF2OB (F, F)-CF3 | 4.0% |
| 3-HHB-1 | 3.0% |
| 3-HHB-O1 | 4.0% |

The characteristics of the composition are shown below.

$T_{NI}$=73.1 (° C.)

η=23.4 (mPa·s)

Δn=0.084

Δε=5.9

Vth==1.87 (V)

As mentioned above, the liquid crystalline compounds of the present invention have large Δε, relatively small Δn, low viscosity and excellent compatibility with other liquid crystal compositions even at low temperature. Further, they are chemically stable. Accordingly, the liquid crystalline compounds of the present invention can provide liquid crystal compositions of suitable various characteristics when they are added as a component in the liquid crystal composition.

What is claimed is:

1. A liquid crystalline compound represented by formula (1)

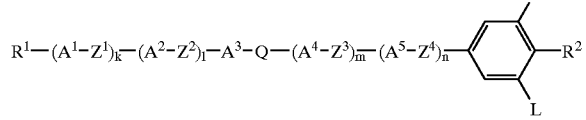

wherein $R^1$ represents hydrogen or $C_1$–$C_{15}$ alkyl in which one or more non-adjacent methylene may be replaced by oxygen, sulfur or —CH═CH— and one or more hydrogen may be replaced by halogen; $R^2$ represents hydrogen, cyano, halogen or $C_1$–$C_{15}$ alkyl in which one or more non-adjacent methylene may be replaced by oxygen, sulfur or —CH═CH— and one or more hydrogen may be replaced by halogen; L represents halogen or hydrogen; $A^1$, $A^2$, $A^4$ and $A^5$ each independently represent trans-1,4-cyclohexylene or 1,4-phenylene, one or more —$CH_2$— in the trans-1,4-cyclohexylene may be replaced by oxygen or sulfur, one or more ═CH— in the 1,4-phenylene may be replaced by nitrogen, and one or more hydrogen in the 1,4-phenylene ring may be replaced by halogen; $A^3$ represents trans-1,4-cyclohexylene in which one or more —$CH_2$— may be replaced by oxygen or sulfur; $Z^1$,$Z^2$,$Z^3$ and $Z^4$ each independently represent —COO—, —OCO—, —$CH_2CH_2$—, —$(CH_2)_4$—, —$CH_2O$ —, —$OCH_2$—, —$CF_2O$—, —$OCF_2$— or a single bond; Q represents —$CF_2CH_2$— or —$CH_2CF_2$—; and k, l, m and n each independently represent 0 or 1 with the condition of k+l+m+n≦2.

2. The liquid crystalline compound of claim 1 wherein k, l, m, and n are all 0.

3. The liquid crystalline compound of claim 1 wherein k+l is 1 and both m and n are 0.

4. The liquid crystalline compound of claim 1 wherein both k and l are 0 and m+n is 1.

5. The liquid crystalline compound of claim 1 wherein k+l is 1 and m+n is 1.

6. The liquid crystalline compound of claim 1 wherein both k and l are 0 and both m and n are 1.

7. The liquid crystalline compound of claim 1 wherein $A^3$ is trans-1,4-cyclohexylene.

8. The liquid crystalline compound of claim 1 wherein $R^2$ is fluorine.

9. The liquid crystalline compound of claim 1 wherein $A^3$ is trans-1,4-cyclohexylene and $R^2$ is fluorine.

10. The liquid crystalline compound of claim 1 wherein k+l is 1, both m and n are 0, $A^1$ or $A^2$ is trans-1,4-cyclohexylene, $A^3$ is trans-1,4-cyclohexylene, and $Z^1$ or $Z^2$ is a single bond.

11. The liquid crystalline compound of claim 1 wherein k+l is 1, both m and n are 0, $A^1$ or $A^2$ is trans-1,4-cyclohexylene, $A^3$ is trans-1,4-cyclohexylene, $Z^1$ or $Z^2$ is a single bond and $R^2$ and L is fluorine.

12. A liquid crystal composition which comprises at least one liquid crystalline compound represented by formula (1) as defined in claim 1.

13. The liquid crystal composition of claim 12 which further comprises as a second component at least one compound selected from the group consisting of the compound of formula (2), the compound of formula (3) or the compound of formula (4)

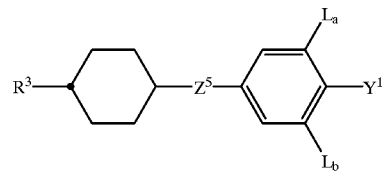
(2)

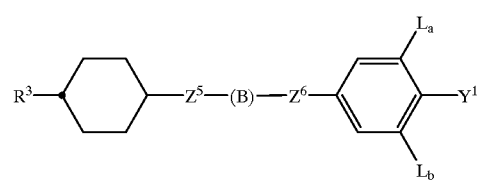
(3)

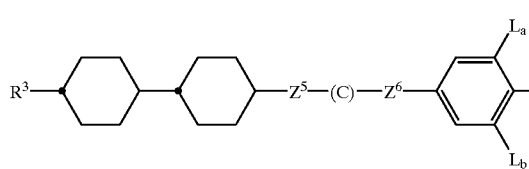
(4)

wherein $R^3$, $Y^1$, $L_a$, $L_b$, $Z^5$ and $Z^6$ may be identical or different between each formula; $R^3$ represents $C_1$–$C_{10}$ alkyl in which one or more non-adjacent methylene may be replaced by oxygen or —CH═CH— and any hydrogen may be replaced by fluorine; $Y^1$ represents fluorine, chlorine, $OCF_3$, $OCHF_2$, $CF_3$, $CHF_2$, $CH_2F$, $OCF_2CHF_2$ or $OCF_2CHF$ $CF_3$; $L_a$ and $L_b$ each independently represent hydrogen or fluorine; $Z^5$ and $Z^6$ each independently represent —$CH_2CH_2$—, —$(CH_2)_4$—, —COO—, —$CF_2O$—, —$OCF_2$—, —CH═CH— or a single bond; ring B represents trans-1,4-cyclohexylene, 1,3-dioxane-2,5-diyl or 1,4-phenylene in which hydrogen may be replaced by fluorine; ring C represents trans-1,4-cyclohexylene or 1,4-phenylene in which hydrogen may be replaced by fluorine; and in the above compound of each formula, each atom constituting the compound may include its isotope.

14. The liquid crystal composition of claim 12 which further comprises as a second component at least one compound selected from the group consisting of the compound of formula (5) or the compound of formula (6)

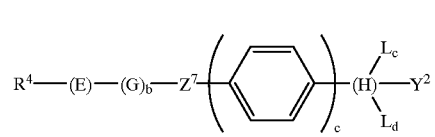
(5)

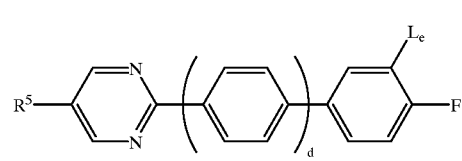
(6)

wherein $R^4$ and $R^5$ each independently represent $C_1$–$C_{10}$ alkyl in which one or more non-adjacent methylene may be replaced by oxygen or —CH═CH— and any hydrogen may be replaced by fluorine; $Y^2$ represents —CN or —C≡C—CN; ring E represents trans-1,4-cyclohexylene, 1,4-phenylene, 1,3-dioxane-2,5-diyl or pyrimidine-2,5-diyl; ring G represents trans-1,4-cyclohexylene, 1,4-phenylene in which hydrogen may be replaced by fluorine or pyrimidine-2,5-diyl; ring H represents trans-1,4-cyclohexylene or 1,4-phenylene; $Z^7$ represents —$CH_2CH_2$—, —COO— or a single bond; $L_c$, $L_d$ and $L_e$ each independently represent hydrogen or fluorine; b, c and d each independently represent 0 or 1; and in the above compound of each formula, each atom constituting the compound may include its isotope.

15. The liquid crystal composition of claim 13 which further comprises as a third component at least one compound selected from the group consisting of the compound of formula (7), the compound of formula (8) or the compound of formula (9)

(7)

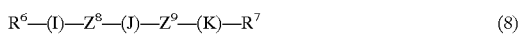
(8)

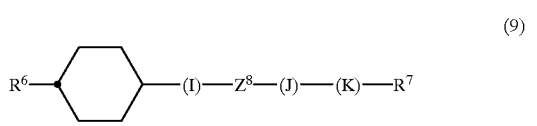
(9)

wherein $R^6$, $R^7$, I, J and K may be identical or different between each formula; $R^6$ and $R^7$ each independently represent $C_1$–$C_{10}$ alkyl in which one or more non-adjacent methylene may be replaced by oxygen or —CH═CH— and any hydrogen may be replaced by fluorine; I, J and K each independently trans-1,4-cyclohexylene, pyrimidine-2,5-diyl or 1,4-phenylene in which hydrogen may be replaced by fluorine; $Z^8$ and $Z^9$ each independently represent —C≡C—, —COO—, —$CH_2CH_2$—, —CH═CH— or a single bond, and in the above compound of each formula, each atom constituting the compound may include its isotope.

16. The liquid crystal composition of claim 14 which further comprises as a third component at least one compound selected from the group consisting of the compound of formula (7), the compound of formula (8) or the compound of formula (9)

(7)

(8)

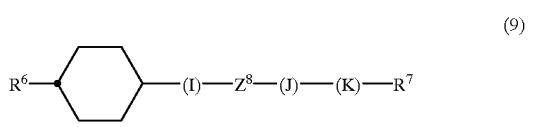
(9)

wherein $R^6$, $R^7$, I, J and K may be identical or different between each formula; $R^6$ and $R^7$ each independently represent $C_1$–$C_{10}$ alkyl in which one or more non-adjacent methylene may be replaced by oxygen or —CH═CH— and any hydrogen may be replaced by fluorine; I, J and K each independently trans-1,4-cyclohexylene, pyrimidine-2,5-diyl or 1,4-phenylene in which hydrogen may be replaced by fluorine; $Z^8$ and $Z^9$ each independently represent —C≡C—, —COO—, —$CH_2CH_2$—, —CH═CH— or a single bond, and in the above compound of each formula, each atom constituting the compound may include its isotope.

17. The liquid crystal composition of claim 13 which further comprises as a third component at least one compound selected from the group consisting of the compound of formula (5) or the compound of formula (6)

(5)

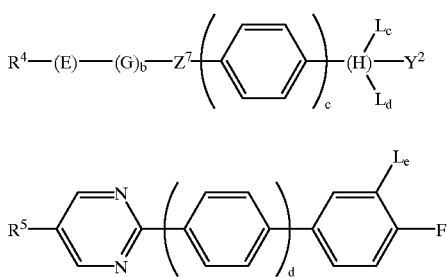

(6)

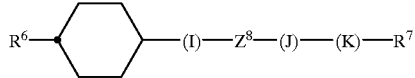

wherein $R^4$ and $R^5$ each independently represent $C_1$–$C_{10}$ alkyl in which one or more non-adjacent methylene may be replaced by oxygen or —CH═CH— and any hydrogen may be replaced by fluorine; $Y^2$ represents —CN or —C≡C—CN; ring E represents trans-1,4-cyclohexylene, 1,4-phenylene, 1,3-dioxane-2,5-diyl or pyrimidine-2,5-diyl; ring G represents trans-1,4-cyclohexylene, 1,4-phenylene in which hydrogen may be replaced by fluorine or pyrimidine-2,5-diyl; ring H represents trans-1,4-cyclohexylene or 1,4-phenylene; $Z^7$ represents —CH$_2$CH$_2$—, —COO— or a single bond; $L_c$, $L_d$ and $L_e$ each independently represent hydrogen or fluorine; b, c and d each independently represent 0 or 1; and in the above compound of each formula, each atom constituting the compound may include its isotope, and as a fourth component at least one of the compound selected from the group consisting of the compound of formula (7), the compound of formula (8) or the compound of formula (9)

$R^6$—(I)—$Z^8$—(J)—$Z^9$—$R^7$      (7)

$R^6$—(I)—$Z^8$—(J)—$Z^9$—(K)—$R^7$      (8)

(9)

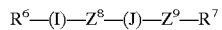

wherein $R^6$, $R^7$, I, J and K may be identical or different between each formula; $R^6$ and $R^7$ each independently represent $C_1$–$C_{10}$ alkyl in which one or more non-adjacent methylene may be replaced by oxygen or —CH═CH— and any hydrogen may be replaced by fluorine; I, J and K each independently trans-1,4-cyclohexylene, pyrimidine-2,5-diyl or 1,4-phenylene in which hydrogen may be replaced by fluorine; $Z^8$ and $Z^9$ each independently represent —C≡C—, —COO—, —CH$_2$CH$_2$—, —CH═CH— or a single bond, and in the above compound of each formula, each atom constituting the compound may include its isotope.

18. The liquid crystal composition of any one of claims 12–17 which further comprises an optically active compound.

19. A liquid crystal display device composed of the liquid crystal composition as claimed in any one of claims 12-17.

20. A liquid crystal display composed of the liquid crystal composition as claimed in claim 18.

* * * * *

UNITED STATES PATENT AND TRADEMARK OFFICE
CERTIFICATE OF CORRECTION

PATENT NO.     : 6,500,503 B2
DATED          : December 31, 2002
INVENTOR(S)    : Koichi Shibata et al.

It is certified that error appears in the above-identified patent and that said Letters Patent is hereby corrected as shown below:

<u>Title page,</u>
Item [75], correct the third named inventor to -- Hiroyuki Takeuchi --.

Signed and Sealed this

Tenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,500,503 B2
DATED         : December 31, 2002
INVENTOR(S)   : Shibata et al.

It is certified that error appears in the above-identified patent and that said Letters Patent is hereby corrected as shown below:

Title page,
Item [*] Notice, delete the phrase "by 33 days" and insert -- by 12 days --

Signed and Sealed this

Ninth Day of December, 2003

JAMES E. ROGAN
*Director of the United States Patent and Trademark Office*